United States Patent [19]

Leppla et al.

[11] Patent Number: 5,591,631
[45] Date of Patent: Jan. 7, 1997

[54] ANTHRAX TOXIN FUSION PROTEINS, NUCLEIC ACID ENCODING SAME

[75] Inventors: Stephen H. Leppla, Bethesda; Kurt R. Klimpel, Gaithersburg, both of Md.; Naveen Arora; Yogendra Singh, both of Delhi, India; Peter J. Nicholls, Welling Kent, United Kingdom

[73] Assignee: The United States of America as represented by the Department of Health and Human Services, Washington, D.C.

[21] Appl. No.: 21,601

[22] Filed: Feb. 12, 1993

[51] Int. Cl.$^6$ .................. C07K 19/00; C12N 15/31; C12N 15/70
[52] U.S. Cl. ................... 435/252.3; 435/320.1; 536/23.4; 536/23.7; 530/350; 530/402
[58] Field of Search ................... 536/23.4, 23.7; 530/350, 402; 514/2; 424/85, 91, 88, 92; 435/320.1, 252.3

[56] References Cited

PUBLICATIONS

Klimpel, Kurt R., et al. (1992) "Anthrax toxin protective antigen is activated by a cell surface protease with the sequence specificity and catalytic properties of furin", *Proceedings of the National Academy of Sciences of USA*, 89(21):10277–10281.

Arora, Navene, et al. (1993) "Residues 1–254 of anthrax toxin lethal factor are sufficient to cause cellular uptake of fused polypeptides", *Journal of Biological Chemistry*, 268(5): 3334–3341.

Robertson et al "Molecular cloning and expression in *E. coli* of the lethal factor gene of *B. anthracis*", *Gene* 44:71–78 (1986).

Bartkus et al "Transcriptional Regulation of the Protective Antigen Gene of *Bacillus anthracis*", *Inf. Immun.* 57(8):2295–2300 (Aug. 1989).

Iacono–Connors et al, "Protection against Anthrax with Recombinant Virus Expressed Protective Antigen . . . ", *Inf. Immun.* 59(6):1961–1965 (Jun. 1991).

Cataldi et al, "Regulation of pag gene expression in *Bacillus anthracis* . . . " *FEMS Microbiol. Lett.* 98:89–94 (Nov. 1992).

Walz et al, "Sequential effects of ILZ–diphtheria toxin fusion protein on T–cell activation", *PNAS* 86: 9485–9488 (Dec. 1989).

Arora et al. *J. Bio. Chem.* 267(22):15542–15548, 1992.

Arora and Leppla Abstract:*ASM Annual Meeting*, New Orleans, LA, May 1992, p. 31, #B–33.

Arora et al. Abstract:*Third Internatl. Sympos. on Immunotoxins*, Orlando, FL, Jun. 19–21, 1992.

Quinn et al. *J. Bio. Chem.* 266(30):20124–20130, 1991.

Oeltmann and Frankel *News* 5:2334–2337, Jul. 1991.

Singh et al. *J. Bio. Chem.* 266(23):15493–15497, 1991.

Singh et al. *J. Bio. Chem.* 264(32):19103–19107, 1989.

Leppla et al. Abstract:*Fifth European Workshop on Bacterial Protein Toxins* Veldhoven, Jun. 30–Jul. 5, 1991.

Klimpel et al. Abstract:*1992 ASM General Meeting*, New Orleans, LA, May 1992, p. 31, #B–32.

*Primary Examiner*—Stephen G. Walsh
*Attorney, Agent, or Firm*—Townsend and Townsend and Crew

[57] ABSTRACT

The present invention provides a nucleic acid encoding a fusion protein, comprising a nucleotide sequence encoding the protective antigen (PA) binding domain of the native lethal factor (LF) protein and a nucleotide sequence encoding an activity inducing domain of a second protein. Also provided is a nucleic acid encoding a fusion protein, comprising a nucleotide sequence encoding the translocation domain and LF binding domain of the native PA protein and a nucleotide sequence encoding a ligand domain which specifically binds a cellular target. Proteins encoded by the nucleic acid of the invention, vectors comprising the nucleic acids and hosts capable of expressing the protein encoded by the nucleic acids are also provided. A composition comprising the PA binding domain of the native LF protein chemically attached to a non-LF activity inducing moiety is further provided. A method for delivering an activity to a cell is provided. The steps of the method include administering to the cell a protein comprising the translocation domain and the LF binding domain of the native PA protein and a ligand domain, and administering to the cell a product comprising the PA binding domain of the native LF protein and a non-LF activity inducing moiety, whereby the product administered is internalized into the cell and performs the activity within the cell.

13 Claims, No Drawings

ANTHRAX TOXIN FUSION PROTEINS, NUCLEIC ACID ENCODING SAME

BACKGROUND OF THE INVENTION

The targeting of cytotoxic or other moieties to specific cell types has been proposed as a method of treating diseases such as cancer. Various toxins including Diphtheria toxin and Pseudomonas exotoxin A have been suggested as potential candidate toxins for this type of treatment. A difficulty of such methods has been the inability to selectively target specific cell types for the delivery of toxins or other active moieties.

Anthrax toxin is composed of three separate proteins produced by *Bacillus anthracis:* lethal factor (LF) (SEQ ID NOS: 1 and 2), edema factor (EF), and protective antigen (PA) (SEQ ID NOS: 3 and 4) (Leppla, S. H. Alouf, J. E. and Freer, J. H., eds. *Sourcebook of Bacterial Toxins* Academic Press, London 277–302, 1991). The three proteins are individually nontoxic, and become toxic only when administered in pairwise combinations. PA (83 kDa) binds to a specific cell receptor and is then cleaved by a cell surface protease which releases an amino-terminal 19-kDa fragment (Singh et al. *J. Biol. Chem.* 264:19103–19107, 1989). Removal of this fragment from PA exposes a high-affinity binding site for LF and EF on the receptor-bound 63-kDa carboxyl-terminal fragment (PA63). The complex of PA63 and LF or EF enters cells and probably passes through acidified endosomes to reach the cytosol.

The genes for each of the three anthrax toxin components have been cloned and sequenced. This showed that LF and EF have extensive homology in amino acid residues 1–300. Since LF and EF compete for binding to PA63, it is highly likely that these amino-terminal regions are responsible for binding to PA63. Direct evidence for this was provided in a recent mutagenesis study (Quinn et al. *J. Biol. Chem.* 266:20124–20130, 1991); all mutations made within amino acid residues 1–210 of LF led to decreased binding to PA63. The same study also suggested that the putative catalytic domain of LF included residues 491–776 (Quinn et al., 1991). In contrast, the location of functional domains within the PA63 polypeptide is not obvious from inspection of the deduced amino acid sequence. However, studies with monoclonal antibodies and protease fragments (Leppla, 1991) and subsequent mutagenesis studies (Singh et al. *J. Biol. Chem.* 266:15493–15497, 1991) showed that residues at and near the carboxyl terminus of PA are involved in binding to receptor.

Prior work had shown that the carboxyl terminal PA fragment (PA63) can form ion conductive channels in artificial lipid membranes (Blaustein et al. *Proc. Natl. Acad. Sci. U.S.A.* 86:2209–2213, 1989; Koehler, T. M. and Collier, R. J. *Mol. Microbiol.* 5:1501–1506, 1991), and that LF bound to PA63 on cell surface receptors can be artificially translocated across the plasma membrane to the cytosol by acidification of the culture medium (Friedlander, A. M. *J. Biol. Chem.* 261:7123–7126, 1986). Furthermore, drugs that block endosome acidification protect cells from LF (Gordon et al. *J. Biol. Chem.* 264:14792–14796, 1989; Friedlander, 1986; Gordon et al. *Infect. Immun.* 56:1066–1069, 1988). The mechanisms by which EF is internalized have been studied in cultured cells by measuring the increases in cAMP concentrations induced by PA and EF (Leppla, S. H. *Proc. Natl. Acad. Sci. U.S.A.* 79:3162–3166, 1982; Gordon et al., 1989). However, because assays of cAMP are relatively expensive and not highly precise, this is not a convenient method of analysis. Internalization of LF has been analyzed only in mouse and rat macrophages, because these are the only cell types lysed by the lethal toxin.

Pseudomonas exotoxin A (PE) is a toxin for which a detailed analysis of functional domains exists. The sequence is deposited with GenBank. Structural determination by X-ray diffraction, expression of deleted proteins, and extensive mutagenesis studies have defined three functional domains in PE: a receptor-binding domain (residues 1–252 and 365–399) designated Ia and Ib, a central translocation domain (amino acids 253–364, domain II), and a carboxyl-terminal enzymatic domain (amino acids 400–613, domain III). Domain III catalyzes the ADP-ribosylation of elongation factor 2 (EF-2), which results in inhibition of protein synthesis and cell death. Recently it was also found that an extreme carboxyl terminal sequence is essential for toxicity (Chaudhary et al. *Proc. Natl. Acad. Sci. U.S.A.* 87:308–312, 1990; Seetharam et al. *J. Biol. Chem.* 266:17376–17381, 1991). Since this sequence is similar to the sequence that specifies retention of proteins in the endoplasmic reticulum (ER) (Munro, S. and Pelham, H. R. B. *Cell* 48:899–907, 1987), it was suggested that PE must pass through the ER to gain access to the cytosol. Detailed knowledge of the structure of PE has facilitated use of domains II, Ib, and III (together designated PE40) in hybrid toxins and immunotoxins.

A single-chain antibody (sFv) consists of an antibody light chain variable domain ($V_L$) and heavy chain variable domain ($V_H$), connected by a short peptide linker which allows the structure to assume a conformation capable of binding to antigen. In a diagnostic or therapeutic setting, the use of an sFv may offer attractive advantages over the use of a monoclonal antibody (MoAb). Such advantages include more rapid tumor penetration with concomitantly low retention in non-targeted organs (Yokota et al. *Cancer Res* 52:3402.1992), extremely rapid plasma and whole body clearance (resulting in high tumor to normal tissue partitioning) in the course of imaging studies (Colcher et al. *Natl. Cancer Inst.* 82:1191,1990; Milenic et al. *Cancer Res.* 51:6363, 1991), and relatively low cost of production and ease of manipulation at the genetic level (Huston et al. *Methods Enzymol.* 203:46, 1991; Johnson, S. and Bird, R. E. *Methods Enzymol.* 203:88, 1991). In addition, sFv-toxin fusion proteins have been shown to exhibit enhanced antitumor activity in comparison with conventional chemically cross-linked conjugates (Chaudhary et al. *Nature* 339:394, 1989; Batra et al. *Cell. Biol.* 11:2200–2295, 1991). Among the first sFv to be generated were molecules capable of binding haptens (Bird et al. *Science* 242:423, 1988; Huston et l. *Proc. Natl. Acad. Sci. USA* 85:5879, 1988), cell-surface receptors (Chaudhary et al., 1989), and tumor antigens (Chaudhary et al. *Proc. Natl. Acad. Sci. USA* 87:1066, 1990; Colcher et al., 1990).

The gene encoding an sFv may be assembled in one of two ways: (i) by de novo construction from chemically synthesized overlapping oligonucleotides, or (ii) by polymerase chain reaction (PCR)-based cloning of $V_L$ and $V_H$ genes from hybridoma cDNA. The main disadvantages of the first approach are the considerable expense involved in oligonucleotide synthesis, and the fact that the sequence of $V_L$ and $V_H$ must be known before gene assembly is possible. Consequently, the majority of the sFv reported to date were generated by cloning from hybridoma cDNA; nevertheless, this approach also has inherent disadvantages, because it requires availability of the parent hybridoma or myeloma cell line, and problems are often encountered when attempting to retrieve the correct V region genes from heterologous cDNA. For example, hybridomas in which the immortalizing fusion partner is derived from MOPC-21 may express a $V_L$ kappa transcript which is aberrantly rearranged at the VJ recombination site, and which therefore encodes a non-functional light chain (Cabilly & Riggs, 1985; Carroll et al., 1988). Cellular levels of this transcript may exceed that generated from the productive $V_L$ gene, so that a large proportion of the product on PCR amplification of hybridoma cDNA will not encode a functional light chain. A second disadvantage of the PCR-based method, frequently encountered by the inventors, is the variable success of recovering $V_H$ genes using the conditions so far reported in the literature, presumably because the number of mismatches between primers and the target sequence destabilizes the hybrid to an extent which inhibits PCR amplification.

One method of targeting specific cells has been to make fusion proteins of a toxin and a single chain antibody. Such methods have been difficult to practice because of the difficulties in obtaining single chain antibodies and other targeting moieties. Also, none of the proposed treatment methods has been fully successful, because of the need to fuse the toxin to the targeting moiety, thus disrupting either the toxin function or the targeting function.

Thus, there exists a need for a method of providing a target cell population with a particular activity to treat tumors and other diseases.

SUMMARY OF THE INVENTION

The present invention provides a nucleic acid encoding a fusion protein, comprising a nucleotide sequence encoding the PA binding domain of the native LF protein and a nucleotide sequence encoding an activity inducing domain of a second protein. Also provided is a nucleic acid encoding a fusion protein, comprising a nucleotide sequence encoding the translocation domain and LF binding domain of the native PA protein and a nucleotide sequence encoding a ligand domain which specifically binds a cellular target. Proteins encoded by the nucleic acid of the invention, vectors comprising the nucleic acids and hosts capable of expressing the protein encoded by the nucleic acids are also provided.

A composition comprising the PA binding domain of the native LF protein chemically attached to an activity inducing moiety is further provided.

Finally, a method for delivering an activity to a cell is provided. The steps of the method include administering to the cell (a) a protein comprising the translocation domain and the LF binding domain of the native PA protein and a ligand domain and (b) a product comprising the PA binding domain of the native LF protein and a non-LF activity inducing moiety, whereby the product administered in step (b) is internalized into the cell and performs the activity within the cell.

DETAILED DESCRIPTION OF THE INVENTION

Nucleic Acids

Lethal Factor (LF)

The present invention provides an isolated nucleic acid encoding a fusion protein, comprising a nucleotide sequence encoding the PA binding domain of the native LF protein and a nucleotide sequence encoding an activity inducing domain of a second protein. The LF gene and native LF protein are shown in SEQ ID NO: 1.

The second protein can be a toxin, for example Pseudomonas exotoxin A, the A chain of Diphtheria toxin or shiga toxin. The activity inducing domains of numerous other known toxins can be included in the fusion protein encoded by the present nucleic acid. The activity inducing domain need not be a toxin, but can have other activities, including but not limited to stimulating or reducing growth, selectively inhibiting DNA replication, providing enzymatic activity or providing a source of radiation. In any case, the fusion proteins encoded by the nucleic acids of the present invention must be capable of being internalized and capable of expressing the specified activity in a cell. A given LF fusion protein of the present invention can be tested for its ability to be internalized and to express the desired activity using methods as described herein, particularly in Examples 1 and 2.

An example of a nucleic acid of the invention comprises the nucleotide sequence defined in the Sequence Listing as SEQ ID NO: 5. This nucleic acid encodes a fusion of LF residues 1–254 with the two-residue linker "TR" and PE residues 401–602 (SEQ ID NO: 6). The protein includes a Met-Val-Pro- sequence at the begining of the LF sequence. Means for obtaining this fusion protein are further described below and in Example 1.

A further example of a nucleic acid of this invention comprises the nucleotide sequence defined in the Sequence Listing as SEQ ID NO: 7. This nucleic acid encodes a fusion of LF residues 1–254 with the two-residue linker "TR" and PE residues 398–613. (SEQ ID NO: 8) The junction point containing the "TR" is the sequence LTRA and the Met-Val-Pro- is also present. This fusion protein and methods for obtaining it are further described below and in Example 2.

Another example of the nucleic acid of the present invention comprises the nucleotide sequence defined in the Sequence Listing as SEQ ID NO: 9. This nucleic acid encodes a fusion of LF residues 1–254 with the two residue linker and PE residues 362–613. (SEQ ID NO: 10) This fusion protein is further described in Example 1.

Alternatively, the nucleic acid can include the entire coding sequence for the LF protein fused to a non-LF activity inducing domain. Other LF fusion proteins of various sizes and methods of making and testing them for the desired activity are also provided herein, particularly in Examples 1 and 2.

Protective Antigen (PA)

Also provided is an isolated nucleic acid encoding a fusion protein, comprising a nucleotide sequence encoding the translocation domain and LF binding domain of the native PA protein and a nucleotide sequence encoding a ligand domain which specifically binds a cellular target.

An example of a nucleic acid of this invention comprises the nucleotide sequence defined in the Sequence Listing as SEQ ID NO:11. This nucleic acid encodes a fusion of PA residues 1–725 and human CD4 residues 1–178, the portion which binds to gp120 exposed on HIV-1 infected cells (SEQ ID NO:12). This fusion protein and methods for obtaining and testing fusion proteins are further described below and in Examples 3, 4 and 5.

The PA fusion protein encoding nucleic acid provided can encode any ligand domain that specifically binds a cellular target, e.g. a cell surface receptor, an antigen expressed on the cell surface, etc. For example the nucleic acid can encode a ligand domain that specifically binds to an HIV protein expressed on the surface of an HIV-infected cell. Such a ligand domain can be a single chain antibody encoded on a fusion protein as provided above and in Examples 3, 4 and 5. Alternatively, the nucleic acid can encode, for example, a ligand domain that is a growth factor, as provided in Example 3.

Although the PA encoding sequence of the nucleic acid encoding the PA fusion proteins of this invention need only include the nucleotide sequence encoding the translocation domain and LF binding domain of the native PA protein, the nucleic acid can further comprise the nucleotide sequence encoding the remainder of the native PA protein. Any sequences to be included beyond those required, can be determined based on routine considerations such as ease of manipulation of the nucleic acid, ease of expression of the product in the host, and any effect on translocation/internalization as taught in the examples.

Proteins

Proteins encoded by the nucleic acids of the present invention are also provided. Only active proteins are included within the scope of the invention.

LF Fusion Proteins

The present invention provides LF fusion proteins encoded by the nucleic acids of the invention as described above and in the examples. Specifically, fusions of the LF gene with domains II, Ib, and III of PE can be made by recombinant methods to produce in-frame translational fusions. Recombinant genes (e.g., SEQ ID NOs: 5, 7 and 9) were expressed in *Escherichia coli* (*E. coli*), and the purified proteins were tested for activity on cultured cells as provided in Examples 1 and 2. Certain fusion proteins are efficiently internalized via the PA receptor to the cytosol. These examples demonstrate that this system can be used to deliver many different polypeptides into targeted cells.

Although specific examples of these proteins are provided, given the present teachings regarding the preparation of LF fusion proteins, other embodiments having other activity inducing domains can be practiced using routine skill.

Using current methods of genetic manipulation, a variety of other active including moieties (e.g., polypeptides) can be translated as fusion proteins with LF which in turn can be internalized by cells when administered with PA or PA fusion proteins. Fusion proteins generated by this method can be screened for the desired activity using the methods set forth in the Examples and by various routine procedures. Based on the data presented here, the present invention provides a highly effective system for delivery of an activity inducing moiety into cells.

PA fusion proteins

The present invention provides PA fusion proteins encoded by the nucleic acids of the invention. Specifically fusions of PA with single chain antibodies and CD4 are provided.

Using current methods of genetic manipulation, a variety of other ligand domains (e.g.,polypeptides) can be translated as fusion proteins with PA which in turn can specifically target cells and facilitate internalization LF or LF fusion proteins. Based on the data presented here, the present invention provides a highly effective system for delivery of an activity inducing moiety into a particular type or class of cells.

Although specific examples of these proteins are provided, given the present teachings regarding the preparation of PA fusion proteins, other embodiments having other ligand domains can be practiced using routine skill. The fusion proteins generated can be screened for the desired specificity and activity utilizing the methods set forth in the example and by various routine procedures. In any case, the PA fusion proteins encoded by the nucleic acids of the present invention must be able to specifically bind the selected target cell, bind LF or LF fusions or conjugates and internalize the LF fusion/conjugate.

Conjugates

A composition comprising the PA binding domain of the native LF protein chemically attached to an activity inducing moiety is provided. Such an activity inducing moiety is an activity not present on native LF. The composition can comprise an activity inducing moiety that is, for example, a polypeptide, a radioisotope, an antisense nucleic acid or a nucleic acid encoding a desired gene product.

Using current methods of chemical manipulation, a variety of other moieties (e.g., polypeptides, nucleic acids, radioisotopes, etc.) can be chemically attached to LF and can be internalized into cells and can express their activity when administered with PA or PA fusion proteins. The compounds can be tested for the desired activity and internalization following the methods set forth in the Examples. For example, the present invention provides an LF protein fragment 1–254 (LF1–254) with a cysteine residue added at the end of LF1–254 (LF1–254Cys). Since there are no other cysteines in LF, this single cysteine provides a convenient attachment point through which to chemically conjugate other proteins or non-protein moieties.

Vectors and Hosts

A vector comprising the nucleic acids of the present invention is also provided. The vectors of the invention can be in a host capable of expressing the protein encoded by the nucleic acid.

There are numerous *E. coli* expression vectors known to one of ordinary skill in the art useful for the expression of the antigen. Other microbial hosts suitable for use include bacilli, such as *Bacillus subtilus,* and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Host bacterial cells can be chosen that are mutated to be reduced in or free of proteases, so that the proteins produced are not degraded. For bacillus expression systems in which the proteins are secreted into the culture medium, strains are available that are deficient in secreted proteases.

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Treatment Methods

A method for delivering a desired activity to a cell is provided. The steps of the method include administering to the cell (a) a protein comprising the translocation domain and the LF binding domain of the native PA protein and a ligand domain, and (b) a product comprising the PA binding domain of the native LF protein and a non-LF activity inducing moiety, whereby the product administered in step (b). is internalized into the cell and performs the activity within the cell.

The method of delivering an activity to a cell can use a ligand domain that is the receptor binding domain of the native PA protein. Other ligand domains are selected for their specificity for a particular cell type or class of cells. The specificity of the PA fusion protein for the targeted cell can be determined using standard methods and as described in Examples 2 and 3.

The method of delivering an activity to a cell can use an activity inducing moiety that is a polypeptide, for example a growth factor, a toxin an antisense nucleic acid or a nucleic acid encoding a desired gene product. The actual activity inducing moiety used will be selected based on its functional characteristics, e.g. its activity.

A method of killing a tumor cell in a subject is also provided. The steps of the method can include administering to the subject a first fusion protein comprising the translocation domain and LF binding domain of the native PA protein and a tumor cell specific ligand domain in an amount sufficient to bind to a tumor cell. A second fusion protein is also administered wherein the protein comprises the PA binding domain of the native LF protein and a cytotoxic domain of a non-LF protein in an amount sufficient to bind to the first protein, whereby the second protein is internalized into the tumor cell and kills the tumor cell.

The cytotoxic domain can be a toxin or it can be another moiety not strictly defined as a toxin, but which has an activity that results in cell death. These cytotoxic moieties can be selected using standard tests of cytotoxicity, such as the cell lysis and protein synthesis inhibition assays described in the examples.

The invention further provides a method of killing HIV-infected cells in a subject comprising the steps of administering to the subject a first fusion protein comprising the translocation domain and LF binding domain of the native PA protein and a ligand domain that specifically binds to an HIV protein expressed on the surface of an HIV-infected cell in an amount sufficient to bind to an HIV-infected cell and administering to the subject a second fusion protein comprising the PA binding domain of the native LF protein and a cytotoxic domain of a non-LF protein in an amount sufficient to bind to the first protein, whereby the second protein is internalized into the HIV-infected cell and kills the HIV-infected cell thereby preventing propagation of HIV.

Although certain of the methods of the invention have been described as using LF fusion proteins, it will be understood that other LF compositions having chemically attached activity inducing moieties can be used in the methods.

The fusion proteins and other compositions of the inventions may be administered by various methods, e.g., parenterally, intramuscularly or intrapertioneally.

The amount necessary can be deduced from other receptor/ligand or antibody/antigen therapies. The amount can be optimized by routine procedures. The exact amount of such LF and PA compositions required will vary from subject to subject, depending on the species, age, weight and general condition of the subject, the severity of the disease that is being treated, the particular fusion protein of composition used, its mode of administration, and the like. Generally, dosage will approximate that which is typical for the administration of cell surface receptor ligands, and will preferably be in the range of about 2 µg/kg/day to 2 mg/kg/day.

Depending on the intended mode of administration, the compounds of the present invention can be in various pharmaceutical compositions. The compositions will include, as noted above, an effective amount of the selected protein in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the fusion protein or other composition without causing any undesirable biological effects or interacting in a deleterious manner with any of the other components of the pharmaceutical composition in which it is contained.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The following examples are intended to illustrate, but not limit, the invention. While they are typical of those that might be used, other procedures known to those skilled in the art may be alternatively employed.

EXAMPLE 1

Fusions of Anthrax Toxin Lethal Factor to the ADP-Ribosylation Domain of Pseudomonas Exotoxin Reagents and General Procedures Restriction endonucleases and DNA modifying enzymes were purchased from GIBCO/BRL, Boehringer Mannheim, or New England Biolabs. Low melting point agarose (Sea Plaque) was obtained from FMC Corp. (Rockland, Me.). Oligonucleotides were synthesized on a PCR Mate (Applied Biosystems) and purified on oligonucleotide purification cartridges (Applied Biosystems). The PCR was performed with a DNA amplification reagent (GeneAmp) from Perkin-Elmer Cetus Instruments and a thermal cycler (Perkin-Elmer Cetus). The amplification involved denaturation at 94° C. for 1 min, annealing at 55° C. for 2.5 min and extension at 72° C. for 3 min, for 30 cycles. A final extension was run at 72° C. for 7 min. For amplification of PE fragments, 10% formamide was added in the reaction mixture to decrease the effect of high GC content. DNA sequencing reactions were done using the Sequenase version 1.0 from U.S. Biochemical Corp. and DNA sequencing gels were made from Gel Mix 6 from GIBCO/BRL. [$^{35}$S]deoxyadenosine 5'-[α-thio] triphosphate and L-[3,4,5-$^3$H]leucine were purchased from Dupont-New England Nuclear. J774A.1 cells were obtained from American Type Culture Collection. Chinese Hamster Ovary (CHO) cells were obtained from Michael Gottesman (National Cancer Institute, National Institutes of Health) (ATCC CCL 61).

Plasmid Construction

Construction of plasmids containing LF-PE fusions—Varying portions of the PE gene were amplified by PCR, ligated in frame to the 3'end of the LF gene, and inserted into the pVEX115 f+T expression vector (provided by V. K. Chaudhary, National Cancer Institute, National Institutes of Health). To construct fusion proteins, the 3'-end of the native LF gene (including codon 776 of the mature protein, specifying Ser) was ligated with the 5'-ends of sequences specifying varying portions of domains II, Ib, and III of PE. The LF gene was amplified from the plasmid pLF7 (Robertson, D. L. and Leppla, S. H. *Gene* 44:71–78, 1986) by PCR using oligonucleotide primers which added KpnI and MluI sites at the 5' and the 3' ends of the gene, respectively. Similarly, varying portions of the PE gene (provided by David FitzGerald, National Cancer Institute, National Institutes of Health) were amplified by PCR so as to add MluI and EcoRI sites at the 5' and 3' ends. The PCR product of the LF gene was digested with KpnI and the DNA was precipitated. The LF gene was subsequently treated with MluI. Similarly, the PCR products of PE amplification were digested with MluI and EcoRI. The expression vector pVEX115 f+T was cleaved with KpnI and EcoRI separately and dephosphorylated. This vector has a T7 promoter, OmpA signal sequence, multiple cloning site, and T7 transcription terminator. All the above DNA fragments were purified from low-melting point agarose, a three-fragment ligation was carried out, and the product transformed into *E. coli* DH5α (ATCC 53868). The four constructs described in this report have the entire LF gene fused to varying portions of PE. The identity of each construct was confirmed by sequencing the junction point using a Sequenase kit (U.S. Biochemical Corp.). For expression, recombinant plasmids were transformed into *E. coli* strain SA2821 (provided by Sankar Adhya, National Cancer Institute, National Institutes of Health, which is a derivative of BL21(λDE3) (Studier, F. W. and Moffatt, B. A. *J. Mol. Biol.* 189:113–150, 1986). This strain has the T7 RNA polymerase gene under control of an inducible lac promotor and also contains the degP mutation, which eliminates a major periplasmic protease (Strauch et al. *J. Bacteriol.* 171:2689–2696, 1989).

In the resulting plasmids, the LF-PE fusion genes are under control of the T7 promoter and contain an OmpA signal peptide to obtain secretion of the products to the periplasm so as to facilitate purification. The design of the PCR linkers also led to insertion of two non-native amino acids, Thr-Arg, at the LF-PE junction. The four fusions analyzed in this report contain the entire 776 amino acids of mature LF, the two added residues TR (Thr-Arg), and varying portions of PE. In fusion FP33, the carboxyl-terminal end of PE was changed from the native REDLK (Arg-Glu-Asp-Leu-Lys) to LDER, a sequence that fails to cause retention in the ER (endoplasmic reticulum) (32).

Expression and Purification of Fusion Proteins

Fusion proteins produced from pNA2, pNA4, pNA23 and pNA33 were designated FP2, FP4, FP23 and FP33 respectively. *E. coli* strains carrying the recombinant plasmids were grown in super broth (32 g/L Tryptone, 20 g/L yeast extract, 5 g/L NaCl, pH 7.5) with 100 μg/ml of ampicillin with shaking at 225 rpm at 37° C., in 2-L cultures. When $A_{600}$ reached 0.8–1.0, isopropyl-1-thio-β-D-galactopyranoside was added to a final concentration of 1 mM, and cultures were incubated an additional 2 hr. EDTA and 1,10-o-phenanthroline were added to 5 mM and 0.1 mM respectively, and the bacteria were harvested by centrifugation at 4000×g for 15 min at 4° C. For extraction of the periplasmic contents, cells were suspended in 75 ml of 20% sucrose containing 30 mM Tris and 1 mM EDTA, incubated at 0° for 10 min, and centrifuged at 8000×g for 15 min at 4° C. Cells were resuspended gently in 50 ml of cold distilled water, kept on ice for 10 min, and the spheroplasts were pelleted. The supernatant was concentrated with Centriprep-100 units (Amicon) and loaded on a Sephacryl S-200 column (40×2 cm) and 1 ml fractions were collected.

Fractions having full length fusion protein as determined by immunoblots were pooled and concentrated as above. Protein was then purified on an anion exchange column (MonoQ HR5/5, Pharmacia-LKB) using a NaCl gradient. The fusion proteins eluted at 280–300 mM NaCl. The proteins were concentrated again on Centriprep-100 (Amicon Division) and the MonoQ chromatography was repeated. Protein concentrations were determined by the bicinchoninic acid method (BCA Protein Assay Reagent, Pierce), using bovine serum albumin as the standard. Proteins were analyzed by polyacrylamide gel electrophoresis in the presence of sodium dodecyl sulfate (SDS). Gels were either stained with Coomassie Brilliant Blue or the proteins were electroblotted to nitrocellulose paper which was probed with polyclonal rabbit antisera to LF or PE (List Biological Laboratories, Campbell, Calif.). To determine the percent of full length protein, SDS gels stained with Coomassie Brilliant Blue were scanned with a laser densitometer (Pharmacia-LKB Ultrascan XL).

The proteins migrated during gel electrophoresis with molecular masses of more than 106 kDa, consistent with the expected sizes, and immunoblots confirmed that the products had reactivity with antisera to both LF and PE. The fusion proteins differed in their susceptibility to proteolysis as judged by the appearance of smaller fragments on immunoblots, and this led to varying yields of final product. Thus, from 2-L cultures the yields were FP2, 27 μg; FP4, 87 μg; FP23, 18 μg; and FP33, 143 μg.

Cell Culture Techniques and Protein Synthesis Inhibition Assay

CHO cells were maintained as monolayers in Eagle's minimum essential medium (EMEM) supplemented with 10% fetal bovine serum, 10 mM 4-2(2-hydroxyethyl)-1- piperazineethanesulfonic acid (HEPES) (pH 7.3), 2 mM glutamine, penicillin/streptomycin, and non-essential amino acids (GIBCO/BRL). Cells were plated in 24- or 48-well dishes one day before the experiment. After overnight incubation, the medium was replaced with fresh medium containing 1 µg/ml of PA unless otherwise indicated. Fusion proteins were added to 0.1–1000 ng/ml. All data points were done in duplicate. Cells were further incubated for 20 hr at 37° C. in 5% $CO_2$ atmosphere. The medium was then aspirated and cells were incubated for hr at 37° C. with leucine-free medium containing 1 µCi/ml [$^3$H]leucine. Cells were washed twice with medium, cold 10% trichloroacetic acid was added for 30 min, the cells were washed twice with 5% trichloroacetic acid and dissolved in 0.150 ml 0.1M NaOH. Samples were counted in Pharmacia-LKB 1410 liquid scintillation counter. In experiments to determine if the toxin is internalized through acidified endosomes, 1 µM monensin (Sigma) was added 90 min prior to toxin and was present during all subsequent steps. To verify that the fusion proteins were internalized through the PA receptor, competition with native LF was carried out. PA (0.1 µg/ml) and LF (0.1–10,000 ng/ml) were added to the CHO cells to block the PA receptor and the fusion proteins were added thereafter at concentrations of 100 ng/ml for FP4 and FP23 and 5 ng/ml for FP33. Protein synthesis inhibition was measured after 20 hr as described above.

Cytotoxic Activity of the Fusion Proteins

All four fusion proteins made and purified were toxic to CHO cells. The concentration causing 50% lysis of cultured cells ($EC_{50}$) values of the proteins were 350, 8, 10, and 0.2 ng/ml for FP2, FP4, FP23 and FP33 respectively (Table 1). These assays were done with PA present at 1 ug/ml, exceeding the $K_m$ of 0.1 ug/ml (100 pM). The fusion proteins had no toxicity even at 1 µg/ml when PA was omitted, proving that internalization of the fusion proteins was occurring through the action of PA and the PA receptor. Native LF has previously been shown to have no short-term toxic effects on CHO cells when added with PA, and therefore was not included in these assays. The fusion protein having only domain III and an altered carboxyl-terminus (FP33) was most active, whereas the one having the intact domains II and III and the native REDLK terminus (FP2) was least active. The other two fusion proteins (FP4 and FP23) had intermediate potencies.

Among proteins having ADP-ribosylation activity, potencies equalling or exceeding 1 pM have previously been found only for native diphtheria and Pseudomonas toxins acting on selected cells (Middlebrook, J. L. and Dorlan, R. B. *Can. J. Microbiol.* 23:183–189, 1977) and for fusion proteins of PE and diphtheria toxin when tested on cells containing >100,000 receptors for the ligand-recognition domain of the fusion (EGF, transferrin, etc.) (Pastan, I. and FitzGerald, D. *Science* 254:1173–1177, 1991; Middlebrook, et al. 1977). For CHO cells, the potency of FP33 ($EC_{50}$=2 pM) is higher than that of PE itself ($EC_{50}$=420 pM), even though CHO cells probably have similar numbers of receptors for both PA and PE (approx. 5,000–20,000). If the intracellular trafficking of native PE delivers less than 5% of the molecules to the cytosol, then the 200-fold greater potency of FP33 suggests that the PA/LF system has an inherently high efficiency of delivery to the cytosol.

A comparison of the potencies of the four fusion proteins shows that inclusion of domain II decreases potency. Thus, the fusion with the lowest potency, FP2, was the one containing intact domains II, Ib, and III. In designing the fusion proteins, all or part of PE domain II and Ib was included in several of the constructs because it could not be assumed that the translocation functions possessed by PA and LF would be able to correctly traffick PE domain III to the cytosol. The combination of domains II, Ib, and III, termed PE40, has been used in a large number of toxic hybrid proteins, by fusion to growth factors, monoclonal antibodies, and other proteins (Pastan et al. 1991; Oeltmann, T. N. and Frankel, A. E. *Faseb J.* 5:2334–2337, 1991), and some of these fusions have shown substantial potency. Domain II was found to be essential in these hybrid proteins to provide a translocation function not present in the receptor-binding domain to which it was fused. The potency of many of these PE40 fusion proteins appears to require that they be trafficked through the Golgi and ER and proteolytically activated in the same manner as native PE, so as to achieve delivery of domain III to the cytosol. The fact that inclusion of the entire domain II in the LF fusion protein FP2 instead decreased activity suggests that internalization of the LF fusions occurs through a different route, one that does not easily accommodate all the sequences in domain II.

Evidence that structures within PE residues 251–278 inhibit translocation of the LF fusions comes from the 35-fold lower potency of FP2 compared to FP23. One structure that might inhibit translocation of the fusions is the disulfide loop formed by Cys265 and Cys287. In native PE, this disulfide loop appears to be required for maximum activity. Thus, native PE and TGF-α-PE40 fusions become 10- to 100-fold less toxic if one or both these cysteines are changed to serine. The disulfide loop probably acts to constrain the polypeptide so that Arg276 and Arg279 are susceptible to the intracellular protease involved in the cleavage that precedes translocation. In contrast, the disulfide loop decreases the potency of the LF fusions, perhaps by preventing the unfolding needed for passage through a protein channel, thereby acting in this situation as a "stop transfer" sequence. FP23, which lacks Cys265, would not contain the domain II disulfide, and therefore would not be subject to this effect. LF, like PA and EF, contains no cysteines, and would not be prevented by disulfide loops from the complete unfolding needed to pass through a protein channel. The suggestion that disulfide loops act as stop-transfer signals would predict that the disulfide Cys372–Cys379 in PE domain Ib, which is retained in all four LF fusions would also decrease potency. It should be noted that neither the fusions made here nor the PE40 fusions have been analyzed chemically to determine if the disulfides in domains II and III are actually formed. If the disulfides do form correctly, it would be predicted that the potencies of all of the fusion proteins, and especially that of FP2, would be increased by treatment with reducing agents. These analyses have not yet been performed. This analysis also suggests that future LF fusions might be made more potent by omission of domain Ib.

The other structural feature of PE known to affect intracellular trafficking is the carboxyl terminal sequence, REDLK, that specifies retention in the ER (Chaudhary et al. 1990; Muro et al. 1987). To determine if the trafficking of the LF fusion proteins was similar to that of PE, two of the fusion proteins were designed so as to differ only in the terminal sequence. Replacement of the native sequence by LDER, one that does not function as an ER retention signal, produced the most toxic of the four fusion proteins, FP33. FP4, identical except that it retained a functional REDLK sequence, was 30-fold less potent. These data suggest that sequestration of the REDLK-ended fusions decreased their access to cytosolic EF-2. The implication is that PE may require the REDLK terminus to be delivered to the ER for an obligatory processing step, but then be limited in its final toxic potential by sequestration from its cytosolic target. Finally, this comparison strongly argues that internalization of the LF fusions does not follow the same path as PE.

In designing the fusion proteins described here it was hoped that they would have cytotoxic activity against cells that are unaffected by anthrax lethal toxin, and this was successfully realized as shown by the data obtained with CHO cells. However, prior knowledge about LF did not provide a basis for predicting whether the constructs would retain toxicity toward mouse macrophages, the only cells known to be rapidly killed by anthrax lethal toxin. Macrophages are lysed by lethal toxin in 90–120 minutes, long before any inhibition of protein synthesis resulting from ADP-ribosylation of EF-2 leads to decreases in membrane integrity or viability. This kinetic difference made it possible to test directly for LF action. As discussed above, the fusion proteins purified to remove the ≈89-kDa LF species formed by proteolysis were not toxic to J774A.1 macrophages. This shows that attachment of a bulky group to the carboxyl terminus of LF eliminates its normal toxic activity. In the absence of any assay for the putative catalytic activity of LF, it is not possible to determine the cause of the loss of LF activity. The inability of the fusions to lyse J774A.1 cells also argues against proteolytic degradation of the fusions either in the medium during incubation with cells or after internalization.

An important result of the invention described here is the demonstration that the anthrax toxin proteins constitute an efficient mechanism for protein internalization into animal cells. The high potency of the present fusion proteins argues that this system is inherently efficient, as well as being amenable to improvement. The high efficiency results in part from the apparent direct translocation from the endosome, without a requirement for trafficking through other intracellular compartments. In addition to its efficiency, the system appears able to tolerate heterologous polypeptides.

Macrophage Lysis Assay of Fusion Proteins

Fusion proteins were assayed for LF functional activity on J774A.1 macrophage cell line in the presence of 1 µg/ml PA. One day prior to use, cells were scraped from flasks and plated in 48-well tissue culture dishes. For cytotoxicity tests, the medium was aspirated and replaced with fresh medium containing 1 µg/ml PA and the LF fusion proteins, and the cells were incubated for 3 hr. All data points were performed in duplicate. To measure the viability of the treated cells, 3-[4,5-dimethylthiazol-2-yl]-2,5-diphenyltetrazolium bromide (MTT) was added to the cells to a final concentration of 0.5 mg/ml, and incubation was continued for an additional 45 min to allow the uptake and oxidation of MTT by viable cells. Medium was aspirated and replaced by 200 µl of 0.5% SDS, 40 mM HCl, 90% isopropanol and the plates were vortexed to dissolve the blue pigment. The MTT absorption was read at 570 nm using a UVmax Kinetic Microplate Reader (Molecular Devices Corp.).

The crude periplasmic extracts from which the fusion proteins were purified caused lysis of J774A.1 macrophages when added with PA, indicating the presence of active LF species, probably formed by proteolysis of the fusion proteins. Purification removed this activity, so that none of the final fusion proteins had this activity. This result showed both that the purified proteins were devoid of full size LF or active LF fragments, and that the lytic activity of LF for macrophages is blocked when residues from PE are fused at its carboxyl terminus.

ADP-Ribosylation Assays

For assaying ADP-ribosylation activity, the method of Collier and Kandel (Collier, R. J. and Kandel, J. *J. Biol. Chem.* 246:1496–1503, 1971) was used with some modification. A wheat germ extract enriched for EF-2 was used in the reaction. Briefly, in a 200-µL reaction assay, 20 µL of buffer (500 mM Tris, 10 mM EDTA, 50 mM dithiothreitol and 10 mg/ml bovine serum albumin) was mixed with 30 µL of EF-2, 130 µL of $H_2O$ or sample, and 20 µL of [adenylate-$^{32}$P]NAD (0.4 µCi per assay, ICN Biochemicals) containing 5 µM of non-radioactive NAD. Samples were incubated for 20 min at 23° C., the reactions were stopped by adding 1 ml 10% trichloroacetic acid, and the precipitates were collected and washed on GA-6 filters (Gelman Sciences). The filters were washed twice with 70% ethanol, air dried, and the radioactivity measured.

Table 1 shows that all the fusion proteins were equally capable of ADP-ribosylation of EF-2. FP2, which had little cytotoxic activity on CHO cells, still retained full ADP-ribosylation activity. It was also found that treatment with urea and dithiothreitol under conditions that activate the enzymatic activity of native PE, caused no increase in the ADP-ribosylation activity of the fusion proteins, suggesting that the proteins were not folded so as to sterically block the catalytic site.

Effect of Mutant PA on LF-PE Activity

To verify that uptake of the fusion proteins requires PA, the activity of the fusion proteins was measured in the presence of a mutant PA which is apparently defective in internalization. This mutant, PA-S395C, has a serine to cysteine substitution at residue 395 of the mature protein, and retains the ability to bind to receptor, become proteolytically nicked, and bind LF, but is unable to lyse macrophages. When PA-S395C was substituted for native PA in combination with FP33, no inhibition of protein synthesis inhibition was observed. Similar results were obtained when the other three fusion proteins were tested in combination with PA-S395C.

Effect of Monensin on Activity of the Fusion Proteins

To verify that internalization of the fusion proteins was occurring by passage through acidified endosomes in the same manner as native LF, the ability of monensin to protect cells was examined. Addition of monensin to 1 µM decreased the potency of FP33 by >100-fold. Protection against the other three fusion proteins exceeded 20-fold.

LF Block of LF-PE Fusion Activity

To further verify that the fusion proteins were internalized through the PA receptor, CHO cells were incubated with PA and different amounts of LF to block the receptor and the fusion proteins were added thereafter. Protein synthesis inhibition assays showed that native LF could competitively block LF-PE fusion proteins in a concentration-dependent manner.

The present data suggest that the receptor-bound 63-kDa proteolytic fragment of PA forms a membrane channel and that regions at or near the amino-termini of LF and EF enter this channel first and thereby cross the endosomal membrane, followed by unfolding and transit of the entire polypeptide to the cytosol. This model differs from that for diphtheria toxin in that the orientation of polypeptide transfer is reversed. Since both EF and LF have large catalytic domains, extending to near their carboxyl termini, it appears probable that the entire polypeptide crosses the membrane. In the LF fusion proteins, the attached PE sequences would be carried along with the LF polypeptide in transiting the channel to the cytosol. Thus, the PA63 protein channel must tolerate diverse amino acid residues and sequences. The data presented is consistent with the mechanism of direct translocation of the LF proteins to the cytosol as suggested herein.

TABLE 1

Cytotoxic and catalytic activity of LF-PE fusion proteins

| Protein | Amino acid content | | | Toxicity | | ADP-Ribosylation activity |
|---------|-----|------|--------|----------|-------|-----------|
|         | LF  | er   | PE     | (pM)     | ng/ml | (relative) |
|         |     | Link |        | $(EC_{50})^b$ | | |
| PE      | none | none | 1–613  | 420      | 23    | 100[c]     |
| FP2     | 776  | TR   | 251–613 | 2700    | 350   | 82        |
| FP4     | 776  | TR   | 362–613 | 65      | 8     | 105       |
| FP23    | 776  | TR   | 279–613 | 70      | 10    | 108       |
| FP33    | 776  | TR   | 362–612[a] | 2    | 0.2   | 118       |

[a]REDLK at carboxyl terminus is changed to LDER.
[b]Data is from this example, except for native PE, which is from data not shown, and is equal to a value previously reported (Moehring, T. J. and Moehring, J. M. Cell 11:447–454, 1977).
[c]ADP-ribosylation was measured using 30 ng of fusion protein in a final volume of 0.200 ml with 5 μM NAD. Results were corrected for the molecular weights of the proteins and normalized to PE.

EXAMPLE 2

Residues 1–254 of Anthrax Toxin Lethal Factor are Sufficient to Cause Cellular Uptake of Fused Polypeptides Reagents and General Procedures Restriction endonucleases and DNA modifying enzymes were purchased from GIBCO/BRL, Boehringer Mannheim or New England Biolabs. Low melting point agarose (Sea Plaque) was obtained from FMC Corporation. Oligonucleotides were synthesized on a PCR Mate (Applied Biosystems) and purified with Oligonucleotide Purification Cartridges (Applied Biosystems). Polymerase chain reactions (PCR) were performed on a thermal cycler (Perkin-Elmer-Cetus) using reagents from U.S. Biochemical Corp. or Perkin-Elmer-Cetus. DNA was amplified as described in Example 1. DNA sequencing that confirmed the accuracy of all the constructs described in the report used Sequenase version 2.0 from U.S. Biochemical Corp., and DNA sequencing gels were made with Gel Mix 8 from GIBCO/BRL. [$^{35}$S]dATPαS and L-[3,4,5-$^{3}$H]leucine were purchased from Dupont-New England Nuclear. Chinese hamster ovary cells (CHO) were obtained from Michael Gottesman (NCI, NIH). J774A.1 macrophage cells were obtained from American Type Culture Collection.

Plasmid Construction

For PCR reactions to make deletions of 40 and 78 amino acids from the amino-terminus of LF, two different mutagenic oligonucleotide primers were made which had homology to the LF gene template at the intended new termini and which added KpnI sites at their 5'-ends. Another (non-mutagenic) oligonucleotide primer for introduction of a BamHI site at the 3' end of LF was prepared. Similarly, to make deletions at the carboxyl-terminus of LF, two different mutagenic primers were used which truncated LF at residues 729 and 693 and introduced a BamHI site next to the new 3' ends of the LF gene. A second (non-mutagenic) oligonucleotide primer specific for the amino terminus of LF was made which introduced a KpnI site at the 5' end of the gene. All of the primers noted above were used in PCR reactions on a pLF7 template (Robertson and Leppla, 1986) to synthesize DNA fragments having KpnI and BamHI sites at their 5' and 3' ends, respectively. The amplified LF DNAs containing the amino- and carboxyl-terminal deletions were digested with the appropriate restriction enzymes. The expression vector pVEX115f+T (provided by V. K. Chaudhary, NCI, NIH) was cleaved sequentially with KpnI and BamHI and dephosphorylated. This expression vector contains a T7 promoter, an OmpA signal sequence for protein transport to the periplasm, a multiple cloning site that includes KpnI and BamHI sites, and a T7 transcription terminator. The LF and pVEX115f+T DNA fragments were purified from low melting point agarose, ligated overnight, and transformed into E. coli DH5α. Transformants were screened by restriction digestion to identify the desired recombinant plasmids. Proteins produced by these constructs are designated according to the amino acid residues retained; for example the LF truncated at residue 693 is designated $LF^{1-693}$. All of the mutant LF proteins described above contain three non-native amino acids, Met-Val-Pro, added to the amino-terminus as a result of the PCR manipulations.

To analyze the role of the repeat region of LF, four different constructs were made: 1., removal of the entire repeat region ($LF^{1-307}.TR.LF^{384-776}$), 2., removal of the first repeat ($LF^{1-307}.TR.LF^{327-776}$), 3., removal of the last repeat ($LF^{1-364}.TR.LF^{384-776}$) and 4., removal of repeats 2–4 ($LF^{1-326}.TR.LF^{384-776}$). To construct $LF^{1-307}.TR.LF^{384-776}$, four different primers were used in two separate PCR reactions. To amplify $LF^{1-307}$, one oligonucleotide primer was made at the 5'-end of the LF gene which added a KpnI site, and a second primer was constructed at the end of residue 307, introducing an MluI site. For amplifying $LF^{384-776}$, a third primer was made at residue 384 with an added MluI site, and the fourth primer was made at the residue 776 which introduced a BamHI site at the end. Two PCR amplifications were done using primers one/two and three/four with pLF7 as template (Robertson and Leppla, 1986). The first amplification reaction was digested with KpnI and MluI separately, and the second amplification reaction was digested with MluI and BamHI. The expression vector pVEX115f+T was digested separately with KpnI and BamHI and dephosphorylated. All three fragments were gel purified, ligated overnight at 16° C. and transformed into E. coli DH5α. The other three constructs were made by similar strategies. Oligonucleotide primers one and four were the same for all four constructs, whereas primers two and three were changed accordingly. All four constructs contain Met-Val-Pro at the amino terminus of LF and Thr-Arg at the site of the repeat region deletion.

To construct LF-PE fusion proteins, fragments of the LF gene extending from the amino terminus to various lengths were amplified from plasmid pLF7 (Robertson and Leppla, 1986) by PCR using a common oligonucleotide primer that added a KpnI site at the 5' end and mutagenic primers which added MluI sites at the intended new 3' ends. The PCR products of the LF gene were digested with KpnI, the DNAs were precipitated, and subsequently digested with MluI. Domains Ib and III of the PE gene (provided by David FitzGerald, NCI, NIH) were amplified by PCR using primers which added MluI and EcoRI sites at the 5' and 3' ends, respectively. The PCR product of PE was digested with MluI and EcoRI. Similarly, the expression vector pVEX115f+T was digested with KpnI and EcoRI. All DNA fragments were purified from low-melting agarose gels, three-fragment ligations were carried out, and the products were transformed into E. coli DH5α. The three constructs described in this example have 254, 198 and 79 amino acids of LF joined with PE domains Ib and III. These fusion proteins are designated $LF^{1-254}.TR.PE^{362-613}$ (SEQ ID NO: 10), $LF^{1-198}$.TR.$PE^{362-613}$, and $LF^{1-79}$.TR.$PE^{362-613}$, respectively. The proteins retain the native carboxyl-terminal sequence of PE, REDLK. It should be noted that these abbreviations do not specify the entire amino acid content of the proteins, because all the constructs also contain Met-Val-Pro, which was added to the amino-terminus of the LF domain by the PCR manipulations.

Three types of LF protein constructs were made and analyzed in this report. All the constructs were made by PCR amplification of the desired sequences, using the native LF gene as template. LF proteins deleted at the amino- or carboxyl-terminus were constructed by a single PCR amplification reaction that added restriction sites at the ends for incorporation of the construct into the expression vector. LF proteins deleted for one or more of the 19-amino acid repeats that comprise residues 308–383 were constructed by ligating the products of two separate PCR reactions that amplified the regions bracketing the deletion. The third group of constructs were fusions of varying portions of the amino terminus of LF with PE domains Ib and III. Like the internally-deleted LF proteins, these LF-PE fusions were also made by ligation of two separate PCR products. In the latter two types of constructs, the ligation of the PCR products resulted in addition of a linker, ACGCGT, at the junction points. This introduced two non-native residues, Thr-Arg, between the fused domains. The PCR manipulations also added three non-native amino acids, Met-Val-Pro, as an extension to the native amino terminus on all the constructs described in this report. Addition of this sequence is not likely to alter the activity of the constructs (discussed below). It should be noted that the LF-PE fusions described herein contain this three-residue extension.

Expression and Purification of Deleted LF and Fusion Proteins

Recombinant plasmids were transformed into *E. coli* SA2821 (provided by Sankar Adhya, NCI, NIH), a derivative of BL21(λDE3) (Studier and Moffatt, 1986) that lacks the proteases encoded by the lon, QmDT, and degP genes, and has the T7 RNA polymerase gene under control of the lac promoter (Strauch et al., 1989). Transformants were grown in super broth with 100 μg/ml ampicillin, with shaking at 225 rpm, 37° C., in 2-L cultures. When $A_{600}$ reached 0.8–1.0, isopropyl-1-thio-β-D-galactopyranoside was added to a final concentration of 1 mM, and cultures were incubated for an additional 2 h. EDTA and 1,10-o-phenanthroline were added to 5 and 0.1 mM, respectively, and periplasmic protein was extracted as described in Example 1. The supernatant fluids were concentrated by Centriprep-30 units (Amicon) and proteins were purified to near homogeneity by gel filtration (Sephacryl S-200, Pharmacia-LKB) and anion exchange chromatography (MonoQ, Pharmacia-LKB) as described in Example 1. To determine the percentage of full length protein, SDS gels stained with Coomassie Brilliant Blue were scanned with a laser densitometer (Pharmacia-LKB Ultrascan XL). Western blots were performed as described previously (Singh et al., 1991).

The LF proteins having terminal deletions and the LF-PE fusion proteins were obtained from periplasmic extracts and purified to near homogeneity by gel filtration and anion exchange chromatography. The migration of the proteins was consistent with their expected molecular weights. Immunoblots confirmed that the LF proteins had reactivity with LF antisera, and the LF-PE fusion proteins had reactivity with both LF and PE antisera. Fusion proteins and terminally-deleted LF proteins differed in their susceptibility to proteolysis as judged by the appearance of peptide fragments on the immunoblots, and this was also reflected in the different amounts of purified proteins obtained. Thus, from 2-L cultures the yields of purified proteins were $LF^{41-776}$, 39 μg; $LF^{79-776}$, 32 μg; $LF^{1-729}$, 50 μg; $LF^{1-693}$, 46 μg; $LF^{1-254}$.TR.$PE^{362-613}$, 184 μg; $LF^{1-198}$.TR.$PE^{362-613}$, 80 μg; $LF^{1-79}$.TR.$PE^{362-613}$, 127 μg.

LF proteins deleted in the repeat region were found to be unstable and full size product could not be purified. Therefore, the activities of these proteins were determined by assay of crude periplasmic extracts, and immunoblots were used to estimate the amount of the full size proteins present.

Cytotoxicity on Macrophages of LF Proteins Having Terminal and Internal Deletions Deleted LF proteins were assayed for LF functional activity on the J774A.1 macrophage cell line in the presence of native PA as described in Example 1. Briefly, cells were plated in 24- or 48-well dishes in Dulbecco's modified Eagle medium (DMEM) containing 10% fetal bovine serum, and allowed to grow for 18 h. PA (1 μg/ml) and the mutant LF proteins were added and cells were incubated for 3 h. To measure the viability of the treated cells, 3-[4,5-dimethylthiazol-2-yl]-2,5-diphenyltetrazolium bromide (MTT) was added to the cells to a final concentration of 0.5 mg/ml. After incubating for 45 min, the medium was aspirated and cells were dissolved in 90% isopropanol, 0.5% SDS, 40 mM HCl, and read at 540 nm using a UVmax Kinetic Microplate Reader (Molecular Devices Corp.).

To determine the extent of essential sequences at the amino terminus of LF, the toxicities of the two LF proteins deleted at the amino-terminus were measured in combination with PA in the macrophage lysis assay. Purified $LF^{41-776}$ and $LF^{79-776}$ were unable to lyse J774A.1 macrophage cells. This indicates that some portion of the sequence preceding residue 41 is needed to maintain an active LF protein.

To examine the role of the carboxyl terminus of LF, two proteins truncated in this region were prepared and analyzed. The proteins $LF^{1-693}$ and $LF^{1-729}$ were assayed on J774A.1 cells and found to be inactive. This is presumed to be due to inactivation of the putative catalytic domain.

To begin study of the role of the repeat region of LF, four constructs were made having deletions in this region. The proteins expressed from these mutants were unstable. Of the four deleted proteins, only $LF^{1-307}$.TR.$LF^{327-776}$ had immunoreactive material at the position expected of intact fusion protein. The amount of intact $LF^{1-307}$.TR.$LF^{327-776}$ was similar to that of native LF expressed in the same vector. When these unpurified periplasmic extracts were tested in J774A.1 macrophages, only the native LF control was toxic. $LF^{1-307}$.TR.$LF^{327-776}$ did not lyse macrophages even when present at 50-fold higher concentration than that of crude periplasmic protein of LF. Conclusions cannot be drawn about the toxicities of the other three constructs because full size fusion proteins were not present in the periplasmic extracts.

Cell Culture Techniques and Protein Synthesis Inhibition Assay of Fusion Proteins CHO cells were maintained as monolayers in s-modified minimum essential medium ($\alpha$-MEM) supplemented with 5% fetal bovine serum, 10 mM HEPES (pH 7.3), and penicillin/streptomycin. Protein synthesis assays were carried out in 24- or 48-well dishes as described in Example 1. CHO cells were incubated with PA (0.1 ug/ml) and varying concentrations of LF, which is expected to block the receptor. Fusion proteins were added at fixed concentrations, as follows: FP4, 100 ng/ml, FP23, 100 ng/ml, and FP33, 5 ng/ml. Cells were incubated for 20 hr and protein synthesis inhibition was evaluated by [$^3$H]leucine incorporation.

Cytotoxicity of the LF-PE Fusion Proteins on CHO Cells

The use of fusion proteins provides a more defined method for measuring the translocation of LF, as demonstrated in Example 1 showing that fusions of LF with domains Ib and III of PE are highly toxic. Translocation of these fusions is conveniently measured because domain III blocks protein synthesis by ADP-ribosylation of elongation factor 2. The new fusions containing varying portions of LF fused to PE domains Ib and III were designed to identify the minimum LF sequence able to promote translocation. The $EC_{50}$ of $LF^{1-254}.TR.PE^{362-613}$ (SEQ ID NO: 10) was 1.7 ng/ml, whereas $LF^{1-198}.TR.PE^{362-613}$ and $LF^{1-79}.TR.PE^{362-613}$ did not kill 50% of the cells even at a 1200-fold higher concentration. Other constructs were also made and analyzed, containing larger portions of LF fused to PE domains Ib and III, and found those to be equal in potency to $LF^{1-254}.TR.PE^{362-613}$. These results show that residues 1–254 contain all the sequences essential for binding to PA63. The fusion proteins had no toxicity in the absence of PA, proving that their internalization absolutely requires interaction with PA.

Binding of Fusion Proteins and Deleted LF Proteins to PA

Binding of LF proteins to cell bound PA was determined by competition with radiolabeled $^{125}$-LF. Native LF was radiolabeled ($3.1\times10^6$ cpm/μg protein) using the Bolton-Hunter reagent. Binding studies employed the L6 rat myoblast cell line, which has approximately twice as many receptors as the J774A.1 macrophage line (Singh et al., 1989). For convenience, cells were chemically fixed by a gentle procedure that preserves the binding activity of the receptor as well as the ability of the cell-surface protease to cleave PA to produce receptor-bound PA63. Assays were carried out in 24-well dishes using cells plated in DMEM with 10% fetal bovine serum one day before the experiment. Cell monolayers were washed twice with Hanks' balanced salt solution (HBSS) containing 25 mM HEPES and were chemically fixed for 30 min at 23° in 10 mM N-hydroxysuccinimide and 30 mM 1-ethyl-3-[3-dimethyl[aminopropyl]carbodiimide], in buffer containing 10 mM HEPES, 140 mM NaCl, 1 mM $CaCl_2$, and 1 mM $MgCl_2$. Monolayers were washed with HBSS containing 25 mM HEPES and the fixative was inactivated by incubating 30 min at 23° in DMEM (without serum) containing 25 mM HEPES. Native PA was added at 1 μg/ml in minimum essential medium containing Hanks' salts, 25 mM HEPES, 1% bovine serum albumin, and a total of 4.5 mM $NaHCO_3$. Cells were incubated overnight at room temperature to allow binding and cleavage of PA. Cells were washed twice in HBSS and mutant LF proteins (0–5000 ng/ml) along with 50 ng/ml $^{125}$I-LF was added to each well. Cells were further incubated for 5 h, washed three times in HBSS, dissolved in 0.5 ml 1N NaOH, and counted in a gamma counter (Beckman Gamma 9000).

Using this assay, the amino-terminal deletions of LF were found incapable of binding to PA, thereby explaining their lack of toxicity. Carboxyl-terminal deleted proteins of LF did bind in a dose dependent manner, although they had slightly lower affinity than LF. The proteins deleted in the repeat region could not be tested for competitive binding because their instability prevented purification of intact protein.

The $EC_{50}$ for $LF^{1-254}.TR.PE^{362-613}$ binding was found to be 220 ng/ml, which is similar to that of LF, 300 ng/ml. Therefore the binding data correlate well with the toxicity of this construct. In contrast, neither $LF^{1-198}.TR.PE^{362-613}$ nor $LF^{1-79}.TR.PE^{362-613}$ bound to PA63 on cells, thereby explaining their lack of toxicity.

EXAMPLE 3

Construction of Genes Encoding PA-fusion Proteins

The genes encoding PA (or PA truncated at the carboxyl terminus to abrogate binding to the PA receptor) and an alternative targeting moiety (a single-chain antibody, growth factor, or other cell type-specific domain) are spliced using conventional molecular biological techniques. The PA gene is readily available, and the genes encoding alternative targeting domains are derived as described below.

Single-chain Antibodies (sFv)

See Example 4, below.

Growth factors and other targeting proteins

The nucleotide sequences of genes encoding a number of growth factors are reported in freely accessible databases (e.g., GenBank), and in many cases the genes are available. In circumstances where this is not the case, genes may be produced de novo from chemically synthesized overlapping oligonucleotides, using the preferred codon usage of the expression host. For example, the gene for human epidermal growth factor urogastrone was synthesized from the known amino acid sequence of human urogastrone using yeast preferred codons. The cloned DNA, under control of the yeast GAPDH promoter and yeast ADH-1 terminator, expresses a product having the same properties as natural human urogastrone. The product of this synthesized gene is nearly identical to that of the synthetic beta-urogastrone the only difference being at amino acid 13 (trp in this gene vs tyr in the other) (Urdea et al. *Proc. Natl. Acad. Sci. USA* 80:7461–7465, 1983).

Expression of PA-fusion proteins.

Once constructed, genes encoding PA-fusion proteins are expressed in *Bacillus anthracis*, and recombinant proteins are purified by one of the following methods: (i) size-based chromatographic separation; (ii) affinity chromatography. In the case of PA-sFv fusions, immobilized metal chelate affinity chromatography may be the purification method of choice, because addition of a string of six histidine residues at the carboxyl terminus of the sFv will have no detrimental effect on binding to antigen. Additional methods of expression of PA-fusion proteins utilize an in vitro rabbit reticulocyte lysate-based coupled transcription/translation system, which has been demonstrated to accurately refold chimeric proteins consisting of an sFv fused to diphtheria toxin, or Pseudomonas exotoxin A as demonstrated in Example 4.

Functional testing of PA-fusion proteins.

After expression and purification, functionality of PA-fusion proteins are tested by determining their ability to act in concert with an LF-PE fusion protein to inhibit protein synthesis in an appropriate cell line. Using a PA-anti human transferrin receptor sFv fusion as a model, the following properties are examined: (i) Cell type-specificity (protein synthesis should be inhibited in cell lines which express the human transferrin receptor, but not in those which do not); (ii) Independence of toxicity from PA receptor binding (excess free PA should have no effect on toxicity of the PA-sFv/LF-PE complex); (iii) Competitive inhibition by excess free antibody (toxicity should be abrogated in the presence of excess sFv, or the monoclonal antibody from which it was derived). For example such tests are described in Examples 4 and 5. These studies and other studies are used to confirm that PA has been successfully re-routed to an alternative receptor to permit the use of the present anthrax toxin-based cell type-specific cytotoxic agents for the treatment of disease.

EXAMPLE 4

Generating Fusion Proteins with Single-chain Antibodies

Reagents

Methionine-free rabbit reticulocyte lysate-based coupled transcription/translation reagents, recombinant ribonuclease inhibitor (rRNasin), and cartridges for the purification of plasmid DNA were purchased from Promega (Madison, Wis.). Tissue culture supplies were from GIBCO (Grand Island, N.Y.) and Biofluids (Rockville, Md.). OKT9 monoclonal antibody was purchased from Ortho Diagnostic Systems (Raritan, N.J.). PCR reagents were obtained from by Perkin-Elmer Cetus Instruments (Norwalk, Conn.), and restriction and nucleic acid modifying enzymes (including M-MLV reverse transcriptase) were from GIBCO-BRL (Gaithersburg, Md.). A Geneclean kit for the recovery of DNA from agarose gels was supplied by BIO 101 (La Jolla, Calif.). Hybridoma mRNA was isolated using a Fast Trak mRNA isolation kit (Invitrogen, San Diego, Calif.). All isotopes were purchased from Du Pont-New England Nuclear (Boston, Mass.), except [Adenylate-$^{32}$P]NAD, which was supplied by ICN Biomedicals (Costa Mesa, Calif.). Pseudomonas exotoxin A was obtained from List Biologicals (Campbell, Calif.). Oligonucleotides were synthesized on a dual column Milligen-Biosearch Cyclone Plus DNA synthesizer (Burlington, Mass.), and purified using OPC cartridges (Applied Biosystems, Foster City, Calif.). DNA templates were sequenced using a Sequenase II kit (United States Biochemical Corp., Cleveland, Ohio), and SDS-PAGE was performed using 10–20% gradient gels (Daiichi, Tokyo, Japan). After electrophoresis, gels were fixed in 10% methanol/7% acetic acid, and soaked in autoradiography enhancer (Amplify, Amersham Arlington Heights, Ill.). After drying, autoradiography was performed overnight using X-OMAT AR2 film (Eastman Kodak, Rochester, N.Y.).

Plasmids

The vector pET-11d is available from Novagen, Inc., Madison, Wis. Plasmids were maintained and propagated in *E. coli* strain XL1-Blue (Stratagene, La Jolla, Calif.).

Cell Lines

K562, a human erythroleukemia-derived cell line [ATCC CCL 243] known to express high levels of the human transferrin receptor at the cell surface, was cultured in RPMI 1640 medium containing 24 mM NaHCO$_3$, 10% fetal calf serum, 2 mM glutamine, 1 mM sodium pyruvate, 0.1 mM nonessential amino acids, and 10 μg/ml gentamycin. An African green monkey kidney line, Vero (ATCC CCL 81), was grown in Dulbecco's modified Eagle's medium (DMEM) supplemented as indicated above. The OKT9 hybridoma (ATCC CRL 8021), which produces a MoAb (IgG$_1$) reactive to the human transferrin receptor, was maintained in Iscove's modified Dulbecco's medium containing 20% fetal calf serum, in addition to the supplements described above. All cell lines were cultured at 37° C. in a 5% CO$_2$ humidified atmosphere.

Construction of sFv from Hybridomas

Antibody $V_L$ and $V_H$ genes were cloned using a modification of a previously described technique (Larrick et al. *Biotechniques* 7:360, 1989; Orlandi et al. *Proc. Natl. Acad. Sci. USA* 86:3833, 1989; Chaudhary et al., 1990). Briefly, mRNA was isolated from 1×10$^8$ antibody producing hybridoma cells, and approximately 3 μg was reverse transcribed with M-MLV reverse transcriptase, using random hexanucleotides as primers. The resulting cDNA was screened with two sets of PCR primer pairs designed to ascertain which Kabat gene family heavy and light chains were derived from (Kabat et al. Sequences of proteins of immunological interest. Fifth Edition. (Bethesda, Md.: U.S. Public Health Service, 1991). Having identified the most effective primer pairs, cDNA's encoding $V_L$ and $V_H$ were spliced, separated by a region encoding a 15 amino acid peptide linker, using a previously described PCR technique known as gene splicing by overlap extension (SOE) (Johnson & Bird *Methods Enzymol.* 203:88, 1991). The sFv gene was then cloned into pET-11d, in frame and on the 5'-side of the PE40 gene, such that expression of the construct should generate an sFv-PE40 fusion protein approximately 70 kDa in size.

Design of Primers for PCR Amplification of V Region Genes

The first and third complementarity determining regions (CDRs) of terminally rearranged immunoglobulin variable region genes are flanked by conserved sequences (the first framework region, FR1 on the 5' side of CDR1, and the fourth framework region, FR4, on the 3' side of CDR3 ).

Although murine variable region genes have been successfully cloned, regardless of family, with just two pairs of highly degenerate primers (one pair for $V_L$ and another for $V_H$) (Gussow et al. *Cold Spring Harbor Symp. Quant. Biol.* 54:265, 1989; Orlandi et al., 1989; Chaudhary et al., 1990; Batra et al., 1991), the method may not be effective in cases where the number of mismatches between primers and the target sequence is extensive. With this in mind, using the Kabat database of murine V gene sequences the present invention provides a set of ten FR1-derived primers (six for $V_L$ and four for $V_H$), such that any of the database sequences selected at random would have a maximum of three mismatches with the most homologous primer. This set of primers can be used effectively to clone V region genes from a number of MoAb secreting cell lines.

Assembly of the OKT9 sFv Gene mRNA isolated from the hybridoma secreting the OKT9 MoAb was converted to cDNA as described previously (Larrick et al., 1989; Orlandi et al., 1989; Chaudhary et al., 1990). Despite the fact that CL-UNI is the partnering oligonucleotide in each case, a product the required size (approximately 400 bp) is not produced by $V_L$ primers IV/VI, IIa or IIb. This suggests that mismatches between these primers and the target sequence were too extensive to allow efficient amplification. A similar argument can be used to explain the failure of $V_H$ primers I and III to produce the required product. It is clear that primers $V_L$-I/III and $V_H$-V are most effective at amplifying the OKT9 $V_L$ and $V_H$ genes respectively. PCR amplified OKT9 $V_L$ and $V_H$ genes were spliced together using the SOE technique, as previously described (Johnson & Bird, 1991). A synthetic DNA sequence encoding a 15 amino acid linker, was inserted between the variable regions; this linker has been used very effectively in the production of functional sFv (Huston et al., 1991; Johnson & Bird, 1991), and appears to allow the variable chains to assume the optimum orientation for antigen binding. Following splicing of V region genes by the SOE procedure, the DNA fragment encoding the OKT9 sFv was electrophoresed through a 1.5% agarose gel, purified by the Geneclean technique, digested with the appropriate pair of restriction enzymes, and cloned into the pET-11d expression vector in frame and on the 5' side of the PE40 gene.

In Vitro Expression of sFv-PE40 Fusion Proteins

Plasmid templates were transcribed and translated using a rabbit reticulocyte lysate-based transcription/translation system, according to the instructions of the manufacturer, in 96-well microtiter plate format L-[$^{35}$S]methionine-labeled proteins (for analysis by SDS-PAGE) and unlabeled proteins (for enzymatic analysis and bioassay), were produced in similar conditions, except that the isotope was replaced with 20 µM unlabeled L-methionine in the latter case. Control lysate was produced by adding all reagents except plasmid DNA. After translation, unlabeled samples were dialysed overnight at 4° C. against phosphate-buffered saline (PBS), pH 7.4 in Spectra/Por 6 MWCO 50,000 tubing (Spectrum, Houston, Tex.).

Constructs incorporating the aberrant kappa transcript will contain a translation termination codon in the $V_L$ chain as previously described, and would therefore be expected to generate a translation product approximately 12 kDa in size. On the other hand, constructs which have incorporated the productive $V_L$ gene contain no such termination codon, and a full-length fusion protein (approximately 70 kDa in size) should be produced.

In vitro expression studies were used to determine the size of the protein encoded by the OKT9 sFv-PE40 gene. The constructs tested in this experiment clearly produce a protein of approximately 70 kDa, indicating that the clones do not contain the aberrant $V_L$ gene, and are devoid of frameshift mutations. Of several OKT9 sFv constructs tested, none apparently incorporated the incorrect VL gene. However, in the case of another sFv generated by this method (1B7 sFv, derived from a MoAb which binds to pertussis toxin), the majority of the clones tested produced a 12 kDa protein, and were found to contain the aberrant transcript on DNA sequencing. It should be noted that the 12 kDa fragment is frequently obscured in 10–20% gradient gels by unincorporated $^{35}$S-methionine which co-migrates with the dye front.

Determination of Protein Concentration

The enzymatic activities of fusion proteins were compared with those of known concentrations of PE in an ADP-ribosyl transferase assay, allowing molarities to be determined (Johnson et al. J. Biol. Chem. 263:1295–1399, 1988). Samples were adjusted to contain equivalent concentrations of lysate, thus maintaining an identical amount of substrate (elongation factor 2) in all cases.

Protein Synthesis Inhibition Assay for Functional sFv-PE40 Binding

Binding of the OKT9 sFv to the human transferrin receptor was qualitatively determined by assessing the ability of the OKT9 sFv-PE40 fusion protein to inhibit protein synthesis in the K562 cell line. Pseudomonas exotoxin A is a bacterial protein which is capable of inhibiting de novo protein synthesis in a variety of eukaryotic cell types. The toxin binds to the cell surface, and ultimately translocates to the cytosol where it enzymatically inactivates elongation factor 2. PE40 is a mutant form of exotoxin A which lacks a binding domain, but is enzymatically active, and capable of translocation. Fusion proteins containing PE40 and an alternative binding domain (for example, an sFv to a cell surface receptor) will inhibit protein synthesis in an appropriate cell line only if the sFv binds to a cell-surface antigen which subsequently internalizes into an acidified endosome (Chaudhary et al., 1989). The TfnR is such an antigen, so a qualitative assessment of binding may be determined by measuring the ability of the OKT9 sFv-PE40 fusion protein to inhibit protein synthesis in a cell line like K562, which expresses the TfnR. Protein synthesis inhibition assays were performed as described previously (Johnson et al., 1988). Briefly, samples were serially diluted in ice cold PBS, 0.2% BSA, and 11 µl volumes were added to the appropriate well of a 96-well microtiter plate (containing $10^4$ cells/100 µl/well in leucine-free RPMI 1640). After carefully mixing the contents of each well, the plate was incubated for the indicated time at 37° C. in a 5% $CO_2$ humidified atmosphere. Each well was then pulsed with 20 µl of L-[14C(U)]leucine (0.1 µCi/20 µl), incubated for 1 hour, and harvested onto glass fiber filters using a PHD cell harvester (Cambridge Technology, Cambridge, Mass.). Results are expressed as a percentage of the isotope incorporation in cells treated with appropriate concentrations of control dialyzed lysate.

The results of this assay, clearly indicate that OKT9 sFv-PE40 is capable of inhibiting protein synthesis with an $IC_{50}$ (the concentration of a reagent which inhibits protein synthesis by 50%) of approximately $2 \times 10^{-9}$M. The toxicity of the fusion protein, but not of PE, was abrogated in the presence of excess OKT9 MoAb (12 µg/ml), indicating that binding is specific for the TfnR. No toxicity was observed when K562 was substituted with Vero (an African Green monkey cell line which expresses the simian version of the transferrin receptor), indicating that the OKT9 sFv retains the human receptor-specific antigen binding properties of the parent antibody. Having demonstrated binding of the OKT9 sFv to TfnR, its nucleotide sequence was determined using dideoxynucleotide chain-terminating methods, confirming extensive homology with the respective regions of immunoglobulins of known sequence.

EXAMPLE 5

Characterization of Single-chain Antibody (sFv)-toxin Fusion Proteins Produced in Vitro in Rabbit Reticulocyte Lysate The present invention provides in vitro production of proteins containing a toxin domain (derived from Diphtheria toxin (DT) or PE) fused to a domain encoding a single-chain antibody directed against the human transferrin receptor (TfnR). The expression of this antigen on the cell surface is coordinately regulated with cell growth; TfnR exhibits a limited pattern of expression in normal tissue, but is widely distributed on carcinomas and sarcomas (Gatter, et al. *J. Clin. Pathol.* 36:539–545, 1983), and may therefore be a suitable target for IT-based therapeutic strategies (Johnson, V. G. and Youle, R. J. "Intracellular Trafficking of Proteins" Cambridge Univ. Press, Cambridge England, Steer and Hover eds., pp. 183–225; Batra et al., 1991; Johnson et al., 1988).

Proteins consisting of a fusion between an sFv directed against the TfnR and either the carboxyl-terminus 40 kDa of PE, or the DT mutant CRM 107 [S(525)F] were expressed in rabbit reticulocyte lysates, and found to be specifically cytotoxic to K562, a cell line known to express TfnR. In comparison, a chimeric protein consisting of a fusion between a second DT mutant, DTM1 [S(508)F, S(525)F] and the E6 sFv exhibited significantly lower cytotoxicity. Legal restrictions imposed on manipulating toxin genes in vivo previously prevented expression of potentially interesting toxin-containing fusion proteins (*Federal Register* 51(88)(III):16961 and Appendix F:16971); the present invention provides a novel procedure for in vitro gene construction and expression which satisfies the regulatory requirements, facilitating the first study of the potential of non-truncated DT mutants in fusion protein ITs. The present dats also demonstrates that functional recombinant antibodies can be generated in vitro.

Reagents

DT and PE were purchased from List Biologicals (Campbell, Calif.). Nuclease treated, methionine-free rabbit reticulocyte lysate and recombinant ribonuclease inhibitor (rRNasin) were obtained from Promega (Madison, Wis.). Tissue culture supplies were from GIBCO (Grand Island, N.Y.) and Biofluids (Rockville, Md.). Reagents for PCR were provided by Perkin-Elmer Cetus (Norwalk, Conn.). Restriction and nucleic acid modifying enzymes were from Stratagene (La Jolla, Calif.), as was the mCAP kit used to produce capped mRNA in vitro. Geneclean and RNaid kits (for the purification of DNA and RNA respectively) were supplied by BIO 101 (La Jolla, Calif.). L-[$^{35}$S]methionine, L-[$^{14}$C(U)]leucine and 5'-(alpha-thio)-[$^{35}$S]dATP were from New England Nuclear (Boston, Mass.). [Adenylate-$^{32}$P]NAD was supplied by ICN Biomedicals (Costa Mesa, Calif.).

Oligonucleotide Synthesis

Oligonucleotides were synthesized (0.2 µM scale), using cyanoethylphosphoramidites supplied by Milligen-Biosearch (Burlington, Mass.) on a dual column Cyclone Plus DNA synthesizer. Post-synthesis purification was achieved using OPC cartridges (Applied Biosystems, Foster City, Calif.).

Plasmids pET-11d was the generous gift of Dr. F. William Studier, Brookhaven National Laboratory (Upton, N.Y.). pHB21-PE40, a derivative of pET-11d containing the gene for PE40, was kindly supplied by Dr. David FitzGerald (NIH, Bethesda, Md.). All plasmids were maintained and propagated in *E. coli* strain XL1-Blue (Stratagene, La Jolla, Calif.).

Cell Lines

*Corynebacterium diphtheriae* strain C7$_s$(β)$^{tox+}$ (ATCC 27012) was obtained from the ATCC (Rockville, Md.), and the strain producing the binding-deficient DT mutant CRM 103 was the generous gift of Dr. Neil Groman, University of Washington (Seattle, Wash.). Both strains were propagated in LB broth. K562 (a human erythroleukemia-derived cell line, ATCC CCL 243) was cultured in RPMI 1640 medium containing 24 mM NaHCO$_3$, 10% fetal calf serum, 2 mM glutamine, 1 mM sodium pyruvate, 0.1 mM nonessential amino acids, and 10 µg/ml gentamycin. Vero (an African green monkey kidney line, ATCC CCL 81) was grown in Dulbecco's modified Eagle's medium supplemented as described above. All eukaryotic cells were cultured at 37° C. in a 5% CO$_2$ humidified atmosphere.

Splicing Genes using PCR

Genes encoding antibody V$_L$ and V$_H$ were spliced, separated by a region encoding a 15 amino acid peptide linker, using a previously described PCR technique known as gene splicing by overlap extension (SOE) (Horton et al. *Gene* 77:61–68, 1989; Horton et al. *Biotechniques* 8:528–535, 1990). For studies requiring in vitro expression of PCR products, tox gene-derived fragments were linked to those encoding sFv using a similar method, without the use of restriction enzymes.

Construction of Plasmids Encoding Toxin-sFv Fusion Proteins

The gene encoding PE40 was obtained as an insert in pET-11d, and the sFv gene was cloned on the 5' side of this insert as indicated. For cloning the gene encoding the DT binding-site mutant DTM1 [S(508)F, S(525)F], genomic DNA was isolated from the *C. diphtheriae* strain which produces CRM 103 by a modification of the cetyltrimethylammonium bromide extraction procedure (Wilson, K. "Current Protocols in Molecular Biology" Asubel et al. eds. John Wiley & Sons New York, 2.4.1–2.4.5, 1988), and subjected to 20 cycles of PCR amplification. Primers were designed to: (i) amplify the 1605 bp region encoding CRM 103, concomitantly mutating the codon at position 525 from TCT to TTT, and (ii) incorporate restriction sites appropriate for cloning. The mutations present in CRM 107 and CRM 103 were thus combined on a single gene.

In Vitro Transcription of DNA Templates

For transcription, DNA templates required a T7 RNA polymerase promoter immediately upstream of the gene of interest (Oakley, J. L. and Coleman, J. E. *Proc. Acad. Sci. U.S.A.* 74:4266–4270, 1977). Such a promoter was conveniently present in pET-11d (Studier et al. *Enzymol* 185:60–89, 1990). In the case of PCR products, the upstream primer (a 57-mer, T7-DT) was used to introduce all of the elements necessary for in vitro transcription/translation. T7-DT includes a consensus T7 RNA polymerase promoter, together with the first seven codons of mature DT (Greenfield et al. *Proc. Natl. Acad. Sci. U.S.A.* 80:6853–6857, 1983) immediately preceded by an ATG translation initiation codon in the optimum Kozak context (Kozak, M. *J. Biol. Chem.* 266:19867–19870, 1991). m7G(5')ppp(5')G-capped RNA was produced by transcription from linearized plasmids or PCR products using an mCAP kit, according to the manufacturer's protocol. Prior to translation, RNA was purified using an RNaid kit, recovered in nuclease free water, and analyzed by formaldehyde gel electrophoresis.

In Vitro Expression of Fusion Proteins

L-[$^{35}$S]methionine-labelled proteins (for analysis by SDS-PAGE) were produced from capped RNA in methionine-free, nuclease treated rabbit reticulocyte lysate, according to the supplier's instructions. Unlabeled proteins (for bioassay), were produced in similar conditions, except that the isotope was replaced with 20 µM unlabeled L-methionine. Control lysate was produced by adding all reagents except exogenous RNA. After translation, samples were dialysed overnight at 4° C. against PBS, pH 7.4 in Spectra/Por 6 MWCO 50,000 tubing (Spectrum, Houston, Tex.).

Prior to transcription, plasmids were linearized at the BglII site, and treated with proteinase K to destroy ribonucleases which may contaminate the sample. After phenol/chloroform extraction and ethanol precipitation, DNA was dissolved in nuclease free water to a concentration of approximately 0.2 µg/µl. m$^7$G(5')ppp(5')G-capped RNA was synthesized by T7 RNA polymerase using the conditions recommended by the manufacturer, and its integrity was confirmed by formaldehyde gel electrophoresis. Capped RNA was translated in a commercially available rabbit reticulocyte lysate, according to the instructions of the manufacturer. It is clear from the gel that the major band in each case has a molecular weight corresponding to that of the protein of interest, and that relatively large molecules (approximately 120 kDa in the case of DTM1-E6 sFv-PE40) can be synthesized in the lysate using the conditions described.

Immediately following translation, samples were extensively dialyzed overnight at 4° C. against PBS, pH 7.4. The dialysis step was found to be essential, because non-dialyzed rabbit reticulocyte lysate resulted in the incorporation of significantly lower amounts of $^{14}$C-leucine upon assay by protein synthesis inhibition in all cell lines tested. After determining the concentration of the newly synthesized protein using a standard assay for measuring ADP-ribosyltransferase activity (Johnson et al., 1988), the cytotoxic activity of samples was immediately determined.

ADP-ribosyl Transferase Assay

The enzymatic activity (and therefore molarity) of fusion proteins was determined by comparison with DT or PE standard curves, as described previously (Johnson et al., 1988). Appropriate volumes of control lysate were added to each standard curve sample, in order to control for the presence of significant levels of EF-2 in reticulocyte lysate.

Other Methods

SDS-PAGE was performed as previously described (Laemmli, U. K. *Nature* 227:680–685, 1970), using 10–20% gradient gels (Daiichi, Tokyo, Japan). Once electrophoresis was complete, gels were fixed for 15 minutes in 10% methanol, 7% acetic acid, and then soaked for 30 minutes in autoradiography enhancer (Amplify, Amersham Arlington Heights, Ill.). After drying, autoradiography was performed overnight using X-OMAT AR2 film (Eastman Kodak, Rochester, N.Y.), in the absence of intensifying screens. Dideoxynucleotide chain-termination sequencing of double-stranded DNA templates was performed using a Sequenase II kit (United States Biochemical Corp., Cleveland, Ohio), according to the manufacturer's protocol.

Cytotoxicity of Toxin-sFv Fusion Proteins Expressed in Reticulocyte Lysates

The cytotoxic activity of fusion proteins was determined by their ability to inhibit protein synthesis in relevant cell lines (e.g., K562). Assays were performed as described previously (Johnson et al., 1988). Briefly, samples were serially diluted in ice cold PBS, 0.2% BSA, and 11 µl volumes were added to the appropriate well of a 96-well microtiter plate (containing $10^4$ cells/well in leucine-free RPMI 1640). After carefully mixing the contents of each well, the plate was incubated for the indicated time at 37° C. in a 5% $CO_2$ humidified atmosphere. Each well was then pulsed with 20 µl of L-[$^{14}$C(U)]leucine (0.1 µCi/20 µl), incubated for 1 hour, and harvested onto glass fiber filters using a PHD cell harvester (Cambridge Technology, Cambridge, Mass.). Results were expressed as a percentage of the isotope incorporation in cells treated with appropriate concentrations of control dialyzed lysate.

The results of the protein synthesis inhibition assay clearly indicate that PE40-containing fusion proteins synthesized in cell-free reticulocyte lysates are highly cytotoxic to this cell line ($IC_{50}$ $1\times10^{-10}$M). In contrast, DTM1-E6 sFv was at least ten-fold less toxic to K562 than the PE40-containing fusion protein, despite the fact that it exhibited ADP-ribosyl transferase activity indistinguishable from that of wt DT synthesized from an equivalent amount of RNA in an identical reticulocyte lysate mix. Since the decreased toxicity of DTM1-E6 sFv is clearly not due to a deficit in enzymatic activity, the binding and/or translocation process is implicated. Possible mechanisms by which the sFv-antigen interaction could be inhibited include: (i) misfolding of the sFv domain or (ii) steric interactions with other regions of the fusion protein preventing close association of sFv with the TfnR. It is of interest that a tripartite protein, DTM1-E6 sFv-PE40 was significantly cytotoxic to K562 ($IC_{50}$ around $1\times10^{-10}$M, similar to that of PE40-E6 sFv), and the toxic effect was clearly mediated via the TfnR, since this activity was blocked by addition of excess E6 Mab. Although it is possible that the inclusion of the PE40 moiety at the carboxyl end of the tripartite molecule results in a significant conformational change in domains more proximal to the amino terminus, it seems unlikely that the sFv binding domain of DTM1-E6 is misfolded, or unavailable to interact with the TfnR. Interactions of DTM1-E6 sFv with the cell surface could be measured in a direct binding assay (Greenfield et al. *Science* 238:536–539, 1987), but these studies were not performed in the course of this investigation. Nevertheless, it appears likely that the lack of toxicity of the DTM1-E6 sFv fusion protein is due to a deficit in its translocation function.

The expression system developed is rapid and easy, and facilitates the manipulation of a number of samples at once. No complicated protein purification or refolding procedures are required, and the method may be used to express proteins which, due to restrictions imposed on the manipulation of toxin-encoding genes, could not be produced by more conventional methods. The technique is ideal for ascertaining the suitability of new sFv for IT development; it is theoretically possible to assemble the sFv-encoding gene (and that encoding the IT itself) by splicing of PCR products derived directly from the hybridoma, without the necessity for cloning. This would facilitate the selection of the most promising candidate molecule, prior to investing considerable effort and expense in large scale protein production and purification. Toxins and toxin-containing fusion proteins are proving to be powerful aids in our understanding of receptor mediated endocytosis and intracellular routing, and are providing valuable insight into normal cell function (reviewed in ref. 2). The method described simplifies the generation of such molecules, and facilitates their production and use in laboratories in which the application of more conventional expression methods would be impractical.

---

What is claimed is:

1. A nucleic acid encoding a fusion protein, comprising a nucleotide sequence encoding the protective antigen (PA) binding domain of the native lethal factor (LF) protein and a nucleotide sequence encoding a polypeptide, wherein said fusion protein lacks the catalytic domain of LF.

2. The nucleic acid of claim 1, wherein the polypeptide is a toxin.

3. The nucleic acid of claim 2, wherein the toxin is Pseudomonas exotoxin A.

4. The nucleic acid of claim 2, wherein the toxin is the A chain of Diphtheria toxin.

5. The nucleic acid of claim 2, wherein the toxin is shiga toxin.

6. The nucleic acid of claim 1, comprising the nucleotide sequence defined in the Sequence Listing as SEQ ID NO:5.

7. The nucleic acid of claim 1, wherein the fusion protein comprises the protein defined in the Sequence Listing as SEQ ID NO:6.

8. A protein encoded by the nucleic acid of claim 1.

9. A vector comprising the nucleic acid of claim 1.

10. The vector of claim 9 in a host that expresses the protein encoded by the nucleic acid.

11. A compound comprising the protective antigen (PA) binding domain of the native lethal factor (LF) protein chemically attached to a polypeptide, wherein said compound lacks the catalytic domain of LF.

12. The compound of claim 11 wherein the polypeptide is a toxin.

13. The compound of claim 11 wherein the polypeptide is a growth factor.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3291 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus anthracis ( i x ) FEATURE:
        ( A ) NAME/KEY: CDS
        ( B ) LOCATION: 580..2907

( x i ) SEQUENCE DESCRIPTION: SEQ ID NO:1:

```
AAATTAGGAT  TTCGGTTATG  TTTAGTATTT  TTTTAAAATA  ATAGTATTAA  ATAGTGGAAT    60

GCAAATGATA  AATGGGCTTT  AAACAAAACT  AATGAAATAA  TCTACAAATG  GAATTTCTCC   120

AGTTTTAGAT  TAAACCATAC  CAAAAAAATC  ACACTGTCAA  GAAAAATGAT  AGAATCCCTA   180

CACTAATTAA  CATAACCAAA  TTGGTAGTTA  TAGGTAGAAA  CTTATTTATT  TCTATAATAC   240

CATGCAAAAA  AGTAAATATT  CTGTTCCATA  CTATTTAGT   AAATTATTTA  GCAAGTAAAT   300

TTTGGTGTAT  AAACAAAGTT  TATCTTAATA  TAAAAAATTA  CTTTACTTTT  ATACAGATTA   360

AAATGAAAAA  TTTTTTATGA  CAAGAAATAT  TGCCTTTAAT  TTATGAGGAA  ATAAGTAAAA   420

TTTTCTACAT  ACTTTATTTT  ATTGTTGAAA  TGTTCACTTA  TAAAAAAGGA  GAGATTAAAT   480

ATGAATATAA  AAAAAGAATT  TATAAAAGTA  ATTAGTATGT  CATGTTTAGT  AACAGCAATT   540

ACTTGAGTG   GTCCCGTCTT  TATCCCCCTT  GTACAGGGG   GCG  GGC  GGT  CAT  GGT   594
                                                 Ala  Gly  Gly  His  Gly
                                                  1                    5

GAT  GTA  GGT  ATG  CAC  GTA  AAA  GAG  AAA  GAG  AAA  AAT  AAA  GAT  GAG  AAT   642
Asp  Val  Gly  Met  His  Val  Lys  Glu  Lys  Glu  Lys  Asn  Lys  Asp  Glu  Asn
               10                    15                        20

AAG  AGA  AAA  GAT  GAA  GAA  CGA  AAT  AAA  ACA  CAG  GAA  GAG  CAT  TTA  AAG   690
Lys  Arg  Lys  Asp  Glu  Glu  Arg  Asn  Lys  Thr  Gln  Glu  Glu  His  Leu  Lys
               25                    30                        35

GAA  ATC  ATG  AAA  CAC  ATT  GTA  AAA  ATA  GAA  GTA  AAA  GGG  GAG  GAA  GCT   738
Glu  Ile  Met  Lys  His  Ile  Val  Lys  Ile  Glu  Val  Lys  Gly  Glu  Glu  Ala
               40                    45                        50

GTT  AAA  AAA  GAG  GCA  GCA  GAA  AAG  CTA  CTT  GAG  AAA  GTA  CCA  TCT  GAT   786
Val  Lys  Lys  Glu  Ala  Ala  Glu  Lys  Leu  Leu  Glu  Lys  Val  Pro  Ser  Asp
      55                    60                        65

GTT  TTA  GAG  ATG  TAT  AAA  GCA  ATT  GGA  GGA  AAG  ATA  TAT  ATT  GTG  GAT   834
Val  Leu  Glu  Met  Tyr  Lys  Ala  Ile  Gly  Gly  Lys  Ile  Tyr  Ile  Val  Asp
70                    75                        80                    85

GGT  GAT  ATT  ACA  AAA  CAT  ATA  TCT  TTA  GAA  GCA  TTA  TCT  GAA  GAT  AAG   882
Gly  Asp  Ile  Thr  Lys  His  Ile  Ser  Leu  Glu  Ala  Leu  Ser  Glu  Asp  Lys
               90                    95                        100
```

```
AAA AAA ATA AAA GAC ATT TAT GGG AAA GAT GCT TTA TTA CAT GAA CAT    930
Lys Lys Ile Lys Asp Ile Tyr Gly Lys Asp Ala Leu Leu His Glu His
        105             110                 115

TAT GTA TAT GCA AAA GAA GGA TAT GAA CCC GTA CTT GTA ATC CAA TCT    978
Tyr Val Tyr Ala Lys Glu Gly Tyr Glu Pro Val Leu Val Ile Gln Ser
        120             125                 130

TCG GAA GAT TAT GTA GAA AAT ACT GAA AAG GCA CTG AAC GTT TAT TAT   1026
Ser Glu Asp Tyr Val Glu Asn Thr Glu Lys Ala Leu Asn Val Tyr Tyr
        135             140                 145

GAA ATA GGT AAG ATA TTA TCA AGG GAT ATT TTA AGT AAA ATT AAT CAA   1074
Glu Ile Gly Lys Ile Leu Ser Arg Asp Ile Leu Ser Lys Ile Asn Gln
150             155                 160                 165

CCA TAT CAG AAA TTT TTA GAT GTA TTA AAT ACC ATT AAA AAT GCA TCT   1122
Pro Tyr Gln Lys Phe Leu Asp Val Leu Asn Thr Ile Lys Asn Ala Ser
                170             175                 180

GAT TCA GAT GGA CAA GAT CTT TTA TTT ACT AAT CAG CTT AAG GAA CAT   1170
Asp Ser Asp Gly Gln Asp Leu Leu Phe Thr Asn Gln Leu Lys Glu His
        185             190                 195

CCC ACA GAC TTT TCT GTA GAA TTC TTG GAA CAA AAT AGC AAT GAG TAT   1218
Pro Thr Asp Phe Ser Val Glu Phe Leu Glu Gln Asn Ser Asn Glu Val
        200             205                 210

CAA GAA GTA TTT GCG AAA GCT TTT GCA TAT TAT ATC GAG CCA CAG CAT   1266
Gln Glu Val Phe Ala Lys Ala Phe Ala Tyr Tyr Ile Glu Pro Gln His
        215             220                 225

CGT GAT GTT TTA CAG CTT TAT GCA CCG GAA GCT TTT AAT TAC ATG GAT   1314
Arg Asp Val Leu Gln Leu Tyr Ala Pro Glu Ala Phe Asn Tyr Met Asp
230             235                 240                 245

AAA TTT AAC GAA CAA GAA ATA AAT CTA TCC TTG GAA GAA CTT AAA GAT   1362
Lys Phe Asn Glu Gln Glu Ile Asn Leu Ser Leu Glu Glu Leu Lys Asp
                250             255                 260

CAA CGG ATG CTG TCA AGA TAT GAA AAA TGG GAA AAG ATA AAA CAG CAC   1410
Gln Arg Met Leu Ser Arg Tyr Glu Lys Trp Glu Lys Ile Lys Gln His
        265             270                 275

TAT CAA CAC TGG AGC GAT TCT TTA TCT GAA GAA GGA AGA GGA CTT TTA   1458
Tyr Gln His Trp Ser Asp Ser Leu Ser Glu Glu Gly Arg Gly Leu Leu
        280             285                 290

AAA AAG CTG CAG ATT CCT ATT GAG CCA AAG AAA GAT GAC ATA ATT CAT   1506
Lys Lys Leu Gln Ile Pro Ile Glu Pro Lys Lys Asp Asp Ile Ile His
295             300                 305

TCT TTA TCT CAA GAA GAA AAA GAG CTT CTA AAA AGA ATA CAA ATT GAT   1554
Ser Leu Ser Gln Glu Glu Lys Glu Leu Leu Lys Arg Ile Gln Ile Asp
310             315                 320                 325

AGT AGT GAT TTT TTA TCT ACT GAG GAA AAA GAG TTT TTA AAA AAG CTA   1602
Ser Ser Asp Phe Leu Ser Thr Glu Glu Lys Glu Phe Leu Lys Lys Leu
                330             335                 340

CAA ATT GAT ATT CGT GAT TCT TTA TCT GAA GAA GAA AAA GAG CTT TTA   1650
Gln Ile Asp Ile Arg Asp Ser Leu Ser Glu Glu Glu Lys Glu Leu Leu
                345             350                 355

AAT AGA ATA CAG GTG GAT AGT AGT AAT CCT TTA TCT GAA AAA GAA AAA   1698
Asn Arg Ile Gln Val Asp Ser Ser Asn Pro Leu Ser Glu Lys Glu Lys
        360             365                 370

GAG TTT TTA AAA AAG CTG AAA CTT GAT ATT CAA CCA TAT GAT ATT AAT   1746
Glu Phe Leu Lys Lys Leu Lys Leu Asp Ile Gln Pro Tyr Asp Ile Asn
        375             380                 385

CAA AGG TTG CAA GAT ACA GGA GGG TTA ATT GAT AGT CCG TCA ATT AAT   1794
Gln Arg Leu Gln Asp Thr Gly Gly Leu Ile Asp Ser Pro Ser Ile Asn
390             395                 400                 405

CTT GAT GTA AGA AAG CAG TAT AAA AGG GAT ATT CAA AAT ATT GAT GCT   1842
Leu Asp Val Arg Lys Gln Tyr Lys Arg Asp Ile Gln Asn Ile Asp Ala
                410             415                 420
```

| | | | | | | | | | | | | | | | | |
|---|---|---|---|---|---|---|---|---|---|---|---|---|---|---|---|---|
| TTA | TTA | CAT | CAA | TCC | ATT | GGA | AGT | ACC | TTG | TAC | AAT | AAA | ATT | TAT | TTG | 1890 |
| Leu | Leu | His | Gln | Ser | Ile | Gly | Ser | Thr | Leu | Tyr | Asn | Lys | Ile | Tyr | Leu | |
| | | | 425 | | | | 430 | | | | | | 435 | | | |
| TAT | GAA | AAT | ATG | AAT | ATC | AAT | AAC | CTT | ACA | GCA | ACC | CTA | GGT | GCG | GAT | 1938 |
| Tyr | Glu | Asn | Met | Asn | Ile | Asn | Asn | Leu | Thr | Ala | Thr | Leu | Gly | Ala | Asp | |
| | | 440 | | | | | 445 | | | | | 450 | | | | |
| TTA | GTT | GAT | TCC | ACT | GAT | AAT | ACT | AAA | ATT | AAT | AGA | GGT | ATT | TTC | AAT | 1986 |
| Leu | Val | Asp | Ser | Thr | Asp | Asn | Thr | Lys | Ile | Asn | Arg | Gly | Ile | Phe | Asn | |
| 455 | | | | | 460 | | | | | 465 | | | | | | |
| GAA | TTC | AAA | AAA | AAT | TTC | AAA | TAT | AGT | ATT | TCT | AGT | AAC | TAT | ATG | ATT | 2034 |
| Glu | Phe | Lys | Lys | Asn | Phe | Lys | Tyr | Ser | Ile | Ser | Ser | Asn | Tyr | Met | Ile | |
| 470 | | | | | 475 | | | | | 480 | | | | | 485 | |
| GTT | GAT | ATA | AAT | GAA | AGG | CCT | GCA | TTA | GAT | AAT | GAG | CGT | TTG | AAA | TGG | 2082 |
| Val | Asp | Ile | Asn | Glu | Arg | Pro | Ala | Leu | Asp | Asn | Glu | Arg | Leu | Lys | Trp | |
| | | | | 490 | | | | | 495 | | | | | 500 | | |
| AGA | ATC | CAA | TTA | TCA | CCA | GAT | ACT | CGA | GCA | GGA | TAT | TTA | GAA | AAT | GGA | 2130 |
| Arg | Ile | Gln | Leu | Ser | Pro | Asp | Thr | Arg | Ala | Gly | Tyr | Leu | Glu | Asn | Gly | |
| | | | 505 | | | | 510 | | | | | 515 | | | | |
| AAG | CTT | ATA | TTA | CAA | AGA | AAC | ATC | GGT | CTG | GAA | ATA | AAG | GAT | GTA | CAA | 2178 |
| Lys | Leu | Ile | Leu | Gln | Arg | Asn | Ile | Gly | Leu | Glu | Ile | Lys | Asp | Val | Gln | |
| | | 520 | | | | | 525 | | | | | 530 | | | | |
| ATA | ATT | AAG | CAA | TCC | GAA | AAA | GAA | TAT | ATA | AGG | ATT | GAT | GCG | AAA | GTA | 2226 |
| Ile | Ile | Lys | Gln | Ser | Glu | Lys | Glu | Tyr | Ile | Arg | Ile | Asp | Ala | Lys | Val | |
| 535 | | | | | 540 | | | | | 545 | | | | | | |
| GTG | CCA | AAG | AGT | AAA | ATA | GAT | ACA | AAA | ATT | CAA | GAA | GCA | CAG | TTA | AAT | 2274 |
| Val | Pro | Lys | Ser | Lys | Ile | Asp | Thr | Lys | Ile | Gln | Glu | Ala | Gln | Leu | Asn | |
| 550 | | | | | 555 | | | | | 560 | | | | | 565 | |
| ATA | AAT | CAG | GAA | TGG | AAT | AAA | GCA | TTA | GGG | TTA | CCA | AAA | TAT | ACA | AAG | 2322 |
| Ile | Asn | Gln | Glu | Trp | Asn | Lys | Ala | Leu | Gly | Leu | Pro | Lys | Tyr | Thr | Lys | |
| | | | | 570 | | | | | 575 | | | | | 580 | | |
| CTT | ATT | ACA | TTC | AAC | GTG | CAT | AAT | AGA | TAT | GCA | TCC | AAT | ATT | GTA | GAA | 2370 |
| Leu | Ile | Thr | Phe | Asn | Val | His | Asn | Arg | Tyr | Ala | Ser | Asn | Ile | Val | Glu | |
| | | | 585 | | | | | 590 | | | | | 595 | | | |
| AGT | GCT | TAT | TTA | ATA | TTG | AAT | GAA | TGG | AAA | AAT | AAT | ATT | CAA | AGT | GAT | 2418 |
| Ser | Ala | Tyr | Leu | Ile | Leu | Asn | Glu | Trp | Lys | Asn | Asn | Ile | Gln | Ser | Asp | |
| | | 600 | | | | | 605 | | | | | 610 | | | | |
| CTT | ATA | AAA | AAG | GTA | ACA | AAT | TAC | TTA | GTT | GAT | GGT | AAT | GGA | AGA | TTT | 2466 |
| Leu | Ile | Lys | Lys | Val | Thr | Asn | Tyr | Leu | Val | Asp | Gly | Asn | Gly | Arg | Phe | |
| 615 | | | | | 620 | | | | | 625 | | | | | | |
| GTT | TTT | ACC | GAT | ATT | ACT | CTC | CCT | AAT | ATA | GCT | GAA | CAA | TAT | ACA | CAT | 2514 |
| Val | Phe | Thr | Asp | Ile | Thr | Leu | Pro | Asn | Ile | Ala | Glu | Gln | Tyr | Thr | His | |
| 630 | | | | | 635 | | | | | 640 | | | | | 645 | |
| CAA | GAT | GAG | ATA | TAT | GAG | CAA | GTT | CAT | TCA | AAA | GGG | TTA | TAT | GTT | CCA | 2562 |
| Gln | Asp | Glu | Ile | Tyr | Glu | Gln | Val | His | Ser | Lys | Gly | Leu | Tyr | Val | Pro | |
| | | | | 650 | | | | | 655 | | | | | 660 | | |
| GAA | TCC | CGT | TCT | ATA | TTA | CTC | CAT | GGA | CCT | TCA | AAA | GGT | GTA | GAA | TTA | 2610 |
| Glu | Ser | Arg | Ser | Ile | Leu | Leu | His | Gly | Pro | Ser | Lys | Gly | Val | Glu | Leu | |
| | | | 665 | | | | | 670 | | | | | 675 | | | |
| AGG | AAT | GAT | AGT | GAG | GGT | TTT | ATA | CAC | GAA | TTT | GGA | CAT | GCT | GTG | GAT | 2658 |
| Arg | Asn | Asp | Ser | Glu | Gly | Phe | Ile | His | Glu | Phe | Gly | His | Ala | Val | Asp | |
| | | | 680 | | | | | 685 | | | | | 690 | | | |
| GAT | TAT | GCT | GGA | TAT | CTA | TTA | GAT | AAG | AAC | CAA | TCT | GAT | TTA | GTT | ACA | 2706 |
| Asp | Tyr | Ala | Gly | Tyr | Leu | Leu | Asp | Lys | Asn | Gln | Ser | Asp | Leu | Val | Thr | |
| | | 695 | | | | | 700 | | | | | 705 | | | | |
| AAT | TCT | AAA | AAA | TTC | ATT | GAT | ATT | TTT | AAG | GAA | GAA | GGG | AGT | AAT | TTA | 2754 |
| Asn | Ser | Lys | Lys | Phe | Ile | Asp | Ile | Phe | Lys | Glu | Glu | Gly | Ser | Asn | Leu | |
| 710 | | | | | 715 | | | | | 720 | | | | | 725 | |
| ACT | TCG | TAT | GGG | AGA | ACA | AAT | GAA | GCG | GAA | TTT | TTT | GCA | GAA | GCC | TTT | 2802 |
| Thr | Ser | Tyr | Gly | Arg | Thr | Asn | Glu | Ala | Glu | Phe | Phe | Ala | Glu | Ala | Phe | |
| | | | | 730 | | | | | 735 | | | | | 740 | | |

```
AGG TTA ATG CAT TCT ACG GAC CAT GCT GAA CGT TTA AAA GTT CAA AAA       2850
Arg Leu Met His Ser Thr Asp His Ala Glu Arg Leu Lys Val Gln Lys
            745                 750                 755

AAT GCT CCG AAA ACT TTC CAA TTT ATT AAC GAT CAG ATT AAG TTC ATT       2898
Asn Ala Pro Lys Thr Phe Gln Phe Ile Asn Asp Gln Ile Lys Phe Ile
        760                 765                 770

ATT AAC TCA TAAGTAATGT ATTAAAAATT TTCAAATGGA TTTAATAATA               2947
Ile Asn Ser
    775

ATAATAATAA TAATAATAAC GGGACCAGCC ATTATGAAGC AACTAATTCT AGACTTGATA     3007

GTAATTCTTG GAAGCACCA GATAGTGTAA AAGGTGGCAT TGCCAGAATG ATATTTTATG      3067

TGTTCGTTAG ATATGAAGGC AAAAACAATG ATCCTGACCT AGAACTAAT GATAATGTTA      3127

TTAATAATTT AATGCCTTTT ATAGGAATAT TAGTAAAAGT GCCGAAAAGA TCCTGTTGCA     3187

AAGCTTTTAA AGAACATATT ATTCTATCAA GTGGCTGTAT ATTTTGTGTA ATTTCAATA      3247

AATTTTGTAA TTAAGCATAC GTCAAAAAAC CGAAATCTGA GCTC                     3291
```

( 2 ) INFORMATION FOR SEQ ID NO:2:

( i ) SEQUENCE CHARACTERISTICS:
        ( A ) LENGTH: 776 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala Gly Gly His Gly Asp Val Gly Met His Val Lys Glu Lys Glu Lys
 1               5                   10                  15

Asn Lys Asp Glu Asn Lys Arg Lys Asp Glu Glu Arg Asn Lys Thr Gln
                20                  25                  30

Glu Glu His Leu Lys Glu Ile Met Lys His Ile Val Lys Ile Glu Val
            35                  40                  45

Lys Gly Glu Glu Ala Val Lys Lys Glu Ala Ala Glu Lys Leu Leu Glu
        50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
```

|   | 225 |   |   |   |   | 230 |   |   |   |   | 235 |   |   |   |   | 240 |
|---|---|---|---|---|---|---|---|---|---|---|---|---|---|---|---|---|

Phe Asn Tyr Met Asp Lys Phe Asn Glu Gln Glu Ile Asn Leu Ser Leu
              245                 250                 255

Glu Glu Leu Lys Asp Gln Arg Met Leu Ser Arg Tyr Glu Lys Trp Glu
              260                 265                 270

Lys Ile Lys Gln His Tyr Gln His Trp Ser Asp Ser Leu Ser Glu Glu
          275             280             285

Gly Arg Gly Leu Leu Lys Lys Leu Gln Ile Pro Ile Glu Pro Lys Lys
    290             295             300

Asp Asp Ile Ile His Ser Leu Ser Gln Glu Glu Lys Glu Leu Leu Lys
305             310             315             320

Arg Ile Gln Ile Asp Ser Ser Asp Phe Leu Ser Thr Glu Glu Lys Glu
              325             330             335

Phe Leu Lys Lys Leu Gln Ile Asp Ile Arg Asp Ser Leu Ser Glu Glu
          340             345             350

Glu Lys Glu Leu Leu Asn Arg Ile Gln Val Asp Ser Ser Asn Pro Leu
          355             360             365

Ser Glu Lys Glu Lys Glu Phe Leu Lys Lys Leu Lys Leu Asp Ile Gln
      370             375             380

Pro Tyr Asp Ile Asn Gln Arg Leu Gln Asp Thr Gly Gly Leu Ile Asp
385             390             395             400

Ser Pro Ser Ile Asn Leu Asp Val Arg Lys Gln Tyr Lys Arg Asp Ile
              405             410             415

Gln Asn Ile Asp Ala Leu Leu His Gln Ser Ile Gly Ser Thr Leu Tyr
              420             425             430

Asn Lys Ile Tyr Leu Tyr Glu Asn Met Asn Ile Asn Asn Leu Thr Ala
          435             440             445

Thr Leu Gly Ala Asp Leu Val Asp Ser Thr Asp Asn Thr Lys Ile Asn
    450             455             460

Arg Gly Ile Phe Asn Glu Phe Lys Lys Asn Phe Lys Tyr Ser Ile Ser
465             470             475             480

Ser Asn Tyr Met Ile Val Asp Ile Asn Glu Arg Pro Ala Leu Asp Asn
              485             490             495

Glu Arg Leu Lys Trp Arg Ile Gln Leu Ser Pro Asp Thr Arg Ala Gly
          500             505             510

Tyr Leu Glu Asn Gly Lys Leu Ile Leu Gln Arg Asn Ile Gly Leu Glu
      515             520             525

Ile Lys Asp Val Gln Ile Ile Lys Gln Ser Glu Lys Glu Tyr Ile Arg
    530             535             540

Ile Asp Ala Lys Val Val Pro Lys Ser Lys Ile Asp Thr Lys Ile Gln
545             550             555             560

Glu Ala Gln Leu Asn Ile Asn Gln Glu Trp Asn Lys Ala Leu Gly Leu
              565             570             575

Pro Lys Tyr Thr Lys Leu Ile Thr Phe Asn Val His Asn Arg Tyr Ala
          580             585             590

Ser Asn Ile Val Glu Ser Ala Tyr Leu Ile Leu Asn Glu Trp Lys Asn
      595             600             605

Asn Ile Gln Ser Asp Leu Ile Lys Lys Val Thr Asn Tyr Leu Val Asp
    610             615             620

Gly Asn Gly Arg Phe Val Phe Thr Asp Ile Thr Leu Pro Asn Ile Ala
625             630             635             640

Glu Gln Tyr Thr His Gln Asp Glu Ile Tyr Glu Gln Val His Ser Lys
              645             650             655

-continued

Gly Leu Tyr Val Pro Glu Ser Arg Ser Ile Leu Leu His Gly Pro Ser
660 665 670

Lys Gly Val Glu Leu Arg Asn Asp Ser Glu Gly Phe Ile His Glu Phe
675 680 685

Gly His Ala Val Asp Asp Tyr Ala Gly Tyr Leu Leu Asp Lys Asn Gln
690 695 700

Ser Asp Leu Val Thr Asn Ser Lys Lys Phe Ile Asp Ile Phe Lys Glu
705 710 715 720

Glu Gly Ser Asn Leu Thr Ser Tyr Gly Arg Thr Asn Glu Ala Glu Phe
725 730 735

Phe Ala Glu Ala Phe Arg Leu Met His Ser Thr Asp His Ala Glu Arg
740 745 750

Leu Lys Val Gln Lys Asn Ala Pro Lys Thr Phe Gln Phe Ile Asn Asp
755 760 765

Gln Ile Lys Phe Ile Ile Asn Ser
770 775

( 2 ) INFORMATION FOR SEQ ID NO:3:

( i ) SEQUENCE CHARACTERISTICS:
( A ) LENGTH: 4235 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus anthracis ( i x ) FEATURE:
( A ) NAME/KEY: CDS
( B ) LOCATION: 1891..4095

( x i ) SEQUENCE DESCRIPTION: SEQ ID NO:3:

AAGCTTCTGT CATTCGTAAA TTTCAAATAG AACGTAAATT TAGACTTCTC ATCATTAAAA 60

ATGAAAAATC TTATCTTTTT GATTCTATTG TATATTTTTA TTAAGGTGTT TAATAGTTAG 120

AAAAGACAGT TGATGCTATT ACTCCAGATA AAATATAGCT AACCATAAAT TTATTAAAGA 180

AACCTTGTTG TTCTAAATAA TGATTTTGTG GATTCCGGAA TAGATACTGG TGAGTTAGCT 240

CTAATTTTAT AGTGATTTAA CTAACAATTT ATAAAGCAGC ATAATTCAAA TTTTTTAATT 300

GATTTTTCCT GAAGCATAGT ATAAAAGAGT CAAGGTCTTC TAGACTTGAC TCTTGGAATC 360

ATTAGGAATT AACAATATAT ATAATGCGCT AGACAGAATC AAATTAAATG CAAAAATGAA 420

TATTTTAGTA AGAGATCCAT ATCATTATGA TAATAACGGT AATATTGTAG GGGTTGATGA 480

TTCATATTTA AAAAACGCAT ATAAGCAAAT ACTTAATTGG TCAAGCGATG GAGTTTCTTT 540

AAATCTAGAT GAAGATGTAA ATCAAGCACT ATCTGGATAT ATGCTTCAAA TAAAAAAACC 600

TTCAAACCAC CTAACAAACA GCCCAGTTAC AATTACATTA GCAGGCAAGG ACAGTGGTGT 660

TGGAGAATTG TATAGAGTAT TATCAGATGG AGCAGGATTC CTGGATTTCA ATAAGTTTGA 720

TGAAAATTGG CGATCATTAG TAGATCCTGG TGATGATGTT TATGTGTATG CTGTTACTAA 780

AGAAGATTTT AATGCAGTTA CTCGAGATGA AAATGGTAAT ATAGCGAATA AATTAAAAAA 840

CACCTTAGTT TTATCGGGTA AAATAAAAGA AATAAACATA AAAACTACAA ATATTAATAT 900

ATTTGTAGTT TTTATGTTTA TTATATACCT CCTATTTTAT ATTATTAGTA GCACAGTTTT 960

TGCAAATCAT GTAATTGTAT ACTTATCTAT GTAGAGGTAT CACAACTTAT GAATAGTGTA 1020

TTTTATTGAA CGTTGGTTAG CTTGGACAGT TGTATGGATA TGCATACTTT ATAACGTATA 1080

| | |
|---|---|
| AAATTTCACG CACCACAATA AAACTAATTT AACAAAAACA AAAACACACC TAAGATCATT | 1140 |
| CAGTTCTTTT AATAAGGAGC TGCCCACCAA GCTAAACCTA AATAATCTTT GTTTCACATA | 1200 |
| AGGTTTTTTT CTAAATATAC AGTGTAAGTT ATTGTGAATT TAACCAGTAT ATATTAAAAA | 1260 |
| TGTTTTATGT TAACAAATTA AATTGTAAAA CCCCTCTTAA GCATAGTTAA GAGGGGTAGG | 1320 |
| TTTTAAATTT TTTGTTGAAA TTAGAAAAAA TAATAAAAAA ACAAACCTAT TTTCTTTCAG | 1380 |
| GTTGTTTTTG GGTTACAAAA CAAAAAGAAA ACATGTTTCA AGGTACAATA ATTATGGTTC | 1440 |
| TTTAGCTTTC TGTAAAACAG CCTTAATAGT TGGATTTATG ACTATTAAAG TTAGTATACA | 1500 |
| GCATACACAA TCTATTGAAG GATATTTATA ATGCAATTCC CTAAAAATAG TTTTGTATAA | 1560 |
| CCAGTTCTTT TATCCGAACT GATACACGTA TTTTAGCATA ATTTTTAATG TATCTTCAAA | 1620 |
| AACAGCTTCT GTGTCCTTTT CTATTAAACA TATAAATTCT TTTTTATGTT ATATATTTAT | 1680 |
| AAAAGTTCTG TTTAAAAAGC CAAAAATAAA TAATTATCTC TTTTTATTTA TATTATATTG | 1740 |
| AAACTAAAGT TTATTAATTT CAATATAATA TAAATTTAAT TTTATACAAA AAGGAGAACG | 1800 |
| TATATGAAAA AACGAAAAGT GTTAATACCA TTAATGGCAT TGTCTACGAT ATTAGTTTCA | 1860 |

| | | |
|---|---|---|
| AGCACAGGTA ATTTAGAGGT GATTCAGGCA | GAA GTT AAA CAG GAG AAC CGG TTA<br>Glu Val Lys Gln Glu Asn Arg Leu<br>1               5 | 1914 |

| | | |
|---|---|---|
| TTA AAT GAA TCA GAA TCA AGT TCC CAG GGG TTA CTA GGA TAC TAT TTT<br>Leu Asn Glu Ser Glu Ser Ser Gln Gly Leu Leu Gly Tyr Tyr Phe<br>        10                  15                    20 | | 1962 |
| AGT GAT TTG AAT TTT CAA GCA CCC ATG GTG GTT ACC TCT TCT ACT ACA<br>Ser Asp Leu Asn Phe Gln Ala Pro Met Val Val Thr Ser Ser Thr Thr<br>25                    30                   35                  40 | | 2010 |
| GGG GAT TTA TCT ATT CCT AGT TCT GAG TTA GAA AAT ATT CCA TCG GAA<br>Gly Asp Leu Ser Ile Pro Ser Ser Glu Leu Glu Asn Ile Pro Ser Glu<br>              45                  50                  55 | | 2058 |
| AAC CAA TAT TTT CAA TCT GCT ATT TGG TCA GGA TTT ATC AAA GTT AAG<br>Asn Gln Tyr Phe Gln Ser Ala Ile Trp Ser Gly Phe Ile Lys Val Lys<br>                60                  65                  70 | | 2106 |
| AAG AGT GAT GAA TAT ACA TTT GCT ACT TCC GCT GAT AAT CAT GTA ACA<br>Lys Ser Asp Glu Tyr Thr Phe Ala Thr Ser Ala Asp Asn His Val Thr<br>        75                  80                  85 | | 2154 |
| ATG TGG GTA GAT GAC CAA GAA GTG ATT AAT AAA GCT TCT AAT TCT AAC<br>Met Trp Val Asp Asp Gln Glu Val Ile Asn Lys Ala Ser Asn Ser Asn<br>         90                  95                 100 | | 2202 |
| AAA ATC AGA TTA GAA AAA GGA AGA TTA TAT CAA ATA AAA ATT CAA TAT<br>Lys Ile Arg Leu Glu Lys Gly Arg Leu Tyr Gln Ile Lys Ile Gln Tyr<br>105                  110                 115                 120 | | 2250 |
| CAA CGA GAA AAT CCT ACT GAA AAA GGA TTG GAT TTC AAG TTG TAC TGG<br>Gln Arg Glu Asn Pro Thr Glu Lys Gly Leu Asp Phe Lys Leu Tyr Trp<br>                125                 130                 135 | | 2298 |
| ACC GAT TCT CAA AAT AAA AAA GAA GTG ATT TCT AGT GAT AAC TTA CAA<br>Thr Asp Ser Gln Asn Lys Lys Glu Val Ile Ser Ser Asp Asn Leu Gln<br>                140                 145                 150 | | 2346 |
| TTG CCA GAA TTA AAA CAA AAA TCT TCG AAC TCA AGA AAA AAG CGA AGT<br>Leu Pro Glu Leu Lys Gln Lys Ser Ser Asn Ser Arg Lys Lys Arg Ser<br>            155                 160                 165 | | 2394 |
| ACA AGT GCT GGA CCT ACG GTT CCA GAC CGT GAC AAT GAT GGA ATC CCT<br>Thr Ser Ala Gly Pro Thr Val Pro Asp Arg Asp Asn Asp Gly Ile Pro<br>        170                 175                 180 | | 2442 |
| GAT TCA TTA GAG GTA GAA GGA TAT ACG GTT GAT GTC AAA AAT AAA AGA<br>Asp Ser Leu Glu Val Glu Gly Tyr Thr Val Asp Val Lys Asn Lys Arg<br>185                 190                 195                 200 | | 2490 |
| ACT TTT CTT TCA CCA TGG ATT TCT AAT ATT CAT GAA AAG AAA GGA TTA<br>Thr Phe Leu Ser Pro Trp Ile Ser Asn Ile His Glu Lys Lys Gly Leu | | 2538 |

|  |  |  |  |  |  | 205 |  |  |  |  | 210 |  |  |  |  | 215 |  |  |
|---|---|---|---|---|---|---|---|---|---|---|---|---|---|---|---|---|---|---|
| ACC<br>Thr | AAA<br>Lys | TAT<br>Tyr | AAA<br>Lys<br>220 | TCA<br>Ser | TCT<br>Ser | CCT<br>Pro | GAA<br>Glu | AAA<br>Lys<br>225 | TGG<br>Trp | AGC<br>Ser | ACG<br>Thr | GCT<br>Ala | TCT<br>Ser<br>230 | GAT<br>Asp | CCG<br>Pro | | | 2586 |
| TAC<br>Tyr | AGT<br>Ser | GAT<br>Asp<br>235 | TTC<br>Phe | GAA<br>Glu | AAG<br>Lys | GTT<br>Val | ACA<br>Thr<br>240 | GGA<br>Gly | CGG<br>Arg | ATT<br>Ile | GAT<br>Asp | AAG<br>Lys<br>245 | AAT<br>Asn | GTA<br>Val | TCA<br>Ser | | | 2634 |
| CCA<br>Pro | GAG<br>Glu<br>250 | GCA<br>Ala | AGA<br>Arg | CAC<br>His | CCC<br>Pro | CTT<br>Leu<br>255 | GTG<br>Val | GCA<br>Ala | GCT<br>Ala | TAT<br>Tyr | CCG<br>Pro<br>260 | ATT<br>Ile | GTA<br>Val | CAT<br>His | GTA<br>Val | | | 2682 |
| GAT<br>Asp<br>265 | ATG<br>Met | GAG<br>Glu | AAT<br>Asn | ATT<br>Ile | ATT<br>Ile<br>270 | CTC<br>Leu | TCA<br>Ser | AAA<br>Lys | AAT<br>Asn | GAG<br>Glu<br>275 | GAT<br>Asp | CAA<br>Gln | TCC<br>Ser | ACA<br>Thr | CAG<br>Gln<br>280 | | | 2730 |
| AAT<br>Asn | ACT<br>Thr | GAT<br>Asp | AGT<br>Ser | GAA<br>Glu<br>285 | ACG<br>Thr | AGA<br>Arg | ACA<br>Thr | ATA<br>Ile | AGT<br>Ser<br>290 | AAA<br>Lys | AAT<br>Asn | ACT<br>Thr | TCT<br>Ser | ACA<br>Thr<br>295 | AGT<br>Ser | | | 2778 |
| AGG<br>Arg | ACA<br>Thr | CAT<br>His | ACT<br>Thr<br>300 | AGT<br>Ser | GAA<br>Glu | GTA<br>Val | CAT<br>His | GGA<br>Gly<br>305 | AAT<br>Asn | GCA<br>Ala | GAA<br>Glu | GTG<br>Val | CAT<br>His<br>310 | GCG<br>Ala | TCG<br>Ser | | | 2826 |
| TTC<br>Phe | TTT<br>Phe | GAT<br>Asp<br>315 | ATT<br>Ile | GGT<br>Gly | GGG<br>Gly | AGT<br>Ser | GTA<br>Val<br>320 | TCT<br>Ser | GCA<br>Ala | GGA<br>Gly | TTT<br>Phe | AGT<br>Ser<br>325 | AAT<br>Asn | TCG<br>Ser | AAT<br>Asn | | | 2874 |
| TCA<br>Ser | AGT<br>Ser<br>330 | ACG<br>Thr | GTC<br>Val | GCA<br>Ala | ATT<br>Ile | GAT<br>Asp<br>335 | CAT<br>His | TCA<br>Ser | CTA<br>Leu | TCT<br>Ser | CTA<br>Leu<br>340 | GCA<br>Ala | GGG<br>Gly | GAA<br>Glu | AGA<br>Arg | | | 2922 |
| ACT<br>Thr<br>345 | TGG<br>Trp | GCT<br>Ala | GAA<br>Glu | ACA<br>Thr<br>350 | ATG<br>Met | GGT<br>Gly | TTA<br>Leu | AAT<br>Asn | ACC<br>Thr<br>355 | GCT<br>Ala | GAT<br>Asp | ACA<br>Thr | GCA<br>Ala | AGA<br>Arg<br>360 | TTA<br>Leu | | | 2970 |
| AAT<br>Asn | GCC<br>Ala | AAT<br>Asn | ATT<br>Ile | AGA<br>Arg<br>365 | TAT<br>Tyr | GTA<br>Val | AAT<br>Asn | ACT<br>Thr | GGG<br>Gly<br>370 | ACG<br>Thr | GCT<br>Ala | CCA<br>Pro | ATC<br>Ile | TAC<br>Tyr<br>375 | AAC<br>Asn | | | 3018 |
| GTG<br>Val | TTA<br>Leu | CCA<br>Pro | ACG<br>Thr<br>380 | ACT<br>Thr | TCG<br>Ser | TTA<br>Leu | GTG<br>Val | TTA<br>Leu<br>385 | GGA<br>Gly | AAA<br>Lys | AAT<br>Asn | CAA<br>Gln | ACA<br>Thr<br>390 | CTC<br>Leu | GCG<br>Ala | | | 3066 |
| ACA<br>Thr | ATT<br>Ile | AAA<br>Lys<br>395 | GCT<br>Ala | AAG<br>Lys | GAA<br>Glu | AAC<br>Asn | CAA<br>Gln<br>400 | TTA<br>Leu | AGT<br>Ser | CAA<br>Gln | ATA<br>Ile | CTT<br>Leu<br>405 | GCA<br>Ala | CCT<br>Pro | AAT<br>Asn | | | 3114 |
| AAT<br>Asn | TAT<br>Tyr<br>410 | TAT<br>Tyr | CCT<br>Pro | TCT<br>Ser | AAA<br>Lys<br>415 | AAC<br>Asn | TTG<br>Leu | GCG<br>Ala | CCA<br>Pro | ATC<br>Ile<br>420 | GCA<br>Ala | TTA<br>Leu | AAT<br>Asn | GCA<br>Ala | CAA<br>Gln | | | 3162 |
| GAC<br>Asp<br>425 | GAT<br>Asp | TTC<br>Phe | AGT<br>Ser | TCT<br>Ser | ACT<br>Thr<br>430 | CCA<br>Pro | ATT<br>Ile | ACA<br>Thr | ATG<br>Met | AAT<br>Asn<br>435 | TAC<br>Tyr | AAT<br>Asn | CAA<br>Gln | TTT<br>Phe | CTT<br>Leu<br>440 | | | 3210 |
| GAG<br>Glu | TTA<br>Leu | GAA<br>Glu | AAA<br>Lys | ACG<br>Thr<br>445 | AAA<br>Lys | CAA<br>Gln | TTA<br>Leu | AGA<br>Arg | TTA<br>Leu<br>450 | GAT<br>Asp | ACG<br>Thr | GAT<br>Asp | CAA<br>Gln | GTA<br>Val<br>455 | TAT<br>Tyr | | | 3258 |
| GGG<br>Gly | AAT<br>Asn | ATA<br>Ile | GCA<br>Ala<br>460 | ACA<br>Thr | TAC<br>Tyr | AAT<br>Asn | TTT<br>Phe | GAA<br>Glu<br>465 | AAT<br>Asn | GGA<br>Gly | AGA<br>Arg | GTG<br>Val | AGG<br>Arg<br>470 | GTG<br>Val | GAT<br>Asp | | | 3306 |
| ACA<br>Thr | GGC<br>Gly | TCG<br>Ser<br>475 | AAC<br>Asn | TGG<br>Trp | AGT<br>Ser | GAA<br>Glu<br>480 | GTG<br>Val | TTA<br>Leu | CCG<br>Pro | CAA<br>Gln | ATT<br>Ile<br>485 | CAA<br>Gln | GAA<br>Glu | ACA<br>Thr | ACT<br>Thr | | | 3354 |
| GCA<br>Ala | CGT<br>Arg<br>490 | ATC<br>Ile | ATT<br>Ile | TTT<br>Phe | AAT<br>Asn<br>495 | GGA<br>Gly | AAA<br>Lys | GAT<br>Asp | TTA<br>Leu | AAT<br>Asn<br>500 | CTG<br>Leu | GTA<br>Val | GAA<br>Glu | AGG<br>Arg | CGG<br>Arg | | | 3402 |
| ATA<br>Ile<br>505 | GCG<br>Ala | GCG<br>Ala | GTT<br>Val | AAT<br>Asn | CCT<br>Pro<br>510 | AGT<br>Ser | GAT<br>Asp | CCA<br>Pro | TTA<br>Leu | GAA<br>Glu<br>515 | ACG<br>Thr | ACT<br>Thr | AAA<br>Lys | CCG<br>Pro | GAT<br>Asp<br>520 | | | 3450 |
| ATG<br>Met | ACA<br>Thr | TTA<br>Leu | AAA<br>Lys | GAA<br>Glu | GCC<br>Ala | CTT<br>Leu | AAA<br>Lys | ATA<br>Ile | GCA<br>Ala | TTT<br>Phe | GGA<br>Gly | TTT<br>Phe | AAC<br>Asn | GAA<br>Glu | CCG<br>Pro | | | 3498 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 525 |     |     |     |     | 530 |     |     |     |     | 535 |     |     |
| AAT | GGA | AAC | TTA | CAA | TAT | CAA | GGG | AAA | GAC | ATA | ACC | GAA | TTT | GAT | TTT | 3546 |
| Asn | Gly | Asn | Leu | Gln | Tyr | Gln | Gly | Lys | Asp | Ile | Thr | Glu | Phe | Asp | Phe |     |
|     |     |     | 540 |     |     |     |     | 545 |     |     |     |     | 550 |     |     |     |
| AAT | TTC | GAT | CAA | CAA | ACA | TCT | CAA | AAT | ATC | AAG | AAT | CAG | TTA | GCG | GAA | 3594 |
| Asn | Phe | Asp | Gln | Gln | Thr | Ser | Gln | Asn | Ile | Lys | Asn | Gln | Leu | Ala | Glu |     |
|     |     | 555 |     |     |     |     | 560 |     |     |     |     | 565 |     |     |     |     |
| TTA | AAC | GCA | ACT | AAC | ATA | TAT | ACT | GTA | TTA | GAT | AAA | ATC | AAA | TTA | AAT | 3642 |
| Leu | Asn | Ala | Thr | Asn | Ile | Tyr | Thr | Val | Leu | Asp | Lys | Ile | Lys | Leu | Asn |     |
|     | 570 |     |     |     |     | 575 |     |     |     |     | 580 |     |     |     |     |     |
| GCA | AAA | ATG | AAT | ATT | TTA | ATA | AGA | GAT | AAA | CGT | TTT | CAT | TAT | GAT | AGA | 3690 |
| Ala | Lys | Met | Asn | Ile | Leu | Ile | Arg | Asp | Lys | Arg | Phe | His | Tyr | Asp | Arg |     |
| 585 |     |     |     |     | 590 |     |     |     |     | 595 |     |     |     |     | 600 |     |
| AAT | AAC | ATA | GCA | GTT | GGG | GCG | GAT | GAG | TCA | GTA | GTT | AAG | GAG | GCT | CAT | 3738 |
| Asn | Asn | Ile | Ala | Val | Gly | Ala | Asp | Glu | Ser | Val | Val | Lys | Glu | Ala | His |     |
|     |     |     |     |     | 605 |     |     |     | 610 |     |     |     |     | 615 |     |     |
| AGA | GAA | GTA | ATT | AAT | TCG | TCA | ACA | GAG | GGA | TTA | TTG | TTA | AAT | ATT | GAT | 3786 |
| Arg | Glu | Val | Ile | Asn | Ser | Ser | Thr | Glu | Gly | Leu | Leu | Leu | Asn | Ile | Asp |     |
|     |     |     | 620 |     |     |     |     | 625 |     |     |     |     | 630 |     |     |     |
| AAG | GAT | ATA | AGA | AAA | ATA | TTA | TCA | GGT | TAT | ATT | GTA | GAA | ATT | GAA | GAT | 3834 |
| Lys | Asp | Ile | Arg | Lys | Ile | Leu | Ser | Gly | Tyr | Ile | Val | Glu | Ile | Glu | Asp |     |
|     |     | 635 |     |     |     |     | 640 |     |     |     |     | 645 |     |     |     |     |
| ACT | GAA | GGG | CTT | AAA | GAA | GTT | ATA | AAT | GAC | AGA | TAT | GAT | ATG | TTG | AAT | 3882 |
| Thr | Glu | Gly | Leu | Lys | Glu | Val | Ile | Asn | Asp | Arg | Tyr | Asp | Met | Leu | Asn |     |
|     | 650 |     |     |     |     | 655 |     |     |     |     | 660 |     |     |     |     |     |
| ATT | TCT | AGT | TTA | CGG | CAA | GAT | GGA | AAA | ACA | TTT | ATA | GAT | TTT | AAA | AAA | 3930 |
| Ile | Ser | Ser | Leu | Arg | Gln | Asp | Gly | Lys | Thr | Phe | Ile | Asp | Phe | Lys | Lys |     |
| 665 |     |     |     |     | 670 |     |     |     |     | 675 |     |     |     |     | 680 |     |
| TAT | AAT | GAT | AAA | TTA | CCG | TTA | TAT | ATA | AGT | AAT | CCC | AAT | TAT | AAG | GTA | 3978 |
| Tyr | Asn | Asp | Lys | Leu | Pro | Leu | Tyr | Ile | Ser | Asn | Pro | Asn | Tyr | Lys | Val |     |
|     |     |     |     | 685 |     |     |     |     | 690 |     |     |     |     | 695 |     |     |
| AAT | GTA | TAT | GCT | GTT | ACT | AAA | GAA | AAC | ACT | ATT | ATT | AAT | CCT | AGT | GAG | 4026 |
| Asn | Val | Tyr | Ala | Val | Thr | Lys | Glu | Asn | Thr | Ile | Ile | Asn | Pro | Ser | Glu |     |
|     |     |     | 700 |     |     |     |     | 705 |     |     |     |     | 710 |     |     |     |
| AAT | GGG | GAT | ACT | AGT | ACC | AAC | GGG | ATC | AAG | AAA | ATT | TTA | ATC | TTT | TCT | 4074 |
| Asn | Gly | Asp | Thr | Ser | Thr | Asn | Gly | Ile | Lys | Lys | Ile | Leu | Ile | Phe | Ser |     |
|     |     | 715 |     |     |     |     | 720 |     |     |     |     | 725 |     |     |     |     |
| AAA | AAA | GGC | TAT | GAG | ATA | GGA | TAAGGTAATT | CTAGGTGATT | TTTAAATTAT |     |     |     |     |     |     | 4125 |
| Lys | Lys | Gly | Tyr | Glu | Ile | Gly |     |     |     |     |     |     |     |     |     |     |
|     | 730 |     |     |     |     | 735 |     |     |     |     |     |     |     |     |     |     |
| CTAAAAACA | GTAAAATTAA | AACATACTCT | TTTTGTAAGA | AATACAAGGA | GAGTATGTTT |     |     |     |     |     |     |     |     |     |     | 4185 |
| TAAACAGTAA | TCTAAATCAT | CATAATCCTT | TGAGATTGTT | TGTAGGATCC |     |     |     |     |     |     |     |     |     |     |     | 4235 |

( 2 ) INFORMATION FOR SEQ ID NO:4:

( i ) SEQUENCE CHARACTERISTICS:
        ( A ) LENGTH: 735 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Glu | Val | Lys | Gln | Glu | Asn | Arg | Leu | Leu | Asn | Glu | Ser | Glu | Ser | Ser | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Gly | Leu | Leu | Gly | Tyr | Tyr | Phe | Ser | Asp | Leu | Asn | Phe | Gln | Ala | Pro |
|     |     |     | 20  |     |     |     |     | 25  |     |     |     |     | 30  |     |     |
| Met | Val | Val | Thr | Ser | Ser | Thr | Thr | Gly | Asp | Leu | Ser | Ile | Pro | Ser | Ser |
|     |     |     | 35  |     |     |     |     | 40  |     |     |     |     | 45  |     |     |
| Glu | Leu | Glu | Asn | Ile | Pro | Ser | Glu | Asn | Gln | Tyr | Phe | Gln | Ser | Ala | Ile |

|      |      |      |      |      |      |      |      |      |      |      |      |      |      |      |      |
|---|---|---|---|---|---|---|---|---|---|---|---|---|---|---|---|
| | 50 | | | | | 55 | | | | | 60 | | | | |
| Trp | Ser | Gly | Phe | Ile | Lys | Val | Lys | Lys | Ser | Asp | Glu | Tyr | Thr | Phe | Ala |
| 65 | | | | | 70 | | | | | 75 | | | | | 80 |
| Thr | Ser | Ala | Asp | Asn | His | Val | Thr | Met | Trp | Val | Asp | Asp | Gln | Glu | Val |
| | | | | | 85 | | | | | 90 | | | | | 95 |
| Ile | Asn | Lys | Ala | Ser | Asn | Ser | Asn | Lys | Ile | Arg | Leu | Glu | Lys | Gly | Arg |
| | | | | 100 | | | | | 105 | | | | | 110 | |
| Leu | Tyr | Gln | Ile | Lys | Ile | Gln | Tyr | Gln | Arg | Glu | Asn | Pro | Thr | Glu | Lys |
| | | | | 115 | | | | | 120 | | | | | 125 | |
| Gly | Leu | Asp | Phe | Lys | Leu | Tyr | Trp | Thr | Asp | Ser | Gln | Asn | Lys | Lys | Glu |
| | | 130 | | | | | 135 | | | | | 140 | | | |
| Val | Ile | Ser | Ser | Asp | Asn | Leu | Gln | Leu | Pro | Glu | Leu | Lys | Gln | Lys | Ser |
| 145 | | | | | 150 | | | | | 155 | | | | | 160 |
| Ser | Asn | Ser | Arg | Lys | Lys | Arg | Ser | Thr | Ser | Ala | Gly | Pro | Thr | Val | Pro |
| | | | | 165 | | | | | 170 | | | | | 175 | |
| Asp | Arg | Asp | Asn | Asp | Gly | Ile | Pro | Asp | Ser | Leu | Glu | Val | Glu | Gly | Tyr |
| | | | | 180 | | | | | 185 | | | | | 190 | |
| Thr | Val | Asp | Val | Lys | Asn | Lys | Arg | Thr | Phe | Leu | Ser | Pro | Trp | Ile | Ser |
| | | | 195 | | | | | 200 | | | | | 205 | | |
| Asn | Ile | His | Glu | Lys | Lys | Gly | Leu | Thr | Lys | Tyr | Lys | Ser | Ser | Pro | Glu |
| | | | 210 | | | | | 215 | | | | | 220 | | |
| Lys | Trp | Ser | Thr | Ala | Ser | Asp | Pro | Tyr | Ser | Asp | Phe | Glu | Lys | Val | Thr |
| 225 | | | | | 230 | | | | | 235 | | | | | 240 |
| Gly | Arg | Ile | Asp | Lys | Asn | Val | Ser | Pro | Glu | Ala | Arg | His | Pro | Leu | Val |
| | | | | 245 | | | | | 250 | | | | | 255 | |
| Ala | Ala | Tyr | Pro | Ile | Val | His | Val | Asp | Met | Glu | Asn | Ile | Ile | Leu | Ser |
| | | | 260 | | | | | 265 | | | | | 270 | | |
| Lys | Asn | Glu | Asp | Gln | Ser | Thr | Gln | Asn | Thr | Asp | Ser | Glu | Thr | Arg | Thr |
| | | | 275 | | | | | 280 | | | | | 285 | | |
| Ile | Ser | Lys | Asn | Thr | Ser | Thr | Ser | Arg | Thr | His | Thr | Ser | Glu | Val | His |
| | | | 290 | | | | | 295 | | | | | 300 | | |
| Gly | Asn | Ala | Glu | Val | His | Ala | Ser | Phe | Phe | Asp | Ile | Gly | Gly | Ser | Val |
| 305 | | | | | 310 | | | | | 315 | | | | | 320 | |
| Ser | Ala | Gly | Phe | Ser | Asn | Ser | Asn | Ser | Ser | Thr | Val | Ala | Ile | Asp | His |
| | | | | 325 | | | | | 330 | | | | | 335 | |
| Ser | Leu | Ser | Leu | Ala | Gly | Glu | Arg | Thr | Trp | Ala | Glu | Thr | Met | Gly | Leu |
| | | | 340 | | | | | 345 | | | | | 350 | | |
| Asn | Thr | Ala | Asp | Thr | Ala | Arg | Leu | Asn | Ala | Asn | Ile | Arg | Tyr | Val | Asn |
| | | | 355 | | | | | 360 | | | | | 365 | | |
| Thr | Gly | Thr | Ala | Pro | Ile | Tyr | Asn | Val | Leu | Pro | Thr | Thr | Ser | Leu | Val |
| | | 370 | | | | | 375 | | | | | 380 | | | |
| Leu | Gly | Lys | Asn | Gln | Thr | Leu | Ala | Thr | Ile | Lys | Ala | Lys | Glu | Asn | Gln |
| 385 | | | | | 390 | | | | | 395 | | | | | 400 |
| Leu | Ser | Gln | Ile | Leu | Ala | Pro | Asn | Asn | Tyr | Tyr | Pro | Ser | Lys | Asn | Leu |
| | | | | 405 | | | | | 410 | | | | | 415 | |
| Ala | Pro | Ile | Ala | Leu | Asn | Ala | Gln | Asp | Asp | Phe | Ser | Ser | Thr | Pro | Ile |
| | | | 420 | | | | | 425 | | | | | 430 | | |
| Thr | Met | Asn | Tyr | Asn | Gln | Phe | Leu | Glu | Leu | Glu | Lys | Thr | Lys | Gln | Leu |
| | | 435 | | | | | 440 | | | | | 445 | | | |
| Arg | Leu | Asp | Thr | Asp | Gln | Val | Tyr | Gly | Asn | Ile | Ala | Thr | Tyr | Asn | Phe |
| | | 450 | | | | | 455 | | | | | 460 | | | |
| Glu | Asn | Gly | Arg | Val | Arg | Val | Asp | Thr | Gly | Ser | Asn | Trp | Ser | Glu | Val |
| 465 | | | | | 470 | | | | | 475 | | | | | 480 | |

| | | | | | | | | | | | | | | |
|---|---|---|---|---|---|---|---|---|---|---|---|---|---|---|
| Leu | Pro | Gln | Ile | Gln | Glu | Thr | Thr | Ala | Arg | Ile | Ile | Phe | Asn | Gly | Lys |
| | | | | 485 | | | | | 490 | | | | | 495 | |
| Asp | Leu | Asn | Leu | Val | Glu | Arg | Arg | Ile | Ala | Ala | Val | Asn | Pro | Ser | Asp |
| | | | 500 | | | | 505 | | | | | 510 | | | |
| Pro | Leu | Glu | Thr | Thr | Lys | Pro | Asp | Met | Thr | Leu | Lys | Glu | Ala | Leu | Lys |
| | | | 515 | | | | 520 | | | | | 525 | | | |
| Ile | Ala | Phe | Gly | Phe | Asn | Glu | Pro | Asn | Gly | Asn | Leu | Gln | Tyr | Gln | Gly |
| | 530 | | | | | 535 | | | | | 540 | | | | |
| Lys | Asp | Ile | Thr | Glu | Phe | Asp | Phe | Asn | Phe | Asp | Gln | Gln | Thr | Ser | Gln |
| 545 | | | | | 550 | | | | | 555 | | | | | 560 |
| Asn | Ile | Lys | Asn | Gln | Leu | Ala | Glu | Leu | Asn | Ala | Thr | Asn | Ile | Tyr | Thr |
| | | | | 565 | | | | | 570 | | | | | 575 | |
| Val | Leu | Asp | Lys | Ile | Lys | Leu | Asn | Ala | Lys | Met | Asn | Ile | Leu | Ile | Arg |
| | | | 580 | | | | | 585 | | | | | 590 | | |
| Asp | Lys | Arg | Phe | His | Tyr | Asp | Arg | Asn | Asn | Ile | Ala | Val | Gly | Ala | Asp |
| | | 595 | | | | | 600 | | | | | 605 | | | |
| Glu | Ser | Val | Val | Lys | Glu | Ala | His | Arg | Glu | Val | Ile | Asn | Ser | Ser | Thr |
| | 610 | | | | | 615 | | | | | 620 | | | | |
| Glu | Gly | Leu | Leu | Leu | Asn | Ile | Asp | Lys | Asp | Ile | Arg | Lys | Ile | Leu | Ser |
| 625 | | | | | 630 | | | | | 635 | | | | | 640 |
| Gly | Tyr | Ile | Val | Glu | Ile | Glu | Asp | Thr | Glu | Gly | Leu | Lys | Glu | Val | Ile |
| | | | | 645 | | | | | 650 | | | | | 655 | |
| Asn | Asp | Arg | Tyr | Asp | Met | Leu | Asn | Ile | Ser | Ser | Leu | Arg | Gln | Asp | Gly |
| | | | 660 | | | | | 665 | | | | | 670 | | |
| Lys | Thr | Phe | Ile | Asp | Phe | Lys | Lys | Tyr | Asn | Asp | Lys | Leu | Pro | Leu | Tyr |
| | | 675 | | | | | 680 | | | | | 685 | | | |
| Ile | Ser | Asn | Pro | Asn | Tyr | Lys | Val | Asn | Val | Tyr | Ala | Val | Thr | Lys | Glu |
| | 690 | | | | | 695 | | | | | 700 | | | | |
| Asn | Thr | Ile | Ile | Asn | Pro | Ser | Glu | Asn | Gly | Asp | Thr | Ser | Thr | Asn | Gly |
| 705 | | | | | 710 | | | | | 715 | | | | | 720 |
| Ile | Lys | Lys | Ile | Leu | Ile | Phe | Ser | Lys | Lys | Gly | Tyr | Glu | Ile | Gly | |
| | | | | 725 | | | | | 730 | | | | | 735 | |

( 2 ) INFORMATION FOR SEQ ID NO:5:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1368

( x i ) SEQUENCE DESCRIPTION: SEQ ID NO:5:

| | | | | | | | | | | | | | | | |
|---|---|---|---|---|---|---|---|---|---|---|---|---|---|---|---|
| GCG | GGC | GGT | CAT | GGT | GAT | GTA | GGT | ATG | CAC | GTA | AAA | GAG | AAA | GAG | AAA | 48 |
| Ala | Gly | Gly | His | Gly | Asp | Val | Gly | Met | His | Val | Lys | Glu | Lys | Glu | Lys |
| 1 | | | | 5 | | | | | 10 | | | | | 15 | |
| AAT | AAA | GAT | GAG | AAT | AAG | AGA | AAA | GAT | GAA | GAA | CGA | AAT | AAA | ACA | CAG | 96 |
| Asn | Lys | Asp | Glu | Asn | Lys | Arg | Lys | Asp | Glu | Glu | Arg | Asn | Lys | Thr | Gln |
| | | | 20 | | | | | 25 | | | | | 30 | | |
| GAA | GAG | CAT | TTA | AAG | GAA | ATC | ATG | AAA | CAC | ATT | GTA | AAA | ATA | GAA | GTA | 144 |
| Glu | Glu | His | Leu | Lys | Glu | Ile | Met | Lys | His | Ile | Val | Lys | Ile | Glu | Val |
| | | 35 | | | | | 40 | | | | | 45 | | | |
| AAA | GGG | GAG | GAA | GCT | GTT | AAA | AAA | GAG | GCA | GCA | GAA | AAG | CTA | CTT | GAG | 192 |
| Lys | Gly | Glu | Glu | Ala | Val | Lys | Lys | Glu | Ala | Ala | Glu | Lys | Leu | Leu | Glu |
| | 50 | | | | | 55 | | | | | 60 | | | | |

| | | | | | | | | | | | | | | | | |
|---|---|---|---|---|---|---|---|---|---|---|---|---|---|---|---|---|
| AAA | GTA | CCA | TCT | GAT | GTT | TTA | GAG | ATG | TAT | AAA | GCA | ATT | GGA | GGA | AAG | 240 |
| Lys 65 | Val | Pro | Ser | Asp | Val 70 | Leu | Glu | Met | Tyr | Lys 75 | Ala | Ile | Gly | Gly | Lys 80 | |
| ATA | TAT | ATT | GTG | GAT | GGT | GAT | ATT | ACA | AAA | CAT | ATA | TCT | TTA | GAA | GCA | 288 |
| Ile | Tyr | Ile | Val | Asp 85 | Gly | Asp | Ile | Thr | Lys 90 | His | Ile | Ser | Leu | Glu 95 | Ala | |
| TTA | TCT | GAA | GAT | AAG | AAA | AAA | ATA | AAA | GAC | ATT | TAT | GGG | AAA | GAT | GCT | 336 |
| Leu | Ser | Glu | Asp 100 | Lys | Lys | Lys | Ile | Lys 105 | Asp | Ile | Tyr | Gly | Lys 110 | Asp | Ala | |
| TTA | TTA | CAT | GAA | CAT | TAT | GTA | TAT | GCA | AAA | GAA | GGA | TAT | GAA | CCC | GTA | 384 |
| Leu | Leu | His 115 | Glu | His | Tyr | Val | Tyr 120 | Ala | Lys | Glu | Gly | Tyr 125 | Glu | Pro | Val | |
| CTT | GTA | ATC | CAA | TCT | TCG | GAA | GAT | TAT | GTA | GAA | AAT | ACT | GAA | AAG | GCA | 432 |
| Leu | Val 130 | Ile | Gln | Ser | Ser 135 | Glu | Asp | Tyr | Val | Glu 140 | Asn | Thr | Glu | Lys | Ala | |
| CTG | AAC | GTT | TAT | TAT | GAA | ATA | GGT | AAG | ATA | TTA | TCA | AGG | GAT | ATT | TTA | 480 |
| Leu 145 | Asn | Val | Tyr | Tyr | Glu 150 | Ile | Gly | Lys | Ile | Leu 155 | Ser | Arg | Asp | Ile | Leu 160 | |
| AGT | AAA | ATT | AAT | CAA | CCA | TAT | CAG | AAA | TTT | TTA | GAT | GTA | TTA | AAT | ACC | 528 |
| Ser | Lys | Ile | Asn | Gln 165 | Pro | Tyr | Gln | Lys | Phe 170 | Leu | Asp | Val | Leu | Asn 175 | Thr | |
| ATT | AAA | AAT | GCA | TCT | GAT | TCA | GAT | GGA | CAA | GAT | CTT | TTA | TTT | ACT | AAT | 576 |
| Ile | Lys | Asn | Ala 180 | Ser | Asp | Ser | Asp | Gly 185 | Gln | Asp | Leu | Leu | Phe 190 | Thr | Asn | |
| CAG | CTT | AAG | GAA | CAT | CCC | ACA | GAC | TTT | TCT | GTA | GAA | TTC | TTG | GAA | CAA | 624 |
| Gln | Leu | Lys 195 | Glu | His | Pro | Thr | Asp 200 | Phe | Ser | Val | Glu | Phe 205 | Leu | Glu | Gln | |
| AAT | AGC | AAT | GAG | GTA | CAA | GAA | GTA | TTT | GCG | AAA | GCT | TTT | GCA | TAT | TAT | 672 |
| Asn | Ser | Asn | Glu 210 | Val | Gln | Glu | Val 215 | Phe | Ala | Lys | Ala | Phe 220 | Ala | Tyr | Tyr | |
| ATC | GAG | CCA | CAG | CAT | CGT | GAT | GTT | TTA | CAG | CTT | TAT | GCA | CCG | GAA | GCT | 720 |
| Ile 225 | Glu | Pro | Gln | His | Arg 230 | Asp | Val | Leu | Gln | Leu 235 | Tyr | Ala | Pro | Glu | Ala 240 | |
| TTT | AAT | TAC | ATG | GAT | AAA | TTT | AAC | GAA | CAA | GAA | ATA | AAT | CTA | CTC | GGC | 768 |
| Phe | Asn | Tyr | Met | Asp 245 | Lys | Phe | Asn | Glu | Gln 250 | Glu | Ile | Asn | Leu | Leu 255 | Gly | |
| GAC | GGC | GGC | GAC | GTC | AGC | TTC | AGC | ACC | CGC | GGC | ACG | CAG | AAC | TGG | ACG | 816 |
| Asp | Gly | Gly | Asp 260 | Val | Ser | Phe | Ser | Thr 265 | Arg | Gly | Thr | Gln | Asn 270 | Trp | Thr | |
| GTG | GAG | CGG | CTG | CTC | CAG | GCG | CAC | CGC | CAA | CTG | GAG | GAG | CGC | GGC | TAT | 864 |
| Val | Glu | Arg 275 | Leu | Leu | Gln | Ala | His 280 | Arg | Gln | Leu | Glu | Glu 285 | Arg | Gly | Tyr | |
| GTG | TTC | GTC | GGC | TAC | CAC | GGC | ACC | TTC | CTC | GAA | GCG | GCG | CAA | AGC | ATC | 912 |
| Val | Phe 290 | Val | Gly | Tyr | His | Gly 295 | Thr | Phe | Leu | Glu | Ala 300 | Ala | Gln | Ser | Ile | |
| GTC | TTC | GGC | GGG | GTG | CGC | GCG | CGC | AGC | CAG | GAC | CTC | GAC | GCG | ATC | TGG | 960 |
| Val 305 | Phe | Gly | Gly | Val | Arg 310 | Ala | Arg | Ser | Gln | Asp 315 | Leu | Asp | Ala | Ile | Trp 320 | |
| CGC | GGT | TTC | TAT | ATC | GCC | GGC | GAT | CCG | GCG | CTG | GCC | TAC | GGC | TAC | GCC | 1008 |
| Arg | Gly | Phe | Tyr | Ile 325 | Ala | Gly | Asp | Pro | Ala 330 | Leu | Ala | Tyr | Gly | Tyr 335 | Ala | |
| CAG | GAC | CAG | GAA | CCC | GAC | GCA | CGC | GGC | CGG | ATC | CGC | AAC | GGT | GCC | CTG | 1056 |
| Gln | Asp | Gln | Glu 340 | Pro | Asp | Ala | Arg | Gly 345 | Arg | Ile | Arg | Asn | Gly 350 | Ala | Leu | |
| CTG | CGG | GTC | TAT | GTG | CCG | CGC | TCG | AGC | CTG | CCG | GGC | TTC | TAC | CGC | ACC | 1104 |
| Leu | Arg | Val 355 | Tyr | Val | Pro | Arg | Ser 360 | Ser | Leu | Pro | Gly | Phe 365 | Tyr | Arg | Thr | |
| AGC | CTG | ACC | CTG | GCC | GCG | CCG | GAG | GCG | GCG | GGC | GAG | GTC | GAA | CGG | CTG | 1152 |
| Ser | Leu | Thr 370 | Leu | Ala | Ala | Pro | Glu 375 | Ala | Ala | Gly | Glu | Val 380 | Glu | Arg | Leu | |

```
ATC  GGC  CAT  CCG  CTG  CCG  CTG  CGC  CTG  GAC  GCC  ATC  ACC  GGC  CCC  GAG    1200
Ile  Gly  His  Pro  Leu  Pro  Leu  Arg  Leu  Asp  Ala  Ile  Thr  Gly  Pro  Glu
385            390                      395                      400

GAG  GAA  GGC  GGG  CGC  CTG  GAG  ACC  ATT  CTC  GGC  TGG  CCG  CTG  GCC  GAG    1248
Glu  Glu  Gly  Gly  Arg  Leu  Glu  Thr  Ile  Leu  Gly  Trp  Pro  Leu  Ala  Glu
                    405                      410                      415

CGC  ACC  GTG  GTG  ATT  CCC  TCG  GCG  ATC  CCC  ACC  GAC  CCG  CGC  AAC  GTC    1296
Arg  Thr  Val  Val  Ile  Pro  Ser  Ala  Ile  Pro  Thr  Asp  Pro  Arg  Asn  Val
               420                      425                      430

GGC  GGC  GAC  CTC  GAC  CCG  TCC  AGC  ATC  CCC  GAC  AAG  GAA  CAG  GCG  ATC    1344
Gly  Gly  Asp  Leu  Asp  Pro  Ser  Ser  Ile  Pro  Asp  Lys  Glu  Gln  Ala  Ile
          435                      440                      445

AGC  GCC  CTG  CCG  GAC  TAC  GCC  AGC                                            1368
Ser  Ala  Leu  Pro  Asp  Tyr  Ala  Ser
450                      455
```

( 2 ) INFORMATION FOR SEQ ID NO:6:

( i ) SEQUENCE CHARACTERISTICS:
        ( A ) LENGTH: 456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Ala  Gly  Gly  His  Gly  Asp  Val  Gly  Met  His  Val  Lys  Glu  Lys  Glu  Lys
1               5                        10                       15

Asn  Lys  Asp  Glu  Asn  Lys  Arg  Lys  Asp  Glu  Glu  Arg  Asn  Lys  Thr  Gln
               20                       25                       30

Glu  Glu  His  Leu  Lys  Glu  Ile  Met  Lys  His  Ile  Val  Lys  Ile  Glu  Val
               35                       40                       45

Lys  Gly  Glu  Glu  Ala  Val  Lys  Glu  Ala  Ala  Glu  Lys  Leu  Leu  Glu
          50                       55                       60

Lys  Val  Pro  Ser  Asp  Val  Leu  Glu  Met  Tyr  Lys  Ala  Ile  Gly  Gly  Lys
65                       70                       75                       80

Ile  Tyr  Ile  Val  Asp  Gly  Asp  Ile  Thr  Lys  His  Ile  Ser  Leu  Glu  Ala
                    85                       90                       95

Leu  Ser  Glu  Asp  Lys  Lys  Lys  Ile  Lys  Asp  Ile  Tyr  Gly  Lys  Asp  Ala
               100                      105                      110

Leu  Leu  His  Glu  His  Tyr  Val  Tyr  Ala  Lys  Glu  Gly  Tyr  Glu  Pro  Val
          115                      120                      125

Leu  Val  Ile  Gln  Ser  Ser  Glu  Asp  Tyr  Val  Glu  Asn  Thr  Glu  Lys  Ala
     130                      135                      140

Leu  Asn  Val  Tyr  Tyr  Glu  Ile  Gly  Lys  Ile  Leu  Ser  Arg  Asp  Ile  Leu
145                      150                      155                      160

Ser  Lys  Ile  Asn  Gln  Pro  Tyr  Gln  Lys  Phe  Leu  Asp  Val  Leu  Asn  Thr
                    165                      170                      175

Ile  Lys  Asn  Ala  Ser  Asp  Ser  Asp  Gly  Gln  Asp  Leu  Leu  Phe  Thr  Asn
               180                      185                      190

Gln  Leu  Lys  Glu  His  Pro  Thr  Asp  Phe  Ser  Val  Glu  Phe  Leu  Glu  Gln
          195                      200                      205

Asn  Ser  Asn  Glu  Val  Gln  Glu  Val  Phe  Ala  Lys  Ala  Phe  Ala  Tyr  Tyr
     210                      215                      220

Ile  Glu  Pro  Gln  His  Arg  Asp  Val  Leu  Gln  Leu  Tyr  Ala  Pro  Glu  Ala
225                      230                      235                      240

Phe  Asn  Tyr  Met  Asp  Lys  Phe  Asn  Glu  Gln  Glu  Ile  Asn  Leu  Leu  Gly
                    245                      250                      255
```

| | | | | | | | | | | | | | | |
|---|---|---|---|---|---|---|---|---|---|---|---|---|---|---|
| Asp | Gly | Gly | Asp 260 | Val | Ser | Phe | Ser | Thr 265 | Arg | Gly | Thr | Gln | Asn 270 | Trp | Thr |
| Val | Glu | Arg 275 | Leu | Leu | Gln | Ala | His 280 | Arg | Gln | Leu | Glu | Glu 285 | Arg | Gly | Tyr |
| Val | Phe 290 | Val | Gly | Tyr | His | Gly 295 | Thr | Phe | Leu | Glu | Ala 300 | Ala | Gln | Ser | Ile |
| Val 305 | Phe | Gly | Gly | Val | Arg 310 | Ala | Arg | Ser | Gln | Asp 315 | Leu | Asp | Ala | Ile | Trp 320 |
| Arg | Gly | Phe | Tyr | Ile 325 | Ala | Gly | Asp | Pro | Ala 330 | Leu | Ala | Tyr | Gly 335 | Tyr | Ala |
| Gln | Asp | Gln | Glu 340 | Pro | Asp | Ala | Arg | Gly 345 | Arg | Ile | Arg | Asn 350 | Gly | Ala | Leu |
| Leu | Arg | Val 355 | Tyr | Val | Pro | Arg | Ser 360 | Ser | Leu | Pro | Gly 365 | Phe | Tyr | Arg | Thr |
| Ser | Leu 370 | Thr | Leu | Ala | Ala | Pro 375 | Glu | Ala | Gly | Glu 380 | Val | Glu | Arg | Leu | |
| Ile 385 | Gly | His | Pro | Leu | Pro 390 | Leu | Arg | Leu | Asp | Ala 395 | Ile | Thr | Gly | Pro | Glu 400 |
| Glu | Glu | Gly | Gly | Arg 405 | Leu | Glu | Thr | Ile | Leu 410 | Gly | Trp | Pro | Leu | Ala 415 | Glu |
| Arg | Thr | Val | Val 420 | Ile | Pro | Ser | Ala | Ile 425 | Pro | Thr | Asp | Pro | Arg 430 | Asn | Val |
| Gly | Gly | Asp 435 | Leu | Asp | Pro | Ser | Ser 440 | Ile | Pro | Asp | Lys | Glu 445 | Gln | Ala | Ile |
| Ser | Ala 450 | Leu | Pro | Asp | Tyr | Ala 455 | Ser | | | | | | | | |

( 2 ) INFORMATION FOR SEQ ID NO:7:

( i ) SEQUENCE CHARACTERISTICS:
        ( A ) LENGTH: 1425 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1416

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GTA | CCA | GCG | GGC | GGT | CAT | GGT | GAT | GTA | GGT | ATG | CAC | GTA | AAA | GAG | 48 |
| Met 1 | Val | Pro | Ala | Gly 5 | Gly | His | Gly | Asp | Val 10 | Gly | Met | His | Val | Lys 15 | Glu | |
| AAA | GAG | AAA | AAT | AAA | GAT | GAG | AAT | AAG | AGA | AAA | GAT | GAA | GAA | CGA | AAT | 96 |
| Lys | Glu | Lys | Asn 20 | Lys | Asp | Glu | Asn | Lys 25 | Arg | Lys | Asp | Glu | Glu 30 | Arg | Asn | |
| AAA | ACA | CAG | GAA | GAG | CAT | TTA | AAG | GAA | ATC | ATG | AAA | CAC | ATT | GTA | AAA | 144 |
| Lys | Thr | Gln 35 | Glu | Glu | His | Leu | Lys 40 | Glu | Ile | Met | Lys | His 45 | Ile | Val | Lys | |
| ATA | GAA | GTA | AAA | GGG | GAG | GAA | GCT | GTT | AAA | AAA | GAG | GCA | GCA | GAA | AAG | 192 |
| Ile | Glu 50 | Val | Lys | Gly | Glu | Glu 55 | Ala | Val | Lys | Lys | Glu 60 | Ala | Ala | Glu | Lys | |
| CTA | CTT | GAG | AAA | GTA | CCA | TCT | GAT | GTT | TTA | GAG | ATG | TAT | AAA | GCA | ATT | 240 |
| Leu | Leu 65 | Glu | Lys | Val | Pro | Ser 70 | Asp | Val | Leu | Glu | Met 75 | Tyr | Lys | Ala | Ile 80 | |
| GGA | GGA | AAG | ATA | TAT | ATT | GTG | GAT | GGT | GAT | ATT | ACA | AAA | CAT | ATA | TCT | 288 |
| Gly | Gly | Lys | Ile | Tyr 85 | Ile | Val | Asp | Gly | Asp 90 | Ile | Thr | Lys | His | Ile 95 | Ser | |

| | | | | | | | | | | | | | | | | |
|---|---|---|---|---|---|---|---|---|---|---|---|---|---|---|---|---|
| TTA | GAA | GCA | TTA | TCT | GAA | GAT | AAG | AAA | AAA | ATA | AAA | GAC | ATT | TAT | GGG | 336 |
| Leu | Glu | Ala | Leu | Ser | Glu | Asp | Lys | Lys | Lys | Ile | Lys | Asp | Ile | Tyr | Gly | |
| | | | | | | | | 100 | | | | 105 | | | | 110 | | | |

| AAA | GAT | GCT | TTA | TTA | CAT | GAA | CAT | TAT | GTA | TAT | GCA | AAA | GAA | GGA | TAT | 384 |
| Lys | Asp | Ala | Leu | Leu | His | Glu | His | Tyr | Val | Tyr | Ala | Lys | Glu | Gly | Tyr | |
| | | 115 | | | | | 120 | | | | | 125 | | | | |

| GAA | CCC | GTA | CTT | GTA | ATC | CAA | TCT | TCG | GAA | GAT | TAT | GTA | GAA | AAT | ACT | 432 |
| Glu | Pro | Val | Leu | Val | Ile | Gln | Ser | Ser | Glu | Asp | Tyr | Val | Glu | Asn | Thr | |
| | 130 | | | | | 135 | | | | | 140 | | | | | |

| GAA | AAG | GCA | CTG | AAC | GTT | TAT | TAT | GAA | ATA | GGT | AAG | ATA | TTA | TCA | AGG | 480 |
| Glu | Lys | Ala | Leu | Asn | Val | Tyr | Tyr | Glu | Ile | Gly | Lys | Ile | Leu | Ser | Arg | |
| 145 | | | | | 150 | | | | | 155 | | | | | 160 | |

| GAT | ATT | TTA | AGT | AAA | ATT | AAT | CAA | CCA | TAT | CAG | AAA | TTT | TTA | GAT | GTA | 528 |
| Asp | Ile | Leu | Ser | Lys | Ile | Asn | Gln | Pro | Tyr | Gln | Lys | Phe | Leu | Asp | Val | |
| | | | | 165 | | | | | 170 | | | | | 175 | | |

| TTA | AAT | ACC | ATT | AAA | AAT | GCA | TCT | GAT | TCA | GAT | GGA | CAA | GAT | CTT | TTA | 576 |
| Leu | Asn | Thr | Ile | Lys | Asn | Ala | Ser | Asp | Ser | Asp | Gly | Gln | Asp | Leu | Leu | |
| | | | 180 | | | | | 185 | | | | | 190 | | | |

| TTT | ACT | AAT | CAG | CTT | AAG | GAA | CAT | CCC | ACA | GAC | TTT | TCT | GTA | GAA | TTC | 624 |
| Phe | Thr | Asn | Gln | Leu | Lys | Glu | His | Pro | Thr | Asp | Phe | Ser | Val | Glu | Phe | |
| | | 195 | | | | | 200 | | | | | 205 | | | | |

| TTG | GAA | CAA | AAT | AGC | AAT | GAG | GTA | CAA | GAA | GTA | TTT | GCG | AAA | GCT | TTT | 672 |
| Leu | Glu | Gln | Asn | Ser | Asn | Glu | Val | Gln | Glu | Val | Phe | Ala | Lys | Ala | Phe | |
| 210 | | | | | 215 | | | | | 220 | | | | | | |

| GCA | TAT | TAT | ATC | GAG | CCA | CAG | CAT | CGT | GAT | GTT | TTA | CAG | CTT | TAT | GCA | 720 |
| Ala | Tyr | Tyr | Ile | Glu | Pro | Gln | His | Arg | Asp | Val | Leu | Gln | Leu | Tyr | Ala | |
| 225 | | | | | 230 | | | | | 235 | | | | | 240 | |

| CCG | GAA | GCT | TTT | AAT | TAC | ATG | GAT | AAA | TTT | AAC | GAA | CAA | GAA | ATA | AAT | 768 |
| Pro | Glu | Ala | Phe | Asn | Tyr | Met | Asp | Lys | Phe | Asn | Glu | Gln | Glu | Ile | Asn | |
| | | | | 245 | | | | | 250 | | | | | 255 | | |

| CTA | ACG | CGT | GCG | GAG | TTC | CTC | GGC | GAC | GGC | GGC | GAC | GTC | AGC | TTC | AGC | 816 |
| Leu | Thr | Arg | Ala | Glu | Phe | Leu | Gly | Asp | Gly | Gly | Asp | Val | Ser | Phe | Ser | |
| | | | 260 | | | | | 265 | | | | | 270 | | | |

| ACC | CGC | GGC | ACG | CAG | AAC | TGG | ACG | GTG | GAG | CGG | CTG | CTC | CAG | GCG | CAC | 864 |
| Thr | Arg | Gly | Thr | Gln | Asn | Trp | Thr | Val | Glu | Arg | Leu | Leu | Gln | Ala | His | |
| | | 275 | | | | | 280 | | | | | 285 | | | | |

| CGC | CAA | CTG | GAG | GAG | CGC | GGC | TAT | GTG | TTC | GTC | GGC | TAC | CAC | GGC | ACC | 912 |
| Arg | Gln | Leu | Glu | Glu | Arg | Gly | Tyr | Val | Phe | Val | Gly | Tyr | His | Gly | Thr | |
| | 290 | | | | | 295 | | | | | 300 | | | | | |

| TTC | CTC | GAA | GCG | GCG | CAA | AGC | ATC | GTC | TTC | GGC | GGG | GTG | CGC | GCG | CGC | 960 |
| Phe | Leu | Glu | Ala | Ala | Gln | Ser | Ile | Val | Phe | Gly | Gly | Val | Arg | Ala | Arg | |
| 305 | | | | | 310 | | | | | 315 | | | | | 320 | |

| AGC | CAG | GAC | CTC | GAC | GCG | ATC | TGG | CGC | GGT | TTC | TAT | ATC | GCC | GGC | GAT | 1008 |
| Ser | Gln | Asp | Leu | Asp | Ala | Ile | Trp | Arg | Gly | Phe | Tyr | Ile | Ala | Gly | Asp | |
| | | | | 325 | | | | | 330 | | | | | 335 | | |

| CCG | GCG | CTG | GCC | TAC | GGC | TAC | GCC | CAG | GAC | CAG | GAA | CCC | GAC | GCA | CGC | 1056 |
| Pro | Ala | Leu | Ala | Tyr | Gly | Tyr | Ala | Gln | Asp | Gln | Glu | Pro | Asp | Ala | Arg | |
| | | | 340 | | | | | 345 | | | | | 350 | | | |

| GGC | CGG | ATC | CGC | AAC | GGT | GCC | CTG | CTG | CGG | GTC | TAT | GTG | CCG | CGC | TCG | 1104 |
| Gly | Arg | Ile | Arg | Asn | Gly | Ala | Leu | Leu | Arg | Val | Tyr | Val | Pro | Arg | Ser | |
| | | 355 | | | | | 360 | | | | | 365 | | | | |

| AGC | CTG | CCG | GGC | TTC | TAC | CGC | ACC | AGC | CTG | ACC | CTG | GCC | GCG | CCG | GAG | 1152 |
| Ser | Leu | Pro | Gly | Phe | Tyr | Arg | Thr | Ser | Leu | Thr | Leu | Ala | Ala | Pro | Glu | |
| | 370 | | | | | 375 | | | | | 380 | | | | | |

| GCG | GCG | GGC | GAG | GTC | GAA | CGG | CTG | ATC | GGC | CAT | CCG | CTG | CCG | CTG | CGC | 1200 |
| Ala | Ala | Gly | Glu | Val | Glu | Arg | Leu | Ile | Gly | His | Pro | Leu | Pro | Leu | Arg | |
| 385 | | | | | 390 | | | | | 395 | | | | | 400 | |

| CTG | GAC | GCC | ATC | ACC | GGC | CCC | GAG | GAG | GAA | GGC | GGG | CGC | CTG | GAG | ACC | 1248 |
| Leu | Asp | Ala | Ile | Thr | Gly | Pro | Glu | Glu | Glu | Gly | Gly | Arg | Leu | Glu | Thr | |
| | | | | 405 | | | | | 410 | | | | | 415 | | |

| | | | | | | | | | | | | | | | |
|---|---|---|---|---|---|---|---|---|---|---|---|---|---|---|---|
| ATT | CTC | GGC | TGG | CCG | CTG | GCC | GAG | CGC | ACC | GTG | GTG | ATT | CCC | TCG | GCG | 1296 |
| Ile | Leu | Gly | Trp | Pro | Leu | Ala | Glu | Arg | Thr | Val | Val | Ile | Pro | Ser | Ala | |
| | | | 420 | | | | 425 | | | | | 430 | | | | |
| ATC | CCC | ACC | GAC | CCG | CGC | AAC | GTC | GGC | GGC | GAC | CTC | GAC | CCG | TCC | AGC | 1344 |
| Ile | Pro | Thr | Asp | Pro | Arg | Asn | Val | Gly | Gly | Asp | Leu | Asp | Pro | Ser | Ser | |
| | | 435 | | | | | 440 | | | | | 445 | | | | |
| ATC | CCC | GAC | AAG | GAA | CAG | GCG | ATC | AGC | GCC | CTG | CCG | GAC | TAC | GCC | AGC | 1392 |
| Ile | Pro | Asp | Lys | Glu | Gln | Ala | Ile | Ser | Ala | Leu | Pro | Asp | Tyr | Ala | Ser | |
| | | 450 | | | | | 455 | | | | | 460 | | | | |
| CAG | CCC | GGC | AAA | CCG | CCG | CGC | GAG | GACCTGAAG | | | | | | | | 1425 |
| Gln | Pro | Gly | Lys | Pro | Pro | Arg | Glu | | | | | | | | | |
| 465 | | | | | 470 | | | | | | | | | | | |

( 2 ) INFORMATION FOR SEQ ID NO:8:

( i ) SEQUENCE CHARACTERISTICS:
    ( A ) LENGTH: 472 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

| Met | Val | Pro | Ala | Gly | Gly | His | Gly | Asp | Val | Gly | Met | His | Val | Lys | Glu |
|---|---|---|---|---|---|---|---|---|---|---|---|---|---|---|---|
| 1 | | | | 5 | | | | | 10 | | | | | 15 | |
| Lys | Glu | Lys | Asn | Lys | Asp | Glu | Asn | Lys | Arg | Lys | Asp | Glu | Glu | Arg | Asn |
| | | | 20 | | | | | 25 | | | | | 30 | | |
| Lys | Thr | Gln | Glu | Glu | His | Leu | Lys | Glu | Ile | Met | Lys | His | Ile | Val | Lys |
| | | 35 | | | | | 40 | | | | | 45 | | | |
| Ile | Glu | Val | Lys | Gly | Glu | Glu | Ala | Val | Lys | Lys | Glu | Ala | Ala | Glu | Lys |
| | 50 | | | | | 55 | | | | | 60 | | | | |
| Leu | Leu | Glu | Lys | Val | Pro | Ser | Asp | Val | Leu | Glu | Met | Tyr | Lys | Ala | Ile |
| 65 | | | | | 70 | | | | | 75 | | | | | 80 |
| Gly | Gly | Lys | Ile | Tyr | Ile | Val | Asp | Gly | Asp | Ile | Thr | Lys | His | Ile | Ser |
| | | | | 85 | | | | | 90 | | | | | 95 | |
| Leu | Glu | Ala | Leu | Ser | Glu | Asp | Lys | Lys | Lys | Ile | Lys | Asp | Ile | Tyr | Gly |
| | | | | 100 | | | | | 105 | | | | | 110 | |
| Lys | Asp | Ala | Leu | Leu | His | Glu | His | Tyr | Val | Tyr | Ala | Lys | Glu | Gly | Tyr |
| | | | 115 | | | | | 120 | | | | | 125 | | |
| Glu | Pro | Val | Leu | Val | Ile | Gln | Ser | Ser | Glu | Asp | Tyr | Val | Glu | Asn | Thr |
| | | 130 | | | | | 135 | | | | | 140 | | | |
| Glu | Lys | Ala | Leu | Asn | Val | Tyr | Tyr | Glu | Ile | Gly | Lys | Ile | Leu | Ser | Arg |
| 145 | | | | | 150 | | | | | 155 | | | | | 160 |
| Asp | Ile | Leu | Ser | Lys | Ile | Asn | Gln | Pro | Tyr | Gln | Lys | Phe | Leu | Asp | Val |
| | | | | 165 | | | | | 170 | | | | | 175 | |
| Leu | Asn | Thr | Ile | Lys | Asn | Ala | Ser | Asp | Ser | Gly | Gln | Asp | Leu | Leu | |
| | | | 180 | | | | | 185 | | | | | 190 | | |
| Phe | Thr | Asn | Gln | Leu | Lys | Glu | His | Pro | Thr | Asp | Phe | Ser | Val | Glu | Phe |
| | | | 195 | | | | | 200 | | | | | 205 | | |
| Leu | Glu | Gln | Asn | Ser | Asn | Glu | Val | Gln | Glu | Val | Phe | Ala | Lys | Ala | Phe |
| | | 210 | | | | | 215 | | | | | 220 | | | |
| Ala | Tyr | Tyr | Ile | Glu | Pro | Gln | His | Arg | Asp | Val | Leu | Gln | Leu | Tyr | Ala |
| 225 | | | | | 230 | | | | | 235 | | | | | 240 |
| Pro | Glu | Ala | Phe | Asn | Tyr | Met | Asp | Lys | Phe | Asn | Glu | Gln | Glu | Ile | Asn |
| | | | | 245 | | | | | 250 | | | | | 255 | |
| Leu | Thr | Arg | Ala | Glu | Phe | Leu | Gly | Asp | Gly | Gly | Asp | Val | Ser | Phe | Ser |
| | | | 260 | | | | | 265 | | | | | 270 | | |

```
Thr  Arg  Gly  Thr  Gln  Asn  Trp  Thr  Val  Glu  Arg  Leu  Leu  Gln  Ala  His
          275                      280                     285

Arg  Gln  Leu  Glu  Glu  Arg  Gly  Tyr  Val  Phe  Val  Gly  Tyr  His  Gly  Thr
     290                      295                     300

Phe  Leu  Glu  Ala  Ala  Gln  Ser  Ile  Val  Phe  Gly  Gly  Val  Arg  Ala  Arg
305                      310                     315                          320

Ser  Gln  Asp  Leu  Asp  Ala  Ile  Trp  Arg  Gly  Phe  Tyr  Ile  Ala  Gly  Asp
               325                      330                          335

Pro  Ala  Leu  Ala  Tyr  Gly  Tyr  Ala  Gln  Asp  Gln  Glu  Pro  Asp  Ala  Arg
               340                 345                     350

Gly  Arg  Ile  Arg  Asn  Gly  Ala  Leu  Leu  Arg  Val  Tyr  Val  Pro  Arg  Ser
          355                      360                     365

Ser  Leu  Pro  Gly  Phe  Tyr  Arg  Thr  Ser  Leu  Thr  Leu  Ala  Ala  Pro  Glu
     370                 375                     380

Ala  Ala  Gly  Glu  Val  Glu  Arg  Leu  Ile  Gly  His  Pro  Leu  Pro  Leu  Arg
385                 390                     395                              400

Leu  Asp  Ala  Ile  Thr  Gly  Pro  Glu  Glu  Glu  Gly  Gly  Arg  Leu  Glu  Thr
               405                 410                          415

Ile  Leu  Gly  Trp  Pro  Leu  Ala  Glu  Arg  Thr  Val  Val  Ile  Pro  Ser  Ala
               420                      425                     430

Ile  Pro  Thr  Asp  Pro  Arg  Asn  Val  Gly  Gly  Asp  Leu  Asp  Pro  Ser  Ser
          435                      440                     445

Ile  Pro  Asp  Lys  Glu  Gln  Ala  Ile  Ser  Ala  Leu  Pro  Asp  Tyr  Ala  Ser
     450                      455                     460

Gln  Pro  Gly  Lys  Pro  Pro  Arg  Glu
465                      470
```

( 2 ) INFORMATION FOR SEQ ID NO:9:

( i ) SEQUENCE CHARACTERISTICS:
        ( A ) LENGTH: 1524 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1524

( x i ) SEQUENCE DESCRIPTION: SEQ ID NO:9:

```
GCG  GGC  GGT  CAT  GGT  GAT  GTA  GGT  ATG  CAC  GTA  AAA  GAG  AAA  GAG  AAA     48
Ala  Gly  Gly  His  Gly  Asp  Val  Gly  Met  His  Val  Lys  Glu  Lys  Glu  Lys
  1                 5                      10                      15

AAT  AAA  GAT  GAG  AAT  AAG  AGA  AAA  GAT  GAA  GAA  CGA  AAT  AAA  ACA  CAG     96
Asn  Lys  Asp  Glu  Asn  Lys  Arg  Lys  Asp  Glu  Glu  Arg  Asn  Lys  Thr  Gln
               20                      25                      30

GAA  GAG  CAT  TTA  AAG  GAA  ATC  ATG  AAA  CAC  ATT  GTA  AAA  ATA  GAA  GTA    144
Glu  Glu  His  Leu  Lys  Glu  Ile  Met  Lys  His  Ile  Val  Lys  Ile  Glu  Val
          35                      40                      45

AAA  GGG  GAG  GAA  GCT  GTT  AAA  AAA  GAG  GCA  GCA  GAA  AAG  CTA  CTT  GAG    192
Lys  Gly  Glu  Glu  Ala  Val  Lys  Lys  Glu  Ala  Ala  Glu  Lys  Leu  Leu  Glu
     50                      55                      60

AAA  GTA  CCA  TCT  GAT  GTT  TTA  GAG  ATG  TAT  AAA  GCA  ATT  GGA  GGA  AAG    240
Lys  Val  Pro  Ser  Asp  Val  Leu  Glu  Met  Tyr  Lys  Ala  Ile  Gly  Gly  Lys
65                      70                      75                          80

ATA  TAT  ATT  GTG  GAT  GGT  GAT  ATT  ACA  AAA  CAT  ATA  TCT  TTA  GAA  GCA    288
Ile  Tyr  Ile  Val  Asp  Gly  Asp  Ile  Thr  Lys  His  Ile  Ser  Leu  Glu  Ala
               85                      90                      95
```

| | | | | | | | | | | | | | | | | |
|---|---|---|---|---|---|---|---|---|---|---|---|---|---|---|---|---|
| TTA | TCT | GAA | GAT | AAG | AAA | AAA | ATA | AAA | GAC | ATT | TAT | GGG | AAA | GAT | GCT | 336 |
| Leu | Ser | Glu | Asp | Lys | Lys | Lys | Ile | Lys | Asp | Ile | Tyr | Gly | Lys | Asp | Ala | |
| | | | | 100 | | | | 105 | | | | | 110 | | | |
| TTA | TTA | CAT | GAA | CAT | TAT | GTA | TAT | GCA | AAA | GAA | GGA | TAT | GAA | CCC | GTA | 384 |
| Leu | Leu | His | Glu | His | Tyr | Val | Tyr | Ala | Lys | Glu | Gly | Tyr | Glu | Pro | Val | |
| | | 115 | | | | 120 | | | | | 125 | | | | | |
| CTT | GTA | ATC | CAA | TCT | TCG | GAA | GAT | TAT | GTA | GAA | AAT | ACT | GAA | AAG | GCA | 432 |
| Leu | Val | Ile | Gln | Ser | Ser | Glu | Asp | Tyr | Val | Glu | Asn | Thr | Glu | Lys | Ala | |
| 130 | | | | | 135 | | | | | 140 | | | | | | |
| CTG | AAC | GTT | TAT | TAT | GAA | ATA | GGT | AAG | ATA | TTA | TCA | AGG | GAT | ATT | TTA | 480 |
| Leu | Asn | Val | Tyr | Tyr | Glu | Ile | Gly | Lys | Ile | Leu | Ser | Arg | Asp | Ile | Leu | |
| 145 | | | | | 150 | | | | | 155 | | | | | 160 | |
| AGT | AAA | ATT | AAT | CAA | CCA | TAT | CAG | AAA | TTT | TTA | GAT | GTA | TTA | AAT | ACC | 528 |
| Ser | Lys | Ile | Asn | Gln | Pro | Tyr | Gln | Lys | Phe | Leu | Asp | Val | Leu | Asn | Thr | |
| | | | | 165 | | | | 170 | | | | | 175 | | | |
| ATT | AAA | AAT | GCA | TCT | GAT | TCA | GAT | GGA | CAA | GAT | CTT | TTA | TTT | ACT | AAT | 576 |
| Ile | Lys | Asn | Ala | Ser | Asp | Ser | Asp | Gly | Gln | Asp | Leu | Leu | Phe | Thr | Asn | |
| | | | 180 | | | | | 185 | | | | | 190 | | | |
| CAG | CTT | AAG | GAA | CAT | CCC | ACA | GAC | TTT | TCT | GTA | GAA | TTC | TTG | GAA | CAA | 624 |
| Gln | Leu | Lys | Glu | His | Pro | Thr | Asp | Phe | Ser | Val | Glu | Phe | Leu | Glu | Gln | |
| | | 195 | | | | 200 | | | | | 205 | | | | | |
| AAT | AGC | AAT | GAG | GTA | CAA | GAA | GTA | TTT | GCG | AAA | GCT | TTT | GCA | TAT | TAT | 672 |
| Asn | Ser | Asn | Glu | Val | Gln | Glu | Val | Phe | Ala | Lys | Ala | Phe | Ala | Tyr | Tyr | |
| | | 210 | | | | | 215 | | | | | 220 | | | | |
| ATC | GAG | CCA | CAG | CAT | CGT | GAT | GTT | TTA | CAG | CTT | TAT | GCA | CCG | GAA | GCT | 720 |
| Ile | Glu | Pro | Gln | His | Arg | Asp | Val | Leu | Gln | Leu | Tyr | Ala | Pro | Glu | Ala | |
| 225 | | | | | 230 | | | | | 235 | | | | | 240 | |
| TTT | AAT | TAC | ATG | GAT | AAA | TTT | AAC | GAA | CAA | GAA | ATA | AAT | CTA | ACG | CGT | 768 |
| Phe | Asn | Tyr | Met | Asp | Lys | Phe | Asn | Glu | Gln | Glu | Ile | Asn | Leu | Thr | Arg | |
| | | | | 245 | | | | | 250 | | | | | 255 | | |
| GCG | GCC | AAC | GCC | GAC | GTG | GTG | AGC | CTG | ACC | TGC | CCG | GTC | GCC | GCC | GGT | 816 |
| Ala | Ala | Asn | Ala | Asp | Val | Val | Ser | Leu | Thr | Cys | Pro | Val | Ala | Ala | Gly | |
| | | | 260 | | | | | 265 | | | | | 270 | | | |
| GAA | TGC | GCG | GGC | CCG | GCG | GAC | AGC | GGC | GAC | GCC | CTG | CTG | GAG | CGC | AAC | 864 |
| Glu | Cys | Ala | Gly | Pro | Ala | Asp | Ser | Gly | Asp | Ala | Leu | Leu | Glu | Arg | Asn | |
| | | 275 | | | | | 280 | | | | | 285 | | | | |
| TAT | CCC | ACT | GGC | GCG | GAG | TTC | CTC | GGC | GAC | GGC | GGC | GAC | GTC | AGC | TTC | 912 |
| Tyr | Pro | Thr | Gly | Ala | Glu | Phe | Leu | Gly | Asp | Gly | Gly | Asp | Val | Ser | Phe | |
| | 290 | | | | | 295 | | | | | 300 | | | | | |
| AGC | ACC | CGC | GGC | ACG | CAG | AAC | TGG | ACG | GTG | GAG | CGG | CTG | CTC | CAG | GCG | 960 |
| Ser | Thr | Arg | Gly | Thr | Gln | Asn | Trp | Thr | Val | Glu | Arg | Leu | Leu | Gln | Ala | |
| 305 | | | | | 310 | | | | | 315 | | | | | 320 | |
| CAC | CGC | CAA | CTG | GAG | GAG | CGC | GGC | TAT | GTG | TTC | GTC | GGC | TAC | CAC | GGC | 1008 |
| His | Arg | Gln | Leu | Glu | Glu | Arg | Gly | Tyr | Val | Phe | Val | Gly | Tyr | His | Gly | |
| | | | | 325 | | | | | 330 | | | | | 335 | | |
| ACC | TTC | CTC | GAA | GCG | GCG | CAA | AGC | ATC | GTC | TTC | GGC | GGG | GTG | CGC | GCG | 1056 |
| Thr | Phe | Leu | Glu | Ala | Ala | Gln | Ser | Ile | Val | Phe | Gly | Gly | Val | Arg | Ala | |
| | | | 340 | | | | | 345 | | | | | 350 | | | |
| CGC | AGC | CAG | GAC | CTC | GAC | GCG | ATC | TGG | CGC | GGT | TTC | TAT | ATC | GCC | GGC | 1104 |
| Arg | Ser | Gln | Asp | Leu | Asp | Ala | Ile | Trp | Arg | Gly | Phe | Tyr | Ile | Ala | Gly | |
| | | 355 | | | | | 360 | | | | | 365 | | | | |
| GAT | CCG | GCG | CTG | GCC | TAC | GGC | TAC | GCC | CAG | GAC | CAG | GAA | CCC | GAC | GCA | 1152 |
| Asp | Pro | Ala | Leu | Ala | Tyr | Gly | Tyr | Ala | Gln | Asp | Gln | Glu | Pro | Asp | Ala | |
| | 370 | | | | | 375 | | | | | 380 | | | | | |
| CGC | GGC | CGG | ATC | CGC | AAC | GGT | GCC | CTG | CTG | CGG | GTC | TAT | GTG | CCG | CGC | 1200 |
| Arg | Gly | Arg | Ile | Arg | Asn | Gly | Ala | Leu | Leu | Arg | Val | Tyr | Val | Pro | Arg | |
| 385 | | | | | 390 | | | | | 395 | | | | | 400 | |
| TCG | AGC | CTG | CCG | GGC | TTC | TAC | CGC | ACC | AGC | CTG | ACC | CTG | GCC | GCG | CCG | 1248 |
| Ser | Ser | Leu | Pro | Gly | Phe | Tyr | Arg | Thr | Ser | Leu | Thr | Leu | Ala | Ala | Pro | |
| | | | | 405 | | | | | 410 | | | | | 415 | | |

| | | | | | | | | | | | | | | | | |
|---|---|---|---|---|---|---|---|---|---|---|---|---|---|---|---|---|
| GAG | GCG | GCG | GGC | GAG | GTC | GAA | CGG | CTG | ATC | GGC | CAT | CCG | CTG | CCG | CTG | 1296 |
| Glu | Ala | Ala | Gly | Glu | Val | Glu | Arg | Leu | Ile | Gly | His | Pro | Leu | Pro | Leu | |
| | | | 420 | | | | 425 | | | | | | 430 | | | |
| CGC | CTG | GAC | GCC | ATC | ACC | GGC | CCC | GAG | GAG | GAA | GGC | GGG | CGC | CTG | GAG | 1344 |
| Arg | Leu | Asp | Ala | Ile | Thr | Gly | Pro | Glu | Glu | Glu | Gly | Gly | Arg | Leu | Glu | |
| | | | 435 | | | | | 440 | | | | | 445 | | | |
| ACC | ATT | CTC | GGC | TGG | CCG | CTG | GCC | GAG | CGC | ACC | GTG | GTG | ATT | CCC | TCG | 1392 |
| Thr | Ile | Leu | Gly | Trp | Pro | Leu | Ala | Glu | Arg | Thr | Val | Val | Ile | Pro | Ser | |
| | | 450 | | | | | 455 | | | | | 460 | | | | |
| GCG | ATC | CCC | ACC | GAC | CCG | CGC | AAC | GTC | GGC | GGC | GAC | CTC | GAC | CCG | TCC | 1440 |
| Ala | Ile | Pro | Thr | Asp | Pro | Arg | Asn | Val | Gly | Gly | Asp | Leu | Asp | Pro | Ser | |
| 465 | | | | | 470 | | | | | 475 | | | | | 480 | |
| AGC | ATC | CCC | GAC | AAG | GAA | CAG | GCG | ATC | AGC | GCC | CTG | CCG | GAC | TAC | GCC | 1488 |
| Ser | Ile | Pro | Asp | Lys | Glu | Gln | Ala | Ile | Ser | Ala | Leu | Pro | Asp | Tyr | Ala | |
| | | | | 485 | | | | | 490 | | | | | 495 | | |
| AGC | CAG | CCC | GGC | AAA | CCG | CCG | CGC | GAG | GAC | CTG | AAG | | | | | 1524 |
| Ser | Gln | Pro | Gly | Lys | Pro | Pro | Arg | Glu | Asp | Leu | Lys | | | | | |
| | | | 500 | | | | | 505 | | | | | | | | |

( 2 ) INFORMATION FOR SEQ ID NO:10:

( i ) SEQUENCE CHARACTERISTICS:
        ( A ) LENGTH: 508 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Ala | Gly | Gly | His | Gly | Asp | Val | Gly | Met | His | Val | Lys | Glu | Lys | Glu | Lys |
| 1 | | | | 5 | | | | | 10 | | | | | 15 | |
| Asn | Lys | Asp | Glu | Asn | Lys | Arg | Lys | Asp | Glu | Glu | Arg | Asn | Lys | Thr | Gln |
| | | | 20 | | | | | 25 | | | | | 30 | | |
| Glu | Glu | His | Leu | Lys | Glu | Ile | Met | Lys | His | Ile | Val | Lys | Ile | Glu | Val |
| | | 35 | | | | | 40 | | | | | 45 | | | |
| Lys | Gly | Glu | Glu | Ala | Val | Lys | Lys | Glu | Ala | Ala | Glu | Lys | Leu | Leu | Glu |
| | 50 | | | | | 55 | | | | | 60 | | | | |
| Lys | Val | Pro | Ser | Asp | Val | Leu | Glu | Met | Tyr | Lys | Ala | Ile | Gly | Gly | Lys |
| 65 | | | | | 70 | | | | | 75 | | | | | 80 |
| Ile | Tyr | Ile | Val | Asp | Gly | Asp | Ile | Thr | Lys | His | Ile | Ser | Leu | Glu | Ala |
| | | | | 85 | | | | | 90 | | | | | 95 | |
| Leu | Ser | Glu | Asp | Lys | Lys | Lys | Ile | Lys | Asp | Ile | Tyr | Gly | Lys | Asp | Ala |
| | | | 100 | | | | | 105 | | | | | 110 | | |
| Leu | Leu | His | Glu | His | Tyr | Val | Tyr | Ala | Lys | Glu | Gly | Tyr | Glu | Pro | Val |
| | | 115 | | | | | 120 | | | | | 125 | | | |
| Leu | Val | Ile | Gln | Ser | Ser | Glu | Asp | Tyr | Val | Glu | Asn | Thr | Glu | Lys | Ala |
| | 130 | | | | | 135 | | | | | 140 | | | | |
| Leu | Asn | Val | Tyr | Tyr | Glu | Ile | Gly | Lys | Ile | Leu | Ser | Arg | Asp | Ile | Leu |
| 145 | | | | | 150 | | | | | 155 | | | | | 160 |
| Ser | Lys | Ile | Asn | Gln | Pro | Tyr | Gln | Lys | Phe | Leu | Asp | Val | Leu | Asn | Thr |
| | | | | 165 | | | | | 170 | | | | | 175 | |
| Ile | Lys | Asn | Ala | Ser | Asp | Ser | Asp | Gly | Gln | Asp | Leu | Leu | Phe | Thr | Asn |
| | | | 180 | | | | | 185 | | | | | 190 | | |
| Gln | Leu | Lys | Glu | His | Pro | Thr | Asp | Phe | Ser | Val | Glu | Phe | Leu | Glu | Gln |
| | | 195 | | | | | 200 | | | | | 205 | | | |
| Asn | Ser | Asn | Glu | Val | Gln | Glu | Val | Phe | Ala | Lys | Ala | Phe | Ala | Tyr | Tyr |
| | 210 | | | | | 215 | | | | | 220 | | | | |
| Ile | Glu | Pro | Gln | His | Arg | Asp | Val | Leu | Gln | Leu | Tyr | Ala | Pro | Glu | Ala |
| 225 | | | | | 230 | | | | | 235 | | | | | 240 |

| | | | | | | | | | | | | | |
|---|---|---|---|---|---|---|---|---|---|---|---|---|---|
| Phe | Asn | Tyr | Met | Asp | Lys | Phe | Asn | Glu | Gln | Glu | Ile | Asn | Leu | Thr | Arg |
| | | | 245 | | | | 250 | | | | | 255 |
| Ala | Ala | Asn | Ala | Asp | Val | Val | Ser | Leu | Thr | Cys | Pro | Val | Ala | Ala | Gly |
| | | | 260 | | | | 265 | | | | 270 |
| Glu | Cys | Ala | Gly | Pro | Ala | Asp | Ser | Gly | Asp | Ala | Leu | Leu | Glu | Arg | Asn |
| | | 275 | | | | | 280 | | | | | 285 |
| Tyr | Pro | Thr | Gly | Ala | Glu | Phe | Leu | Gly | Asp | Gly | Gly | Asp | Val | Ser | Phe |
| | 290 | | | | | 295 | | | | 300 |
| Ser | Thr | Arg | Gly | Thr | Gln | Asn | Trp | Thr | Val | Glu | Arg | Leu | Leu | Gln | Ala |
| 305 | | | | | 310 | | | | 315 | | | | 320 |
| His | Arg | Gln | Leu | Glu | Glu | Arg | Gly | Tyr | Val | Phe | Val | Gly | Tyr | His | Gly |
| | | | 325 | | | | | 330 | | | | 335 |
| Thr | Phe | Leu | Glu | Ala | Ala | Gln | Ser | Ile | Val | Phe | Gly | Gly | Val | Arg | Ala |
| | | | 340 | | | | 345 | | | | 350 |
| Arg | Ser | Gln | Asp | Leu | Asp | Ala | Ile | Trp | Arg | Gly | Phe | Tyr | Ile | Ala | Gly |
| | | 355 | | | | | 360 | | | | 365 |
| Asp | Pro | Ala | Leu | Ala | Tyr | Gly | Tyr | Ala | Gln | Asp | Gln | Glu | Pro | Asp | Ala |
| | 370 | | | | | 375 | | | | 380 |
| Arg | Gly | Arg | Ile | Arg | Asn | Gly | Ala | Leu | Leu | Arg | Val | Tyr | Val | Pro | Arg |
| 385 | | | | | 390 | | | | 395 | | | | | 400 |
| Ser | Ser | Leu | Pro | Gly | Phe | Tyr | Arg | Thr | Ser | Leu | Thr | Leu | Ala | Ala | Pro |
| | | | | 405 | | | | 410 | | | | 415 |
| Glu | Ala | Ala | Gly | Glu | Val | Glu | Arg | Leu | Ile | Gly | His | Pro | Leu | Pro | Leu |
| | | | 420 | | | | 425 | | | | 430 |
| Arg | Leu | Asp | Ala | Ile | Thr | Gly | Pro | Glu | Glu | Glu | Gly | Gly | Arg | Leu | Glu |
| | | 435 | | | | | 440 | | | | 445 |
| Thr | Ile | Leu | Gly | Trp | Pro | Leu | Ala | Glu | Arg | Thr | Val | Val | Ile | Pro | Ser |
| | 450 | | | | | 455 | | | | 460 |
| Ala | Ile | Pro | Thr | Asp | Pro | Arg | Asn | Val | Gly | Gly | Asp | Leu | Asp | Pro | Ser |
| 465 | | | | | 470 | | | | 475 | | | | 480 |
| Ser | Ile | Pro | Asp | Lys | Glu | Gln | Ala | Ile | Ser | Ala | Leu | Pro | Asp | Tyr | Ala |
| | | | 485 | | | | 490 | | | | 495 |
| Ser | Gln | Pro | Gly | Lys | Pro | Pro | Arg | Glu | Asp | Leu | Lys |
| | | | 500 | | | | 505 |

( 2 ) INFORMATION FOR SEQ ID NO:11:

( i ) SEQUENCE CHARACTERISTICS:
        ( A ) LENGTH: 2709 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2709

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| GAA | GTT | AAA | CAG | GAG | AAC | CGG | TTA | TTA | AAT | GAA | TCA | GAA | TCA | AGT | TCC | 48 |
| Glu | Val | Lys | Gln | Glu | Asn | Arg | Leu | Leu | Asn | Glu | Ser | Glu | Ser | Ser | Ser | |
| 1 | | | | 5 | | | | | 10 | | | | | 15 | | |
| CAG | GGG | TTA | CTA | GGA | TAC | TAT | TTT | AGT | GAT | TTG | AAT | TTT | CAA | GCA | CCC | 96 |
| Gln | Gly | Leu | Leu | Gly | Tyr | Tyr | Phe | Ser | Asp | Leu | Asn | Phe | Gln | Ala | Pro | |
| | | | 20 | | | | | 25 | | | | | 30 | | |
| ATG | GTG | GTT | ACC | TCT | TCT | ACT | ACA | GGG | GAT | TTA | TCT | ATT | CCT | AGT | TCT | 144 |
| Met | Val | Val | Thr | Ser | Ser | Thr | Thr | Gly | Asp | Leu | Ser | Ile | Pro | Ser | Ser | |
| | | | 35 | | | | 40 | | | | | 45 | | | |

| | | | | | | | | | | | | | | | | |
|---|---|---|---|---|---|---|---|---|---|---|---|---|---|---|---|---|
| GAG | TTA | GAA | AAT | ATT | CCA | TCG | GAA | AAC | CAA | TAT | TTT | CAA | TCT | GCT | ATT | 192 |
| Glu | Leu | Glu | Asn | Ile | Pro | Ser | Glu | Asn | Gln | Tyr | Phe | Gln | Ser | Ala | Ile | |
| | 50 | | | | 55 | | | | 60 | | | | | | | |
| TGG | TCA | GGA | TTT | ATC | AAA | GTT | AAG | AAG | AGT | GAT | GAA | TAT | ACA | TTT | GCT | 240 |
| Trp | Ser | Gly | Phe | Ile | Lys | Val | Lys | Lys | Ser | Asp | Glu | Tyr | Thr | Phe | Ala | |
| 65 | | | | 70 | | | | | 75 | | | | | | 80 | |
| ACT | TCC | GCT | GAT | AAT | CAT | GTA | ACA | ATG | TGG | GTA | GAT | GAC | CAA | GAA | GTG | 288 |
| Thr | Ser | Ala | Asp | Asn | His | Val | Thr | Met | Trp | Val | Asp | Asp | Gln | Glu | Val | |
| | | | | 85 | | | | | 90 | | | | | 95 | | |
| ATT | AAT | AAA | GCT | TCT | AAT | TCT | AAC | AAA | ATC | AGA | TTA | GAA | AAA | GGA | AGA | 336 |
| Ile | Asn | Lys | Ala | Ser | Asn | Ser | Asn | Lys | Ile | Arg | Leu | Glu | Lys | Gly | Arg | |
| | | | 100 | | | | | 105 | | | | | 110 | | | |
| TTA | TAT | CAA | ATA | AAA | ATT | CAA | TAT | CAA | CGA | GAA | AAT | CCT | ACT | GAA | AAA | 384 |
| Leu | Tyr | Gln | Ile | Lys | Ile | Gln | Tyr | Gln | Arg | Glu | Asn | Pro | Thr | Glu | Lys | |
| | | | 115 | | | | 120 | | | | | 125 | | | | |
| GGA | TTG | GAT | TTC | AAG | TTG | TAC | TGG | ACC | GAT | TCT | CAA | AAT | AAA | AAA | GAA | 432 |
| Gly | Leu | Asp | Phe | Lys | Leu | Tyr | Trp | Thr | Asp | Ser | Gln | Asn | Lys | Lys | Glu | |
| | 130 | | | | | 135 | | | | | 140 | | | | | |
| GTG | ATT | TCT | AGT | GAT | AAC | TTA | CAA | TTG | CCA | GAA | TTA | AAA | CAA | AAA | TCT | 480 |
| Val | Ile | Ser | Ser | Asp | Asn | Leu | Gln | Leu | Pro | Glu | Leu | Lys | Gln | Lys | Ser | |
| 145 | | | | | 150 | | | | | 155 | | | | | 160 | |
| TCG | AAC | TCA | AGA | AAA | AAG | CGA | AGT | ACA | AGT | GCT | GGA | CCT | ACG | GTT | CCA | 528 |
| Ser | Asn | Ser | Arg | Lys | Lys | Arg | Ser | Thr | Ser | Ala | Gly | Pro | Thr | Val | Pro | |
| | | | | 165 | | | | | 170 | | | | | 175 | | |
| GAC | CGT | GAC | AAT | GAT | GGA | ATC | CCT | GAT | TCA | TTA | GAG | GTA | GAA | GGA | TAT | 576 |
| Asp | Arg | Asp | Asn | Asp | Gly | Ile | Pro | Asp | Ser | Leu | Glu | Val | Glu | Gly | Tyr | |
| | | | 180 | | | | | 185 | | | | | 190 | | | |
| ACG | GTT | GAT | GTC | AAA | AAT | AAA | AGA | ACT | TTT | CTT | TCA | CCA | TGG | ATT | TCT | 624 |
| Thr | Val | Asp | Val | Lys | Asn | Lys | Arg | Thr | Phe | Leu | Ser | Pro | Trp | Ile | Ser | |
| | | | 195 | | | | | 200 | | | | | 205 | | | |
| AAT | ATT | CAT | GAA | AAG | AAA | GGA | TTA | ACC | AAA | TAT | AAA | TCA | TCT | CCT | GAA | 672 |
| Asn | Ile | His | Glu | Lys | Lys | Gly | Leu | Thr | Lys | Tyr | Lys | Ser | Ser | Pro | Glu | |
| | 210 | | | | | 215 | | | | | 220 | | | | | |
| AAA | TGG | AGC | ACG | GCT | TCT | GAT | CCG | TAC | AGT | GAT | TTC | GAA | AAG | GTT | ACA | 720 |
| Lys | Trp | Ser | Thr | Ala | Ser | Asp | Pro | Tyr | Ser | Asp | Phe | Glu | Lys | Val | Thr | |
| 225 | | | | | 230 | | | | | 235 | | | | | 240 | |
| GGA | CGG | ATT | GAT | AAG | AAT | GTA | TCA | CCA | GAG | GCA | AGA | CAC | CCC | CTT | GTG | 768 |
| Gly | Arg | Ile | Asp | Lys | Asn | Val | Ser | Pro | Glu | Ala | Arg | His | Pro | Leu | Val | |
| | | | | 245 | | | | | 250 | | | | | 255 | | |
| GCA | GCT | TAT | CCG | ATT | GTA | CAT | GTA | GAT | ATG | GAG | AAT | ATT | ATT | CTC | TCA | 816 |
| Ala | Ala | Tyr | Pro | Ile | Val | His | Val | Asp | Met | Glu | Asn | Ile | Ile | Leu | Ser | |
| | | | 260 | | | | | 265 | | | | | 270 | | | |
| AAA | AAT | GAG | GAT | CAA | TCC | ACA | CAG | AAT | ACT | GAT | AGT | GAA | ACG | AGA | ACA | 864 |
| Lys | Asn | Glu | Asp | Gln | Ser | Thr | Gln | Asn | Thr | Asp | Ser | Glu | Thr | Arg | Thr | |
| | | | 275 | | | | | 280 | | | | | 285 | | | |
| ATA | AGT | AAA | AAT | ACT | TCT | ACA | AGT | AGG | ACA | CAT | ACT | AGT | GAA | GTA | CAT | 912 |
| Ile | Ser | Lys | Asn | Thr | Ser | Thr | Ser | Arg | Thr | His | Thr | Ser | Glu | Val | His | |
| | 290 | | | | | 295 | | | | | 300 | | | | | |
| GGA | AAT | GCA | GAA | GTG | CAT | GCG | TCG | TTC | TTT | GAT | ATT | GGT | GGG | AGT | GTA | 960 |
| Gly | Asn | Ala | Glu | Val | His | Ala | Ser | Phe | Phe | Asp | Ile | Gly | Gly | Ser | Val | |
| 305 | | | | | 310 | | | | | 315 | | | | | 320 | |
| TCT | GCA | GGA | TTT | AGT | AAT | TCG | AAT | TCA | AGT | ACG | GTC | GCA | ATT | GAT | CAT | 1008 |
| Ser | Ala | Gly | Phe | Ser | Asn | Ser | Asn | Ser | Ser | Thr | Val | Ala | Ile | Asp | His | |
| | | | | 325 | | | | | 330 | | | | | 335 | | |
| TCA | CTA | TCT | CTA | GCA | GGG | GAA | AGA | ACT | TGG | GCT | GAA | ACA | ATG | GGT | TTA | 1056 |
| Ser | Leu | Ser | Leu | Ala | Gly | Glu | Arg | Thr | Trp | Ala | Glu | Thr | Met | Gly | Leu | |
| | | | 340 | | | | | 345 | | | | | 350 | | | |
| AAT | ACC | GCT | GAT | ACA | GCA | AGA | TTA | AAT | GCC | AAT | ATT | AGA | TAT | GTA | AAT | 1104 |
| Asn | Thr | Ala | Asp | Thr | Ala | Arg | Leu | Asn | Ala | Asn | Ile | Arg | Tyr | Val | Asn | |
| | | 355 | | | | | 360 | | | | | 365 | | | | |

| | | | | | | | | | | | | | | | | |
|---|---|---|---|---|---|---|---|---|---|---|---|---|---|---|---|---|
| ACT | GGG | ACG | GCT | CCA | ATC | TAC | AAC | GTG | TTA | CCA | ACG | ACT | TCG | TTA | GTG | 1152 |
| Thr | Gly | Thr | Ala | Pro | Ile | Tyr | Asn | Val | Leu | Pro | Thr | Thr | Ser | Leu | Val | |
| | 370 | | | | | 375 | | | | | 380 | | | | | |
| TTA | GGA | AAA | AAT | CAA | ACA | CTC | GCG | ACA | ATT | AAA | GCT | AAG | GAA | AAC | CAA | 1200 |
| Leu | Gly | Lys | Asn | Gln | Thr | Leu | Ala | Thr | Ile | Lys | Ala | Lys | Glu | Asn | Gln | |
| 385 | | | | | 390 | | | | | 395 | | | | | 400 | |
| TTA | AGT | CAA | ATA | CTT | GCA | CCT | AAT | AAT | TAT | TAT | CCT | TCT | AAA | AAC | TTG | 1248 |
| Leu | Ser | Gln | Ile | Leu | Ala | Pro | Asn | Asn | Tyr | Tyr | Pro | Ser | Lys | Asn | Leu | |
| | | | | 405 | | | | | 410 | | | | | 415 | | |
| GCG | CCA | ATC | GCA | TTA | AAT | GCA | CAA | GAC | GAT | TTC | AGT | TCT | ACT | CCA | ATT | 1296 |
| Ala | Pro | Ile | Ala | Leu | Asn | Ala | Gln | Asp | Asp | Phe | Ser | Ser | Thr | Pro | Ile | |
| | | | 420 | | | | | 425 | | | | | 430 | | | |
| ACA | ATG | AAT | TAC | AAT | CAA | TTT | CTT | GAG | TTA | GAA | AAA | ACG | AAA | CAA | TTA | 1344 |
| Thr | Met | Asn | Tyr | Asn | Gln | Phe | Leu | Glu | Leu | Glu | Lys | Thr | Lys | Gln | Leu | |
| | | 435 | | | | | 440 | | | | | 445 | | | | |
| AGA | TTA | GAT | ACG | GAT | CAA | GTA | TAT | GGG | AAT | ATA | GCA | ACA | TAC | AAT | TTT | 1392 |
| Arg | Leu | Asp | Thr | Asp | Gln | Val | Tyr | Gly | Asn | Ile | Ala | Thr | Tyr | Asn | Phe | |
| | 450 | | | | | 455 | | | | | 460 | | | | | |
| GAA | AAT | GGA | AGA | GTG | AGG | GTG | GAT | ACA | GGC | TCG | AAC | TGG | AGT | GAA | GTG | 1440 |
| Glu | Asn | Gly | Arg | Val | Arg | Val | Asp | Thr | Gly | Ser | Asn | Trp | Ser | Glu | Val | |
| 465 | | | | | 470 | | | | | 475 | | | | | 480 | |
| TTA | CCG | CAA | ATT | CAA | GAA | ACA | ACT | GCA | CGT | ATC | ATT | TTT | AAT | GGA | AAA | 1488 |
| Leu | Pro | Gln | Ile | Gln | Glu | Thr | Thr | Ala | Arg | Ile | Ile | Phe | Asn | Gly | Lys | |
| | | | | 485 | | | | | 490 | | | | | 495 | | |
| GAT | TTA | AAT | CTG | GTA | GAA | AGG | CGG | ATA | GCG | GCG | GTT | AAT | CCT | AGT | GAT | 1536 |
| Asp | Leu | Asn | Leu | Val | Glu | Arg | Arg | Ile | Ala | Ala | Val | Asn | Pro | Ser | Asp | |
| | | | 500 | | | | | 505 | | | | | 510 | | | |
| CCA | TTA | GAA | ACG | ACT | AAA | CCG | GAT | ATG | ACA | TTA | AAA | GAA | GCC | CTT | AAA | 1584 |
| Pro | Leu | Glu | Thr | Thr | Lys | Pro | Asp | Met | Thr | Leu | Lys | Glu | Ala | Leu | Lys | |
| | | 515 | | | | | 520 | | | | | 525 | | | | |
| ATA | GCA | TTT | GGA | TTT | AAC | GAA | CCG | AAT | GGA | AAC | TTA | CAA | TAT | CAA | GGG | 1632 |
| Ile | Ala | Phe | Gly | Phe | Asn | Glu | Pro | Asn | Gly | Asn | Leu | Gln | Tyr | Gln | Gly | |
| | 530 | | | | | 535 | | | | | 540 | | | | | |
| AAA | GAC | ATA | ACC | GAA | TTT | GAT | TTT | AAT | TTC | GAT | CAA | CAA | ACA | TCT | CAA | 1680 |
| Lys | Asp | Ile | Thr | Glu | Phe | Asp | Phe | Asn | Phe | Asp | Gln | Gln | Thr | Ser | Gln | |
| 545 | | | | | 550 | | | | | 555 | | | | | 560 | |
| AAT | ATC | AAG | AAT | CAG | TTA | GCG | GAA | TTA | AAC | GCA | ACT | AAC | ATA | TAT | ACT | 1728 |
| Asn | Ile | Lys | Asn | Gln | Leu | Ala | Glu | Leu | Asn | Ala | Thr | Asn | Ile | Tyr | Thr | |
| | | | | 565 | | | | | 570 | | | | | 575 | | |
| GTA | TTA | GAT | AAA | ATC | AAA | TTA | AAT | GCA | AAA | ATG | AAT | ATT | TTA | ATA | AGA | 1776 |
| Val | Leu | Asp | Lys | Ile | Lys | Leu | Asn | Ala | Lys | Met | Asn | Ile | Leu | Ile | Arg | |
| | | | 580 | | | | | 585 | | | | | 590 | | | |
| GAT | AAA | CGT | TTT | CAT | TAT | GAT | AGA | AAT | AAC | ATA | GCA | GTT | GGG | GCG | GAT | 1824 |
| Asp | Lys | Arg | Phe | His | Tyr | Asp | Arg | Asn | Asn | Ile | Ala | Val | Gly | Ala | Asp | |
| | | 595 | | | | | 600 | | | | | 605 | | | | |
| GAG | TCA | GTA | GTT | AAG | GAG | GCT | CAT | AGA | GAA | GTA | ATT | AAT | TCG | TCA | ACA | 1872 |
| Glu | Ser | Val | Val | Lys | Glu | Ala | His | Arg | Glu | Val | Ile | Asn | Ser | Ser | Thr | |
| | 610 | | | | | 615 | | | | | 620 | | | | | |
| GAG | GGA | TTA | TTG | TTA | AAT | ATT | GAT | AAG | GAT | ATA | AGA | AAA | ATA | TTA | TCA | 1920 |
| Glu | Gly | Leu | Leu | Leu | Asn | Ile | Asp | Lys | Asp | Ile | Arg | Lys | Ile | Leu | Ser | |
| 625 | | | | | 630 | | | | | 635 | | | | | 640 | |
| GGT | TAT | ATT | GTA | GAA | ATT | GAA | GAT | ACT | GAA | GGG | CTT | AAA | GAA | GTT | ATA | 1968 |
| Gly | Tyr | Ile | Val | Glu | Ile | Glu | Asp | Thr | Glu | Gly | Leu | Lys | Glu | Val | Ile | |
| | | | | 645 | | | | | 650 | | | | | 655 | | |
| AAT | GAC | AGA | TAT | GAT | ATG | TTG | AAT | ATT | TCT | AGT | TTA | CGG | CAA | GAT | GGA | 2016 |
| Asn | Asp | Arg | Tyr | Asp | Met | Leu | Asn | Ile | Ser | Ser | Leu | Arg | Gln | Asp | Gly | |
| | | | 660 | | | | | 665 | | | | | 670 | | | |
| AAA | ACA | TTT | ATA | GAT | TTT | AAA | AAA | TAT | AAT | GAT | AAA | TTA | CCG | TTA | TAT | 2064 |
| Lys | Thr | Phe | Ile | Asp | Phe | Lys | Lys | Tyr | Asn | Asp | Lys | Leu | Pro | Leu | Tyr | |
| | | 675 | | | | | 680 | | | | | 685 | | | | |

| | | | | | | | | | | | | | | | | |
|---|---|---|---|---|---|---|---|---|---|---|---|---|---|---|---|---|
| ATA | AGT | AAT | CCC | AAT | TAT | AAG | GTA | AAT | GTA | TAT | GCT | GTT | ACT | AAA | GAA | 2112 |
| Ile | Ser | Asn | Pro | Asn | Tyr | Lys | Val | Asn | Val | Tyr | Ala | Val | Thr | Lys | Glu | |
| | 690 | | | | 695 | | | | | 700 | | | | | | |
| AAC | ACT | ATT | ATT | AAT | CCT | AGT | GAG | AAT | GGG | GAT | ACT | AGT | ACC | AAC | GGG | 2160 |
| Asn | Thr | Ile | Ile | Asn | Pro | Ser | Glu | Asn | Gly | Asp | Thr | Ser | Thr | Asn | Gly | |
| 705 | | | | | 710 | | | | | 715 | | | | | 720 | |
| ATC | AAG | AAA | ATT | TTA | AAG | AAA | GTG | GTG | CTG | GGC | AAA | AAA | GGG | GAT | ACA | 2208 |
| Ile | Lys | Lys | Ile | Leu | Lys | Lys | Val | Val | Leu | Gly | Lys | Lys | Gly | Asp | Thr | |
| | | | | 725 | | | | | 730 | | | | | 735 | | |
| GTG | GAA | CTG | ACC | TGT | ACA | GCT | TCC | CAG | AAG | AAG | AGC | ATA | CAA | TTC | CAC | 2256 |
| Val | Glu | Leu | Thr | Cys | Thr | Ala | Ser | Gln | Lys | Lys | Ser | Ile | Gln | Phe | His | |
| | | | 740 | | | | | 745 | | | | | 750 | | | |
| TGG | AAA | AAC | TCC | AAC | CAG | ATA | AAG | ATT | CTG | GGA | AAT | CAG | GGC | TCC | TTC | 2304 |
| Trp | Lys | Asn | Ser | Asn | Gln | Ile | Lys | Ile | Leu | Gly | Asn | Gln | Gly | Ser | Phe | |
| | | 755 | | | | | 760 | | | | | 765 | | | | |
| TTA | ACT | AAA | GGT | CCA | TCC | AAG | CTG | AAT | GAT | CGC | GCT | GAC | TCA | AGA | AGA | 2352 |
| Leu | Thr | Lys | Gly | Pro | Ser | Lys | Leu | Asn | Asp | Arg | Ala | Asp | Ser | Arg | Arg | |
| | 770 | | | | | 775 | | | | | 780 | | | | | |
| AGC | CTT | TGG | GAC | CAA | GGA | AAC | TTC | CCC | CTG | ATC | ATC | AAG | AAT | CTT | AAG | 2400 |
| Ser | Leu | Trp | Asp | Gln | Gly | Asn | Phe | Pro | Leu | Ile | Ile | Lys | Asn | Leu | Lys | |
| 785 | | | | | 790 | | | | | 795 | | | | | 800 | |
| ATA | GAA | GAC | TCA | GAT | ACT | TAC | ATC | TGT | GAA | GTG | GAG | GAC | CAG | AAG | GAG | 2448 |
| Ile | Glu | Asp | Ser | Asp | Thr | Tyr | Ile | Cys | Glu | Val | Glu | Asp | Gln | Lys | Glu | |
| | | | | 805 | | | | | 810 | | | | | 815 | | |
| GAG | GTG | CAA | TTG | CTA | GTG | TTC | GGA | TTG | ACT | GCC | AAC | TCT | GAC | ACC | CAC | 2496 |
| Glu | Val | Gln | Leu | Leu | Val | Phe | Gly | Leu | Thr | Ala | Asn | Ser | Asp | Thr | His | |
| | | | 820 | | | | | 825 | | | | | 830 | | | |
| CTG | CTT | CAG | GGG | CAG | AGC | CTG | ACC | CTG | ACC | TTG | GAG | AGC | CCC | CCT | GGT | 2544 |
| Leu | Leu | Gln | Gly | Gln | Ser | Leu | Thr | Leu | Thr | Leu | Glu | Ser | Pro | Pro | Gly | |
| | | 835 | | | | | 840 | | | | | 845 | | | | |
| AGT | AGC | CCC | TCA | GTG | CAA | TGT | AGG | AGT | CCA | AGG | GGT | AAA | AAC | ATA | CAG | 2592 |
| Ser | Ser | Pro | Ser | Val | Gln | Cys | Arg | Ser | Pro | Arg | Gly | Lys | Asn | Ile | Gln | |
| | 850 | | | | | 855 | | | | | 860 | | | | | |
| GGG | GGG | AAG | ACC | CTC | TCC | GTG | TCT | CAG | CTG | GAG | CTC | CAG | GAT | AGT | GGC | 2640 |
| Gly | Gly | Lys | Thr | Leu | Ser | Val | Ser | Gln | Leu | Glu | Leu | Gln | Asp | Ser | Gly | |
| 865 | | | | | 870 | | | | | 875 | | | | | 880 | |
| ACC | TGG | ACA | TGC | ACT | GTC | TTG | CAG | AAC | CAG | AAG | AAG | GTG | GAG | TTC | AAA | 2688 |
| Thr | Trp | Thr | Cys | Thr | Val | Leu | Gln | Asn | Gln | Lys | Lys | Val | Glu | Phe | Lys | |
| | | | | 885 | | | | | 890 | | | | | 895 | | |
| ATA | GAC | ATC | GTG | GTG | CTA | GCT | | | | | | | | | | 2709 |
| Ile | Asp | Ile | Val | Val | Leu | Ala | | | | | | | | | | |
| | | | 900 | | | | | | | | | | | | | |

( 2 ) INFORMATION FOR SEQ ID NO:12:

( i ) SEQUENCE CHARACTERISTICS:
        ( A ) LENGTH: 903 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | | |
|---|---|---|---|---|---|---|---|---|---|---|---|---|---|---|---|
| Glu | Val | Lys | Gln | Glu | Asn | Arg | Leu | Leu | Asn | Glu | Ser | Glu | Ser | Ser | Ser |
| 1 | | | | 5 | | | | | 10 | | | | | 15 | |
| Gln | Gly | Leu | Leu | Gly | Tyr | Tyr | Phe | Ser | Asp | Leu | Asn | Phe | Gln | Ala | Pro |
| | | | 20 | | | | | 25 | | | | | 30 | | |
| Met | Val | Val | Thr | Ser | Ser | Thr | Thr | Gly | Asp | Leu | Ser | Ile | Pro | Ser | Ser |
| | | | 35 | | | | | 40 | | | | | 45 | | |
| Glu | Leu | Glu | Asn | Ile | Pro | Ser | Glu | Asn | Gln | Tyr | Phe | Gln | Ser | Ala | Ile |
| | 50 | | | | | 55 | | | | | 60 | | | | |

| | | | | | | | | | | | | | | |
|---|---|---|---|---|---|---|---|---|---|---|---|---|---|---|
| Trp | Ser | Gly | Phe | Ile | Lys | Val | Lys | Lys | Ser | Asp | Glu | Tyr | Thr | Phe | Ala |
| 65 | | | | 70 | | | | | 75 | | | | | | 80 |
| Thr | Ser | Ala | Asp | Asn | His | Val | Thr | Met | Trp | Val | Asp | Asp | Gln | Glu | Val |
| | | | | 85 | | | | 90 | | | | | 95 | | |
| Ile | Asn | Lys | Ala | Ser | Asn | Ser | Asn | Lys | Ile | Arg | Leu | Glu | Lys | Gly | Arg |
| | | | 100 | | | | | 105 | | | | | 110 | | |
| Leu | Tyr | Gln | Ile | Lys | Ile | Gln | Tyr | Gln | Arg | Glu | Asn | Pro | Thr | Glu | Lys |
| | | | 115 | | | | 120 | | | | | 125 | | | |
| Gly | Leu | Asp | Phe | Lys | Leu | Tyr | Trp | Thr | Asp | Ser | Gln | Asn | Lys | Lys | Glu |
| | 130 | | | | | 135 | | | | | 140 | | | | |
| Val | Ile | Ser | Ser | Asp | Asn | Leu | Gln | Leu | Pro | Glu | Leu | Lys | Gln | Lys | Ser |
| 145 | | | | | 150 | | | | 155 | | | | | | 160 |
| Ser | Asn | Ser | Arg | Lys | Lys | Arg | Ser | Thr | Ser | Ala | Gly | Pro | Thr | Val | Pro |
| | | | | 165 | | | | | 170 | | | | | 175 | |
| Asp | Arg | Asp | Asn | Asp | Gly | Ile | Pro | Asp | Ser | Leu | Glu | Val | Glu | Gly | Tyr |
| | | | | 180 | | | | 185 | | | | | 190 | | |
| Thr | Val | Asp | Val | Lys | Asn | Lys | Arg | Thr | Phe | Leu | Ser | Pro | Trp | Ile | Ser |
| | | | 195 | | | | | 200 | | | | | 205 | | |
| Asn | Ile | His | Glu | Lys | Lys | Gly | Leu | Thr | Lys | Tyr | Lys | Ser | Ser | Pro | Glu |
| | 210 | | | | | 215 | | | | | 220 | | | | |
| Lys | Trp | Ser | Thr | Ala | Ser | Asp | Pro | Tyr | Ser | Asp | Phe | Glu | Lys | Val | Thr |
| 225 | | | | | 230 | | | | | 235 | | | | | 240 |
| Gly | Arg | Ile | Asp | Lys | Asn | Val | Ser | Pro | Glu | Ala | Arg | His | Pro | Leu | Val |
| | | | | 245 | | | | | 250 | | | | | 255 | |
| Ala | Ala | Tyr | Pro | Ile | Val | His | Val | Asp | Met | Glu | Asn | Ile | Ile | Leu | Ser |
| | | | 260 | | | | | 265 | | | | | 270 | | |
| Lys | Asn | Glu | Asp | Gln | Ser | Thr | Gln | Asn | Thr | Asp | Ser | Glu | Thr | Arg | Thr |
| | | 275 | | | | | 280 | | | | | 285 | | | |
| Ile | Ser | Lys | Asn | Thr | Ser | Thr | Ser | Arg | Thr | His | Thr | Ser | Glu | Val | His |
| | 290 | | | | | 295 | | | | | 300 | | | | |
| Gly | Asn | Ala | Glu | Val | His | Ala | Ser | Phe | Phe | Asp | Ile | Gly | Gly | Ser | Val |
| 305 | | | | | 310 | | | | | 315 | | | | | 320 |
| Ser | Ala | Gly | Phe | Ser | Asn | Ser | Asn | Ser | Ser | Thr | Val | Ala | Ile | Asp | His |
| | | | | 325 | | | | | 330 | | | | | 335 | |
| Ser | Leu | Ser | Leu | Ala | Gly | Glu | Arg | Thr | Trp | Ala | Glu | Thr | Met | Gly | Leu |
| | | | 340 | | | | | 345 | | | | | 350 | | |
| Asn | Thr | Ala | Asp | Thr | Ala | Arg | Leu | Asn | Ala | Asn | Ile | Arg | Tyr | Val | Asn |
| | | 355 | | | | | 360 | | | | | 365 | | | |
| Thr | Gly | Thr | Ala | Pro | Ile | Tyr | Asn | Val | Leu | Pro | Thr | Thr | Ser | Leu | Val |
| | 370 | | | | | 375 | | | | | 380 | | | | |
| Leu | Gly | Lys | Asn | Gln | Thr | Leu | Ala | Thr | Ile | Lys | Ala | Lys | Glu | Asn | Gln |
| 385 | | | | | 390 | | | | | 395 | | | | | 400 |
| Leu | Ser | Gln | Ile | Leu | Ala | Pro | Asn | Asn | Tyr | Tyr | Pro | Ser | Lys | Asn | Leu |
| | | | | 405 | | | | | 410 | | | | | 415 | |
| Ala | Pro | Ile | Ala | Leu | Asn | Ala | Gln | Asp | Asp | Phe | Ser | Ser | Thr | Pro | Ile |
| | | | 420 | | | | | 425 | | | | | 430 | | |
| Thr | Met | Asn | Tyr | Asn | Gln | Phe | Leu | Glu | Leu | Glu | Lys | Thr | Lys | Gln | Leu |
| | | 435 | | | | | 440 | | | | | 445 | | | |
| Arg | Leu | Asp | Thr | Asp | Gln | Val | Tyr | Gly | Asn | Ile | Ala | Thr | Tyr | Asn | Phe |
| | 450 | | | | | 455 | | | | | 460 | | | | |
| Glu | Asn | Gly | Arg | Val | Arg | Val | Asp | Thr | Gly | Ser | Asn | Trp | Ser | Glu | Val |
| 465 | | | | | 470 | | | | | 475 | | | | | 480 |
| Leu | Pro | Gln | Ile | Gln | Glu | Thr | Thr | Ala | Arg | Ile | Ile | Phe | Asn | Gly | Lys |

|     |     |     |     |     |     |     | 485 |     |     |     |     | 490 |     |     |     |     | 495 |     |     |
| --- | --- | --- | --- | --- | --- | --- | --- | --- | --- | --- | --- | --- | --- | --- | --- | --- | --- | --- | --- |
| Asp | Leu | Asn | Leu | Val | Glu | Arg | Arg | Ile | Ala | Ala | Val | Asn | Pro | Ser | Asp |
|     |     |     | 500 |     |     |     | 505 |     |     |     |     | 510 |     |     |     |
| Pro | Leu | Glu | Thr | Thr | Lys | Pro | Asp | Met | Thr | Leu | Lys | Glu | Ala | Leu | Lys |
|     |     |     | 515 |     |     |     | 520 |     |     |     |     | 525 |     |     |     |
| Ile | Ala | Phe | Gly | Phe | Asn | Glu | Pro | Asn | Gly | Asn | Leu | Gln | Tyr | Gln | Gly |
|     |     |     | 530 |     |     |     | 535 |     |     |     |     | 540 |     |     |     |
| Lys | Asp | Ile | Thr | Glu | Phe | Asp | Phe | Asn | Phe | Asp | Gln | Gln | Thr | Ser | Gln |
| 545 |     |     |     |     |     | 550 |     |     |     |     |     | 555 |     |     | 560 |
| Asn | Ile | Lys | Asn | Gln | Leu | Ala | Glu | Leu | Asn | Ala | Thr | Asn | Ile | Tyr | Thr |
|     |     |     |     | 565 |     |     |     |     | 570 |     |     |     |     | 575 |     |
| Val | Leu | Asp | Lys | Ile | Lys | Leu | Asn | Ala | Lys | Met | Asn | Ile | Leu | Ile | Arg |
|     |     |     | 580 |     |     |     |     |     | 585 |     |     |     |     | 590 |     |
| Asp | Lys | Arg | Phe | His | Tyr | Asp | Arg | Asn | Asn | Ile | Ala | Val | Gly | Ala | Asp |
|     |     |     | 595 |     |     |     | 600 |     |     |     |     | 605 |     |     |     |
| Glu | Ser | Val | Val | Lys | Glu | Ala | His | Arg | Glu | Val | Ile | Asn | Ser | Ser | Thr |
|     | 610 |     |     |     |     | 615 |     |     |     |     | 620 |     |     |     |     |
| Glu | Gly | Leu | Leu | Leu | Asn | Ile | Asp | Lys | Asp | Ile | Arg | Lys | Ile | Leu | Ser |
| 625 |     |     |     |     | 630 |     |     |     |     | 635 |     |     |     |     | 640 |
| Gly | Tyr | Ile | Val | Glu | Ile | Glu | Asp | Thr | Glu | Gly | Leu | Lys | Glu | Val | Ile |
|     |     |     |     | 645 |     |     |     |     | 650 |     |     |     |     | 655 |     |
| Asn | Asp | Arg | Tyr | Asp | Met | Leu | Asn | Ile | Ser | Ser | Leu | Arg | Gln | Asp | Gly |
|     |     |     | 660 |     |     |     |     | 665 |     |     |     |     | 670 |     |     |
| Lys | Thr | Phe | Ile | Asp | Phe | Lys | Lys | Tyr | Asn | Asp | Lys | Leu | Pro | Leu | Tyr |
|     |     |     | 675 |     |     |     |     | 680 |     |     |     |     | 685 |     |     |
| Ile | Ser | Asn | Pro | Asn | Tyr | Lys | Val | Asn | Val | Tyr | Ala | Val | Thr | Lys | Glu |
|     |     |     | 690 |     |     |     |     | 695 |     |     |     |     | 700 |     |     |
| Asn | Thr | Ile | Ile | Asn | Pro | Ser | Glu | Asn | Gly | Asp | Thr | Ser | Thr | Asn | Gly |
| 705 |     |     |     |     | 710 |     |     |     |     | 715 |     |     |     |     | 720 |
| Ile | Lys | Lys | Ile | Leu | Lys | Lys | Val | Val | Leu | Gly | Lys | Lys | Gly | Asp | Thr |
|     |     |     |     |     | 725 |     |     |     |     | 730 |     |     |     |     | 735 |
| Val | Glu | Leu | Thr | Cys | Thr | Ala | Ser | Gln | Lys | Lys | Ser | Ile | Gln | Phe | His |
|     |     |     | 740 |     |     |     |     | 745 |     |     |     |     | 750 |     |     |
| Trp | Lys | Asn | Ser | Asn | Gln | Ile | Lys | Ile | Leu | Gly | Asn | Gln | Gly | Ser | Phe |
|     |     |     | 755 |     |     |     |     | 760 |     |     |     |     | 765 |     |     |
| Leu | Thr | Lys | Gly | Pro | Ser | Lys | Leu | Asn | Asp | Arg | Ala | Asp | Ser | Arg | Arg |
|     |     |     | 770 |     |     |     |     | 775 |     |     |     |     | 780 |     |     |
| Ser | Leu | Trp | Asp | Gln | Gly | Asn | Phe | Pro | Leu | Ile | Ile | Lys | Asn | Leu | Lys |
| 785 |     |     |     |     |     | 790 |     |     |     |     | 795 |     |     |     | 800 |
| Ile | Glu | Asp | Ser | Asp | Thr | Tyr | Ile | Cys | Glu | Val | Glu | Asp | Gln | Lys | Glu |
|     |     |     |     | 805 |     |     |     |     | 810 |     |     |     |     | 815 |     |
| Glu | Val | Gln | Leu | Leu | Val | Phe | Gly | Leu | Thr | Ala | Asn | Ser | Asp | Thr | His |
|     |     |     |     | 820 |     |     |     |     | 825 |     |     |     |     | 830 |     |
| Leu | Leu | Gln | Gly | Gln | Ser | Leu | Thr | Leu | Thr | Leu | Glu | Ser | Pro | Pro | Gly |
|     |     |     | 835 |     |     |     |     | 840 |     |     |     |     | 845 |     |     |
| Ser | Ser | Pro | Ser | Val | Gln | Cys | Arg | Ser | Pro | Arg | Gly | Lys | Asn | Ile | Gln |
|     | 850 |     |     |     |     | 855 |     |     |     |     | 860 |     |     |     |     |
| Gly | Gly | Lys | Thr | Leu | Ser | Val | Ser | Gln | Leu | Glu | Leu | Gln | Asp | Ser | Gly |
| 865 |     |     |     |     | 870 |     |     |     |     | 875 |     |     |     |     | 880 |
| Thr | Trp | Thr | Cys | Thr | Val | Leu | Gln | Asn | Gln | Lys | Lys | Val | Glu | Phe | Lys |
|     |     |     |     | 885 |     |     |     |     | 890 |     |     |     |     | 895 |     |
| Ile | Asp | Ile | Val | Val | Leu | Ala |
|     |     |     | 900 |     |     |     |